US009403911B2

(12) United States Patent
Batra et al.

(10) Patent No.: US 9,403,911 B2
(45) Date of Patent: Aug. 2, 2016

(54) COMPOSITIONS AND METHODS FOR DETECTION AND TREATMENT OF CANCER

(75) Inventors: Surinder K. Batra, Omaha, NE (US); Maneesh Jain, Omaha, NE (US); Moorthy P. Ponnusamy, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 14/122,171

(22) PCT Filed: Jun. 6, 2012

(86) PCT No.: PCT/US2012/041007
§ 371 (c)(1),
(2), (4) Date: Mar. 24, 2014

(87) PCT Pub. No.: WO2012/170470
PCT Pub. Date: Dec. 13, 2012

(65) Prior Publication Data
US 2014/0199242 A1    Jul. 17, 2014

Related U.S. Application Data

(60) Provisional application No. 61/493,688, filed on Jun. 6, 2011.

(51) Int. Cl.
*C07K 16/30* (2006.01)
*G01N 33/574* (2006.01)
*A61K 49/00* (2006.01)

(52) U.S. Cl.
CPC ............. *C07K 16/3092* (2013.01); *A61K 49/00* (2013.01); *G01N 33/574* (2013.01); *G01N 33/57411* (2013.01); *G01N 33/57438* (2013.01); *G01N 33/57446* (2013.01); *G01N 33/57449* (2013.01); *G01N 2333/4725* (2013.01); *G01N 2400/02* (2013.01)

(58) Field of Classification Search
CPC ........................... C07K 16/3092; C07K 16/00
USPC ............................................. 530/388.8, 388.1
See application file for complete search history.

(56) References Cited

U.S. PATENT DOCUMENTS

| 6,576,423 B2 | 6/2003 | Batra et al. |
| 6,812,339 B1 | 11/2004 | Venter et al. |
| 7,052,859 B2 | 5/2006 | Batra et al. |
| 7,078,188 B2 | 7/2006 | Batra et al. |
| 7,105,657 B2 | 9/2006 | Batra et al. |
| 7,473,531 B1 * | 1/2009 | Domon et al. ................. 435/7.1 |
| 2004/0091869 A1 | 5/2004 | Batra et al. |

FOREIGN PATENT DOCUMENTS

WO    2012/170470    12/2012

OTHER PUBLICATIONS

Pflugfelder et al. (Invest Ophthalmol Vis Sci. 2000, 41: 1316-1326).*
UniProt databases-MUC4, pp. 1-26, Mar. 10, 2015.*
PCT International Search Report and Written Opinion dated Oct. 16, 2012 issued in PCT/US2012/041007 [WO 2012/170470].
PCT International Preliminary Report on Patentability and Written Opinion dated Dec. 27, 2013 issued in PCT/US2012/041007 [WO 2012/170470].
Bafna et al. (2010) "Membrane-bound mucins: the mechanistic basis for alterations in the growth and survival of cancer cells," *Oncogene* 29(20): 2893-2904.
Chaturvedi et al. (2007) "MUC4 Mucin Potentiates Pancreatic Tumor Cell Proliferation, Survival, and Invasive Properties and Interferes with Its Interaction to Extracellular Matrix Proteins," *Mol. Canc. Res.*, 5(4): 309-320.
Choudhury et al. (2000) "Human MUC4 Mucin cDNA and Its Variants in Pancreatic Carcinoma," *J. Biochem.* 128(2): 233-243, abstract only; downloaded from http://jb.oxfordjournals.org/content/128/2/233.abstract on Aug. 24, 2012.
GenBank Deposition CAB81773.1 mucin 4 [*Homo sapiens*] Oct. 21, 2008.
Hezel et al. (2006) "Genetics and biology of pancreatic ductal adenocarcinoma," *Genes & Dev.* 20: 1218-1249.
Jain et al. (2011) "Monoclonal Antibodies Recognizing the Non-Tandem Repeat Regions of the Human Mucin MUC4 in Pancreatic Cancer," *PLoS One*, 6(8): e23344.
Jonckheere and Seuningen (2008) "The Membrane-Bound Mucins: How Large O-Glycoproteins Play Key Roles in Epithelial Cancers and Hold Promise as Biological Tools for Gene-Based and Immunotherapies," *Crit. Rev. Oncogenesis* 14(2-3): 177-196.
Moniaux et al. (2004) "Generation and Characterization of Anti-MUC4 Monoclonal Antibodies Reactive with Normal and Cancer Cells in Humans," *J. Histochem. Cytochem.*, 52(2): 253-261.
Nollet et al. (1998) "Human mucin gene MUC4: organization of its 5'-region and polymorphism of its central tandem repeat array," *Biochem. J.* 332: 739-748.
Pflugfelder et al. (2000) "Detection of Sialomucin Complex (MUC4) in Human Ocular Surface Epithelium and Tear Fluid," *Invest. Ophthalmol. Vis. Sci.*, 41(6): 1316-1326.
Ponnusamy et al. (2011) "MUC4 stabilizes HER2 expression and maintains the cancer stem cell population in ovarian cancer cells," *J. Ovarian Res.*, 4(7).
Wittel et al. (2002) "Mucin Antibodies—New Tools in Diagnosis and Therapy of Cancer," *Frontiers in Bioscience* (6): d1296-1310.

* cited by examiner

*Primary Examiner* — Yan Xiao
(74) *Attorney, Agent, or Firm* — Tom Hunter; Weaver Austin Villeneuve & Sampson LLP

(57) ABSTRACT

Novel antibodies for the detection and/or treatment of a cancer (e.g., a pancreatic cancer or an ovarian cancer) are provided. In certain embodiments the antibodies bind a region of the MUC4 protein that does not comprise the central tandem repeat (TR) domain of MUC4. Certain antibodies bind to the MUC4 peptide fragment MUC4-α-N-Ter and/or to the MUC4 peptide fragment MUC4-α-C-Ter. Chimeric constructs comprising such antibodies are also provided.

17 Claims, 17 Drawing Sheets

MUC4α N-Ter

WVNAHAYPAQWTLGSNTYQAILSTDGSRSYALFLYQSGGMQWDVAQRSGNPVL
MGFSSGDGYFENSPLMSQPVWERYRPDRFLNSNSGLQGLQFYRLHREERPNYR
LECLQWLKSQPRWPSWGWNQVSCPCSWQQGRRDLRFQPVSIGRWGLGSRQL
CSFTSWRGGVCCSYGPWGEFREGWHVQRPWQLAQELEPQSWCCRWNDKPYL
CALYQQRRPHVGCATYRPPQPAWMFGDPHITTLDGVSYTFNGLGDFLLVGAQDG
NSSFLLQGRTAQTGSAQATNFIAFAAQYRSSSLGPVTVQWLLEPHDAIRVLLDNQ
TVTFQPDHEDGGGQETFNATGVLLSRNGSEVSASFDGWATVSVIALSNILHASAS
LPPEYQNRTEGLLGVWNNNPEDDFRMPNGSTIPPGSPEEMLFHFGMTWQINGT
GLLGKRNDQLPSNFTPVFYSQLQKNSSWAEHLISNCDGDSSCIYDTLALRNASIGL
HTREVSKNYEQANATLNQYPPSINGGRVIEAYKGQTTLIQYTSNAEDANFTLRDSC
TDLELFENGTLLWTPKSLEPFTLEILARSAKIGLASALQPRTVVCHCNAESQCLYN
QTSRVGNSSLEVAGCKCDGGTFGRYCEGSEDACEEPCFPSVHCVPGKGCEACP
PNLTGDGRHCAALGSSFLCQNQSCPVNYCYNQGHCYISQTLGCQPMCTPPAFT
DSRCFLAGNNFSPTVNLELPLRVIQLLLSEEENASMAEVNASVAYRLGTLDMRAFL
RNSQVERIDSAAPASGSPIQHWMVISEFQYRPRGPVIDFLNNQLLAAVVEAFLYHV
PRRSEEPRNDVVFQPISEEDVRDVTALNVSTLKAYFRCDGYKGYDLVYSPQSGFT
CVSPCSRGYCDHGGQCQHLPSGPRCSCVSFSIYTAWGEHCEHLSMKLDAFFGIF
FGA

*Fig. 1A*

MUC4α C-Ter

PLKMETSGMTTPSLKTDGGRRTATSPPPTTSQTIISTIPSTAMHTRSTAAPIPILPER
GVSLFPYGADAGDLEFVRRTVDFTSPLFKPATGFPLGSSLRDSLYFTDNGQIIFPE
SDYQIFSYPNPLPTGFTGRDPVALVAPFWDDADFSTGRGTTFYQEYETFYGEHSL
LVQQAESWIRKITNNGGYKARWALKVTWVNAHAYPAQWTLGSNTYQAILSTDGS
RSYALFLYQSGGMQWDVAQRSGKPVLMGFSSGDGFFENSPLMSQPVWERYRP
DRFLNSNSGLQGLQFYGLHREERPNYRLECLQWLKSQPRWPSWGWNQVSCPC
SWQQGRRDLRFQPVSIGRWGLGSRQLCSFTSWRGGVCCSYGPWGEFREGWH
VQRPWQLAQELEPQSWCCRWNDKPYLCALYQQRRPHVGCATYRPPQPAWMF
GD

*Fig. 1B*

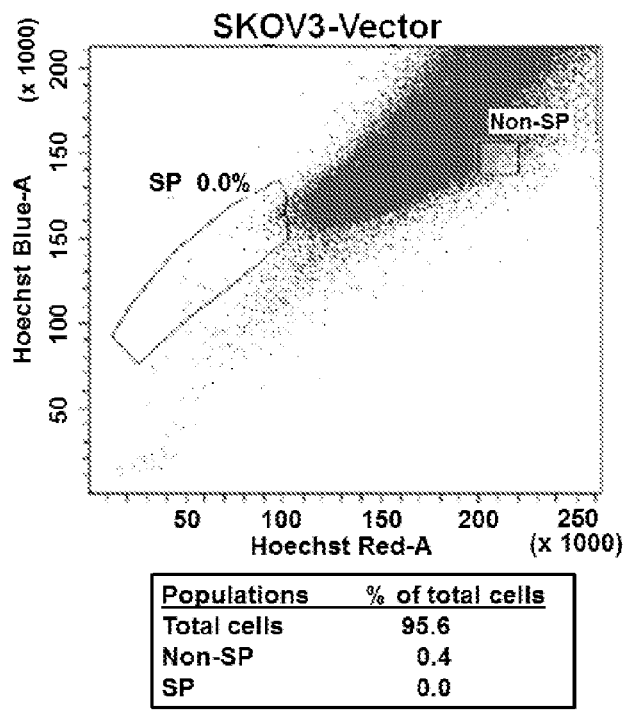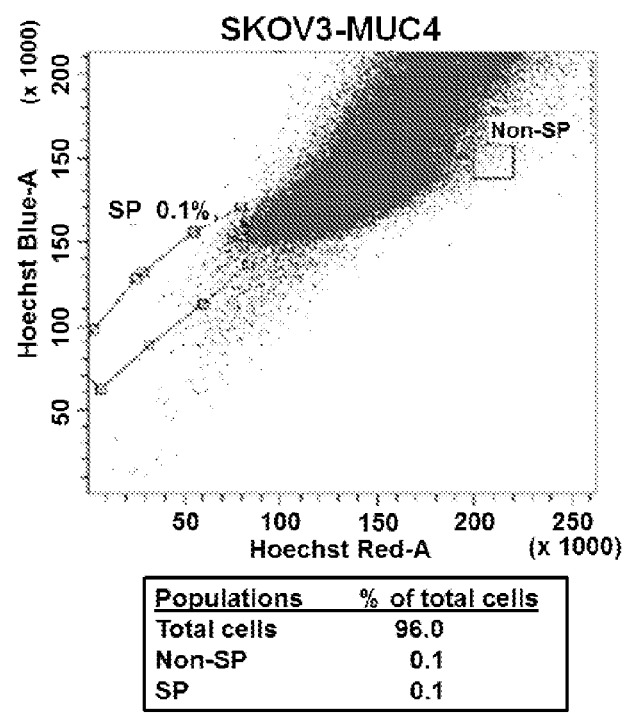
Fig. 9A

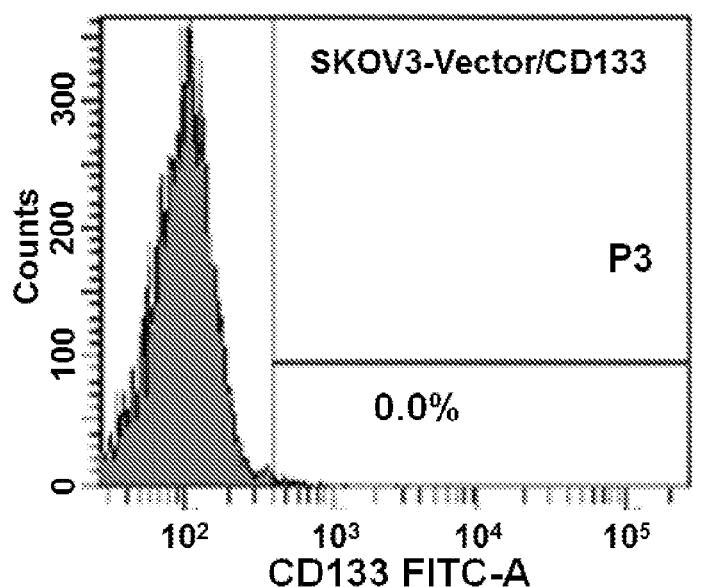
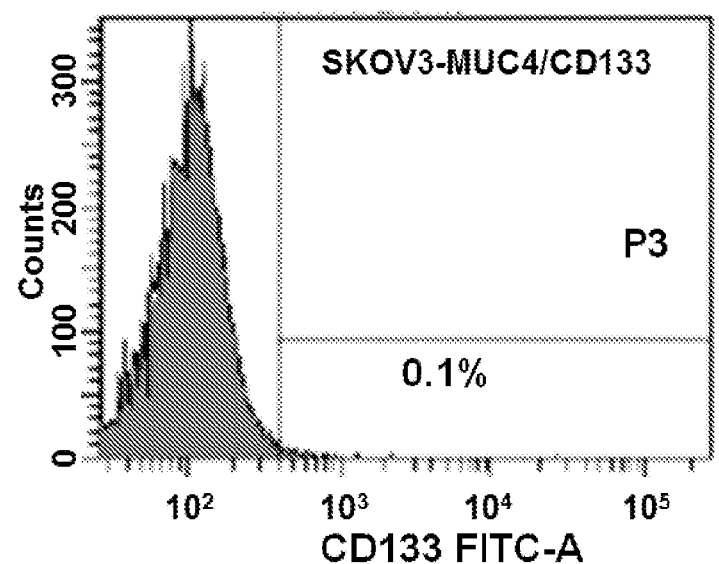
Fig. 9B

COMPOSITIONS AND METHODS FOR DETECTION AND TREATMENT OF CANCER

CROSS-REFERENCE TO RELATED APPLICATIONS

This application is a 371 National Phase of PCT/US2012/041007, filed on Jun. 6, 2012, which claims benefit of and priority to U.S. Ser. No. 61/493,688, filed on Jun. 6, 2011, which is incorporated herein by reference in its entirety for all purposes.

STATEMENT OF GOVERNMENTAL SUPPORT

This invention was made with government support under Grant Nos. OC04110, R01 CA78590, CA131944, and CA133774 awarded by the National Institutes of Health. The government has certain rights in the invention.

BACKGROUND

Mucins are high molecular weight glycoproteins that are involved in many biological functions. MUC 4, a member of the transmembrane mucin family, encodes a human epithelial mucin that is expressed in numerous epithelial tissues and is found in bodily fluids such as saliva, tears, and breast milk. Additionally, MUC4 is expressed in undifferentiated cells of the embryo and fetus. Human MUC4 has been found to contain two subunits, MUC4α and MUC4β. While the MUC4α subunit is largely extracellular, MUC4β is a transmembrane domain that has many implications in cell signaling in both normal and carcinogenic situations.

There are numerous studies that clearly establish the involvement of MUC4 with the progression of cancer and metastasis. Due in part to the fact that MUC4 contains extracellular domains, it has been proposed that MUC4 has a direct role in cell signaling pathways and subsequent behavior of tumor cells. One particular area of interest is the role MUC4 and oncogenesis. In recent studies, MUC4 was ectopically expressed in fibroblast cells resulting in enhanced levels of oncoprotein ErbB2 and tumor formation in nude mice. MUC4β is composed of two domains that are similar to epidermal growth factor, a transmembrane sequence and may have the ability to bind the receptor tyrosine kinase. This suggests that MUC4 plays a distinct role as a ligand in ErbB2 cell signaling likely by stabilizing and enhancing the activity of ErbB2 growth factor receptor. In addition to ErbB2, silencing of MUC4 in pancreatic cancer cells was associated with down regulation of HER2 and a subsequent reduction in its ability to contribute to tumorgenesis. MUC4 also contains a heavily glycosylated tandem repeat domain which provides structural rigidity to the extended cellular region thus serving as a barrier for some cell-cell and cell-extracellular matrix interactions subsequently allowing it to act as a reservoir for certain growth factors.

Further evidence for the relationship between MUC4 and growth factor signaling is seen in the fact that the MUC4 promoter region contains binding sites for different transcription factors such as interferon-Γ, retinoic acid and transforming growth factor-13 that in turn are responsible for the regulation of its expression in different tissues.

SUMMARY

The present invention provides a novel class of monoclonal antibodies that binds to non-TR domains of MUC4 (e.g., MUC4α N-ter (SEQ ID NO: 1) and/or MUC4α C-ter (SEQ ID NO: 2)) and that are useful for the diagnosis and/or treatment of neoplasias characterized by upregulation of MUC4.

Antibodies of the present invention include all known forms of antibodies and other protein scaffolds with antibody-like properties. For example, the antibody can be a human antibody, a humanized antibody, a bispecific antibody, a chimeric antibody or a protein scaffold with antibody-like properties, such as fibronectin or Ankyrin repeats. The antibody also can be a Fab, Fab'$_2$, ScFv, SMIP, affibody, nanobody, or a domain antibody. In various embodiments the antibody also can have any of the following isotypes: IgG1, IgG2, IgG3, IgG4, IgM, IgA1, IgA2, IgAsec, IgD, and IgE.

In yet another embodiment, the present invention further provides compositions comprising combinations of antibodies or antigen binding portions described herein, formulated with an acceptable carrier and/or excipient.

In certain embodiments an antibody that binds a region of the MUC4 protein that does not comprise the central tandem repeat (TR) domain of MUC4 is provided. In certain embodiments the antibody binds regions of MUC4α that are upstream of the TR domain and/or the antibody binds regions of MUC4α that are downstream of the TR domain. In certain embodiments the antibody binds to the MUC4 peptide fragment MUC4-α-N-Ter. In certain embodiments the antibody binds to the MUC4 peptide fragment MUC4-α-C-Ter. In certain embodiments the antibody does not substantially bind the central tandom repeat (TR) domain of MUC4. In certain embodiments when an antibody does not substantially bind the central tandom repeat (TR) domain of MUC4 this indicates that the antibody has a binding affinity less than ($K_d$ greater than) about $10^{-4}$ M, preferably a $K_d$ greater than about $10^{-3}$ M, more preferably a $K_d$ greater than about $10^{-2}$ M. In certain embodiments when an antibody does not substantially bind the central tandom repeat (TR) domain of MUC4 this indicates that the antibody does not specifically bind the TR domain, and more preferably does not bind the TR domain. In certain embodiments antibody binds (e.g., specifically binds) to a cell that expresses a MUC4 protein (e.g., a cancer cell that expresses or overexpresses MUC4). In certain embodiments the antibody binds native MUC4 from human tissues and/or pancreatic cancer cells (e.g., in a Western blot, and/or in an immunochemistry assay, and/or using confocal analysis, and/or in a FACs system, etc.). In certain embodiments the cell is a cancer cell from a cancer selected from the group consisting of pancreatic cancer, gastric cancer, cervical cancer, and ovarian cancer. In certain embodiments the antibody binds (e.g., specifically binds) to a cancer cell in or on a primary tumor, and/or to a cancer cell in or on a solid tumor, and/or to a metastatic cell. In certain embodiments the antibody binds to a cancer cell in the lymph or blood. In certain embodiments the antibody is a monoclonal antibody or a fragment thereof. In certain embodiments the antibody is an IgG or a fragment thereof, or an IgM or a fragment thereof. In certain embodiments the antibody is an antibody selected from the group consisting of a Fab, and a (Fab')$_2$. In certain embodiments the antibody is produced by immunization of a non-human mammal (e.g., a murine, a rabbit, etc.) with an antigen substantially comprising MUC4-α-N-Ter and/or MUC4-α-C-Ter. Substantially comprising in this context indicates that the referenced moiety (e.g., MUC4-α-N-Ter and/or MUC4-α-C-Ter) is the sole immunogenic component used in the immunization or is administered with one or more adjuvants, but still is a component to which an immune response will primarily be mounted thereby facilitating isolation of antibodies directed against that component. In certain embodiments the antibody is an antibody selected from the group consisting of an scFv, and an (ScFv')$_2$. In certain embodiments the antibody is a human antibody, a chimeric antibody, or a humanized antibody. In certain embodiments the antibody is a non-human antibody (e.g., a murine antibody, a rabbit antibody, a goat antibody, a non-human primate antibody, etc.).

In various embodiments the antibody is attached to an effector (e.g., a moiety that has a biological activity that is typically different than the anti-MUC4 antibody). In certain embodiments the effector comprises an effector selected from the group consisting of a cytokine, an epitope tag, a second antibody a detectable label, an anti-cancer drug, a delivery vehicle comprising an anti-cancer drug, a cytotoxin, a radionuclide, a prodrug, a viral particle, a radiosensitizer, and a chelate. In certain embodiments the effector comprises a cytokine selected from the group consisting of interleukin 2 (IL-2), interleukin 6 (IL-6), interleukin 7 (IL-7), interleukin 12 (IL-12), interleukin 10 (IL-10), interleukin 15 (IL-15), interleukin 17 (IL-17), interleukin 24 (IL-24), granulocyte-macrophage colony stimulating factor (GM-CSF), tumor necrosis factor (TNF), interferon (e.g., IFN-α, IFN-β, IFN-γ), TNF-related apoptosis inducing ligand (TRAIL), the Fas ligand (FasL), and/or active fragments thereof. In certain embodiments the effector comprises an epitope tag selected from the group consisting of biotin, avidin streptavidin, the DYKDDDDK (SEQ ID NO:4) peptide, c-myc, the FINK-1 carbohydrate epitope, the HA epitope, the HSV epitope, $His_4$, $His_5$, and $His_6$. In certain embodiments the effector comprises a cytotoxin selected from the group consisting pseudomonas exotoxin, ricin A chin, abrin A chain, modeccin A chain, alpha-sacrin, *Aleurites fordii* proteins, Dianthin proteins, PAP, PAPII, PAP-S, *Morodica charantia* inhibitor, curcin, crotin, *Saponaria officinalis* inhibitor, gelonin, mitogillin, restrictocin, phenomycin, neomycin, thymidine kinase, or cytotoxic fragments thereof. In certain embodiments the effector comprises a radionuclide selected from the group consisting of $^3$H, $^{125}$I, $^{35}$S, $^{14}$C, $^{32}$P, $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain embodiments the effector comprises an alpha emitter (e.g., bismuth 213). In certain embodiments the radionuclide (e.g., isotope) is attached to the antibody with a chelator. In certain embodiments the chelator comprises DOTA. In certain embodiments the antibody is attached to an effector that comprises a lipid or a liposome. In certain embodiments the antibody is attached to an anti-cancer drug or to a lipid, liposome, or delivery vehicle containing an anti-cancer drug. In certain embodiments the anti-cancer drug is a drug selected from the drugs listed in Table 3. In certain embodiments the anti-cancer drug is a drug selected from the group consisting of carboplatin (e.g., PARAPLATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the antibody is attached to an effector that comprises a second antibody. In certain embodiments the second antibody is an antibody the binds a different epitope on MUC4. In certain embodiments the second antibody is an antibody that binds an immune effector cell (e.g., a T cell, a dendritic cell, etc.). In certain embodiments the second antibody that binds a receptor selected from the group consisting of a T cell receptor, CD2, CD3, CD5b, CD16, CD28, CD32, and CD64. In certain embodiments the second antibody that binds a CD3. In certain embodiments the antibody is attached to a detectable label selected from the group consisting of a radioactive label, a PET label, an MRA label, and an X-ray opaque label.

In various embodiments pharmaceutical formulations are provided. In certain embodiments the formulations comprise a pharmaceutically acceptable excipient and an anti-MUC4α antibody as described herein (e.g., an antibody that specifically binds MUC4α N-ter (SEQ ID NO: 1) and/or MUC4α C-ter (SEQ ID NO: 2) or a fragment thereof (e.g., an immunogenic fragment thereof)). In certain embodiments the formulations comprise a pharmaceutically acceptable excipient and an antibody (e.g. an antibody that specifically binds MUC4α N-ter and/or MUC4α C-ter or a fragment thereof) attached to an effector (e.g., cytokine, an epitope tag, a second antibody a detectable label, an anti-cancer drug, a delivery vehicle comprising an anti-cancer drug, a cytotoxin, a radionuclide, a prodrug, a viral particle, a radiosensitizer, a chelate, etc.) as described herein. In certain embodiments the formulation is a unit dosage formulation. In certain embodiments the excipient in the formulation(s) is suitable for administration via a route selected from the group consisting of parenterally, oral administration, nasal administration, rectal administration, intraperitoneal injection, and intravascular injection, subcutaneous injection, transcutaneous administration, intramuscular injection, application to a surgical site, implantable depot administration, and via a drug delivery pump. In certain embodiments the formulation further comprises an additional anti-cancer drug. In certain embodiments the anti-cancer drug is a drug selected from the drugs listed in Table 3. In certain embodiments the anti-cancer drug is a drug selected from the group consisting of carboplatin (e.g., PARAPLATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

In various embodiments methods method of inhibiting the growth or proliferation of a neoplastic cell that expresses MUC4 are provided. In certain embodiments the methods comprise contacting the neoplastic cell with an anti-MUC4α antibody described herein in an amount sufficient to inhibit growth or proliferation of the cell (e.g., to induce apoptosis, cytotoxicity, and/or cytostasis, etc.). In certain embodiments the methods comprise contacting the cell with an anti- MUC4α antibody described herein attached to an effector where the effector is selected from the group consisting of a cytokine that induces an immune response directed to the cell, a second antibody that induces an immune response directed to the cell, a radionuclide that cytostatic or cytotoxic to the cell, a radiosensitizer, a prodrug, a chelate comprising a drug or radionuclide that is cytotoxic or cytostatic to the cell, an anti-cancer drug, and a lipid, liposome, or polymeric particle comprising an anti-cancer drug, where the antibody attached to an effector is in an amount sufficient to inhibit growth or proliferation of the cell (e.g., to induce apoptosis, cytotoxicity, and/or cytostasis, etc.). In certain embodiments the methods comprise contacting the neoplastic cell with an anti-MUC4α antibody described herein attached to an effector where the effector comprises an epitope tag and then contacting the epitope tag with a second construct comprising a binding partner for the effector attached to a moiety selected from the group consisting of a cytokine that induces an immune response directed to the cell, a second antibody that induces an immune response directed to the cell, a radionuclide that cytostatic or cytotoxic to the cell, a radiosensitizer, a prodrug, a chelate comprising a drug or radionuclide that is cytotoxic or cytostatic to the cell, an anti-cancer drug, and a lipid, liposome, or polymeric particle comprising an anti-cancer drug, where second construct is in an amount sufficient to inhibit growth or proliferation of the cell (e.g., to induce apoptosis, cytotoxicity, and/or cytostasis, etc.) and the second construct binds to the epitope tag thereby associating the second construct with the neoplastic cell. In certain embodiments the epitope tag selected from the group consisting of biotin, avidin streptavidin, the DYKDDDDK (SEQ ID NO:5) peptide, c-myc, the HNK-1 carbohydrate epitope, the HA epitope, the HSV epitope, $His_4$ (SEQ ID NO:5), $His_5$ (SEQ ID NO: 6), $His_6$ (SEQ ID NO:7), and the like. In certain embodiments the effector or the moiety comprises a cytokine. In certain embodiments the cytokine is a cytokine selected from the group consisting of interleukin 2 (IL-2), interleukin 6 (IL-6), interleukin 7 (IL-7), interleukin 12 (IL-12), interleukin 10 (IL-10), interleukin 15 (IL-15), interleukin 17 (IL-17), interleukin 24 (IL-24), granulocyte-macrophage colony stimulating factor (GM-CSF), tumor necrosis factor (TNF), interferon (e.g., IFN-α, IFN-β, IFN-γ), TNF-related apoptosis inducing ligand (TRAIL), the Fas ligand (FasL), and/or active fragments thereof. In certain embodiments the effector or the moiety comprises a cytotoxin. In certain embodiments the cytotoxin is a cytotoxin selected from the group consisting pseudomonas exotoxin, ricin A chin, abrin A chain, modeccin A chain, alpha-sacrin, *Aleurites fordii* proteins, Dianthin proteins, PAP, PAPII, PAP-S, *Morodica charantia* inhibitor, curcin, crotin, *Saponaria officinalis* inhibitor, gelonin, mitogillin, restrictocin, phenomycin, neomycin, thymidine kinase, or cytotoxic fragments thereof. In certain embodiments the effector or the moiety comprises a radionuclide (e.g. $^3H$, $^{125}I$, $^{35}S$, $^{14}C$, $^{32}P$, $^{99}Tc$, $^{203}Pb$, $^{67}Ga$, $^{68}Ga$, $^{72}As$, $^{111}In$, $^{113m}In$, $^{97}Ru$, $^{62}Cu$, $^{64}1Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{177}Lu$, $^{105}Rh$, and $^{111}Ag$, and the like). In certain embodiments the effector or the moiety comprises, where the effector comprises an alpha emitter. In certain embodiments the radionuclide is attached to the antibody with a chelator. In certain embodiments the effector or the moiety comprises a lipid, a liposome, or a polymeric particle containing an anticancer drug. In certain embodiments the anti-cancer drug is a drug selected from the drugs listed in Table 3. In certain embodiments the anti-cancer drug is a drug selected from the group consisting of carboplatin (e.g., PARAPLATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the effector or the moiety comprises a second antibody. In certain embodiments the second antibody is an antibody that binds an immune effector cell (e.g., a T cell, a dendritic cell, etc.). In certain embodiments the second antibody binds a receptor selected from the group consisting of a T cell receptor, CD2, CD3, CD5b, CD16, CD28, CD32, and CD64. In various embodiments the (neoplastic) cell is a metastatic cell. In certain embodiments the cell is a solid tumor cell. In certain embodiments the cell is a cancer stem cell. In certain embodiments the cell is a cancer cell selected from the group consisting of a pancreatic cancer cell, a lung cancer cell, a breast cancer cell, a gall bladder cancer cell, a salivary gland cancer cell, a prostate cancer cell, a biliary tract cancer cell, a cervical cancer cell, and an ovarian cancer cell. In certain embodiments the cell is a cancer cell selected from the group consisting of an extra hepatic bile duct carcinoma cell, a colangiocarcinoma cell, a cutaneous squamous cell carcinoma, and a pancreatic cancer cell. In certain embodiments the cell is a pancreatic cancer cell. In certain embodiments the cell is an ovarian cancer cell. In certain embodiments the contacting comprises administering the antibody and/or the antibody attached to an effector to a human or to a non-human mammal. In certain embodiments the administering comprises administering via a route selected from the group consisting of parenterally, oral administration, nasal administration, rectal administration, intraperitoneal injection, and intravascular injection, subcutaneous injection, transcutaneous administration, intramuscular injection, application to a surgical site, implantable depot administration, and via a drug delivery pump. In certain embodiments the administering comprises administering into a tumor and/or into a surgical site. In certain embodiments the antibody and/or the antibody attached to an effector is formulated for administering via a route selected from the group consisting of parenterally, oral administration, nasal administration, rectal administration, intraperitoneal injection, and intravascular injection, subcutaneous injection, transcutaneous administration, intramuscular injection, application to a surgical site, implantable depot administration, administration to a surgical cite, and administration via a drug delivery pump. In certain embodiments the administering comprises administering into a tumor and/or into a surgical site.

In various embodiments methods for the in vivo detection of a neoplastic cell that expresses or overexpresses MUC4 in a mammal are provided. The method typically involve administering to the mammal an anti-MUC4α antibody described herein attached to a detectable label; and/or administering to the mammal an anti-MUC4α antibody described herein attached to an epitope tag and administering a second construct to the mammal the second construct comprising a binding partner for the epitope tag attached to a detectable label; and detecting the presence and/or amount, and/or location of the detectable label where the presence and/or amount, and/or location is an indicator of the location and/or presence and/or mass of neoplastic cells. In certain embodiments the cell is a metastatic cell. In certain embodiments the cell is a solid tumor cell. In certain embodiments the cell is a cancer stem cell. In certain embodiments the cell is a cancer cell selected from the group consisting of a pancreatic cancer cell, a lung cancer cell, a breast cancer cell, a gall bladder cancer cell, a salivary gland cancer cell, a prostate cancer cell, a biliary tract cancer cell, a cervical cancer cell, and an ovarian cancer cell. In certain embodiments the cell is a cancer cell selected from the group consisting of an extra hepatic bile duct carcinoma cell, a colangiocarcinoma cell, a cutaneous squamous cell carcinoma, and a pancreatic cancer cell. In certain embodiments the cell is a pancreatic cancer cell. In certain embodiments the cell is an ovarian cancer cell. In certain embodiments the detectable label is selected from the group consisting of a radioactive label, a PET label, an MRA label, and an X-ray opaque label. In certain embodiments the detectable label is a radionuclide (e.g. $^{99}Tc$, $^{203}Pb$, $^{67}Ga$, $^{68}Ga$, $^{72}As$, $^{111}In$, $^{113m}In$, $^{97}Ru$, $^{62}Cu$, $^{641}Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{177}Lu$, $^{99m}Tc$, $^{105}Rh$, $^{111}Ag$ and the like). In certain embodiments the detectable label is selected from the group consisting of a gamma-emitter, a positron-emitter, an x-ray emitter, and an alpha emitter. In certain embodiments the detecting comprises external imaging. In certain embodiments the detecting comprises internal imaging. In certain embodiments the detecting comprises X-ray, and/or CAT scan, and/or MRI, and/or PET, and/or ultrasonography (e.g., standard ultrasonography, doppler ultrasonography, etc.), and the like. In certain embodiments the administering comprises administering the antibody and/or the antibody attached to an effector to a human or to a non-human mammal. In certain embodiments the administering comprises administering via a route selected from the group consisting of parenterally, oral administration, nasal administration, rectal administration, intraperitoneal injection, and intravascular injection, subcutaneous injection, transcutaneous administration, intramuscular injection, and application to a surgical site.

In various embodiments methods for the ex vivo detection of a neoplastic cell that expresses or overexpresses MUC4 in a mammal are provided. The methods typically involve contacting a sample derived from the mammal with an anti-MUC4α antibody described herein; and determining the presence or amount of the antibody associated with a cell or a cellular component in the sample, where the presence and amount of the antibody associated with a cell or a cellular component in the sample indicates the presence of a neoplastic cell that expresses or overexpresses MUC4 in the mammal. In certain embodiments the cell is a metastatic cell. In certain embodiments the cell is a solid tumor cell. In certain embodiments the cell is a cancer stem cell. In certain embodiments the cell is a cancer cell selected from the group consisting of a pancreatic cancer cell, a lung cancer cell, a breast cancer cell, a gall bladder cancer cell, a salivary gland cancer cell, a prostate cancer cell, a biliary tract cancer cell, a cervical cancer cell, and an ovarian cancer cell. In certain embodiments the cell is a cancer cell selected from the group consisting of an extra hepatic bile duct carcinoma cell, a colangiocarcinoma cell, a cutaneous squamous cell carcinoma, and a pancreatic cancer cell. In certain embodiments the cell is a pancreatic cancer cell. In certain embodiments the cell is an ovarian cancer cell. In certain embodiments the biological sample comprises a sample selected from the group consisting of whole blood, a blood fraction, saliva/oral fluid, urine, a tissue biopsy, pleural fluid, pericardial fluid, cerebral spinal fluid, and peritoneal fluid. In certain embodiments the biological sample comprises peripheral blood mononuclear cells. In certain embodiments the determining comprises detecting the formation of immune complexes by the antibody and a MUC4 by a method selected from the group consisting of labeled primary antibody detection, labeled secondary antibody detection, flow cytometric analysis, immunochemical detection, radioimmunoassay, fluorescent immunoassay, enzyme-linked immunoassay, immunohistochemistry, and immunoblot analysis. In certain embodiments the anti-MUC4α antibody is in solution. In certain embodiments the anti-MUC4α antibody is immobilized on a solid support. In certain embodiments the solid support is selected from the group consisting of filter paper, multiwell dishes, microchips, polymeric microparticles, test strips, derivatized magnetic particles, and the like. In certain embodiments the method comprises a component in a differential diagnosis for cancer.

Also provided are kits for detection of cells expressing or overexpressing MUC4. In certain embodiments the kits comprise an anti-MUC4 antibody described herein; and, optionally, a detectable label for detecting the antibody. In certain embodiments the kit further comprises reagents suitable for detecting MUC4-antibody immunocomplexes, if present in a biological sample. In certain embodiments a detectable label in the kit is provided attached to an antibody that binds to immunocomplexes formed between the anti-MUC4 antibody and MUC4. In certain embodiments the detectable label is attached to the anti-MUC4 antibody. In certain embodiments the anti-MUC4 antibody is in solution. In certain embodiments the anti-MUC4 antibody is immobilized on a solid support (e.g., filter paper, multiwell dishes, microchips, polymeric microparticles, test strips, derivatized magnetic particles, nanoparticles (including, but not limited to quantum dots), and the like). In certain embodiments the detectable label is a radioactive label or a fluorescent label. In certain embodiments detectable label is selected from the group consisting of fluorescein, rhodamine, phycoerythrin, biotin, and strepavidin.

In various embodiments methods of treating a cancer in a mammal are provided. The method typically involve performing a method described herein that utilizes an anti-MUC4 antibody or an effector attached to an anti-MUC4 antibody to detect a neoplastic cell in vivo on the mammal or receiving the results of such a method performed on the mammal; and/or a method described herein that utilizes an anti-MUC4 antibody or an effector attached to an anti-MUC4 antibody to detect a neoplastic cell in a biological sample from the mammal or receiving the results of such a method performed on a biological sample from the mammal; and when the method indicates the presence of neoplastic cells in the mammal, treating the mammal, or causing the mammal to be treated, to remove and/or to inhibit the growth or proliferation of the neoplastic cells. In certain embodiments the treating said mammal comprises surgically removing the cells. In certain embodiments the treating said mammal comprises performing radiotherapy or causing radiotherapy to be performed on the mammal to kill the neoplastic cells. In certain embodiments the treating said mammal comprises administering or causing to be administered to the mammal an anti-cancer drug. In certain embodiments the anti-cancer drug is a drug selected from the drugs listed in Table 3. In certain embodiments the anti-cancer drug is a drug selected from the group consisting of carboplatin (e.g., PARAPL-ATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the treating comprises administering or causing to be administered to the mammal an anti-MUC4 antibody. In certain embodiments the anti-MUC4 antibody is an anti-MUC4 antibody described herein. In certain embodiments the treating said mammal comprises administering or causing to be administered to the mammal an anti-MUC4 antibody attached to an effector that has immunnomodulatory, cytostatic, or cytotoxic activity. In certain embodiments the is selected from the group consisting of a cytokine that induces an immune response directed to the cell, a second antibody that induces an immune response directed to the cell, a radionuclide that cytostatic or cytotoxic to the cell, a radiosensitizer, a prodrug, a chelate comprising a drug or radionuclide that is cytotoxic or cytostatic to the cell, an anti-cancer drug, and a lipid, liposome, or polymeric particle comprising an anti-cancer drug. In certain embodiments the anti-MUC4 antibody is an anti-MUC4 antibody described herein.

DEFINITIONS

The term "treat" when used with reference to treating, e.g. a pathology or disease refers to the mitigation and/or elimination of one or more symptoms of that pathology or disease, and/or a reduction in the rate of onset or severity of one or more symptoms of that pathology or disease, and/or the prevention of that pathology or disease.

The terms "isolated", "purified", or "biologically pure" when referring to an isolated polypeptide refer to material that is substantially or essentially free from components that normally accompany it as found in its native state. With respect to nucleic acids and/or polypeptides the term can refer to nucleic acids or polypeptides that are no longer flanked by the sequences typically flanking them in nature. Chemically synthesized polypeptides are "isolated" because they are not found in a native state (e.g. in blood, serum, etc.). In certain embodiments, the term "isolated" indicates that the polypeptide is not found in nature.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose α carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes whole antibodies, antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) Protein Eng. 8: 1323-1331), and in addition to monospecific antibodies, also include bispecific, trispecific, quadraspecific, and generally polyspecific antibodies (e.g., bs scFv).

The term "antigen-binding portion" of an antibody (or simply "antibody portion"), as used herein, refers to one or more fragments of an antibody that retain the ability to specifically bind to an antigen (e.g., MUC4α N-ter and/or MUC4α C-ter or fragment(s) thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including $V_H$ and $V_L$ domains; (vi) a dAb fragment (Ward et al. (1989) Nature 341, 544-546), which consists of a $V_H$ domain; (vii) a dAb which consists of a $V_H$ or a $V_L$ domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, a monoclonal antibody of the invention is of the IgG1 isotype. In other embodiments, a monoclonal antibody of the invention is of the IgG2 isotype.

The term "bispecific antibody" as used herein refers to an antibody comprising two antigen-binding sites, a first binding site having affinity for a first antigen or epitope and a second binding site having binding affinity for a second antigen or epitope distinct from the first.

The phrase "specifically target/deliver" when used, for example with reference to a chimeric moiety of this invention refers to specific binding of the moiety to a target (e.g., a cell overexpressing the target protein(s)) this results in an increase in local duration and/or concentration of the moiety at or within the cell as compared to that which would be obtained without "specific" targeting. The specificity need not be absolute, but simply detectably greater/measurably avidity/affinity than that observed for a cell expressing the target protein(s) at normal (e.g., wildtype) or than that observed for a cell that does not express the target protein(s).

An "isolated antibody" refers to an antibody that at some time has existed outside an animal typically a mammal. Thus "isolated" excludes naturally occurring antibodies that have existed only in vivo. Alternatively, this term may refer to an antibody that has been sufficiently separated from other proteins or other biomolecules with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example pharmaceutically acceptable preparations.

The term "anti-cancer drug" is used herein to refer to one or a combination of drugs conventionally used to treat cancer. Such drugs are well known to those of skill in the art and include, but are not limited to doxirubicin, vinblastine, vincristine, taxol, etc.

The term "nanoparticle" refers to a particle having a submicron (µm) size. In various embodiments, microparticles have a characteristic size (e.g., diameter) less than about 1 µm, 800 nm, or 500 nm, preferably less than about 400 nm, 300 nm, or 200 nm, more preferably about 100 nm or less, about 50 nm or less or about 30 or 20 nm or less.

The term "microparticle" refers to a particle having a characteristic size of between about 1 µM and 100 µM.

In certain embodiments, conservative substitutions of the amino acids comprising any of the antibody sequences, especially CDR regions of such sequence sequences described herein are contemplated. In various embodiments one, two, three, four, or five different residues are substituted. The term "conservative substitution" is used to reflect amino acid substitutions that do not substantially diminish the activity (e.g., MUC4α N-ter and/or MUC4α C-ter affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W).

"Binding" or "specific binding" are used interchangeably herein and indicates that an antibody exhibits substantial affinity for a specific molecule (e.g., MUC4α N-ter and/or MUC4α C-ter or fragment(s) thereof) or a cell or tissue bearing the molecule and is said to occur when the antibody or a chimeric moiety comprising the antibody has a substantial affinity for the specific molecule and is selective in that it does not exhibit significant cross-reactivity with other molecules. Preferred substantial binding includes binding with a dissociation constant ($K_d$) of $10^{-6}$, $10^{-7}$, $10^{-8}$, $10^{-9}$, $10^{-10}$, $10^{-11}$, $10^{-12}$ M. or better. For example, the iQ of an antibody-antigen interaction indicates the concentration of antibody (expressed as molarity) at which 50% of antibody and antigen molecules are bound together at thermodynamic equilibrium. Thus, at a suitable fixed antigen concentration, 50% of a higher (i.e., stronger) affinity antibody will bind antigen molecules at a lower antibody concentration than would be required to achieve the same percent binding with a lower affinity antibody. IQ is also the ratio of the kinetic on and off rates ($k_{on}$ and $k_{off}$); i.e., $k_d = k_{off}/k_{on}$. Thus, a lower $K_d$ value indicates a higher (stronger) affinity. As used herein, "better" or "higher" affinities are stronger affinities, and are identified by dissociation constants of lower numeric value than their comparators, with a $K_d$ of $10^{-10}$ M being of lower numeric value and therefore representing a better affinity than an IQ of $10^{-9}$M. Affinities better (e.g., with a lower IQ value and therefore stronger) than $10^{-7}$M, preferably better than $10^{-8}$M, are generally preferred. Values intermediate to those set forth herein are also contemplated, and preferred binding affinity can be indicated as a range of dissociation constants, for example preferred binding affinities for antibodies disclosed herein are represented by $K_d$ values ranging from $10^{-6}$ to $10^{-12}$ M (i.e., micromolar to picomolar), preferably $10^{-7}$ to $10^{-12}$ M, more preferably $10^{-7}$ to $10^{-12}$ M or better. An antibody that "does not exhibit significant cross-reactivity" is one that will not appreciably bind to an off-target antigen. For example, in one embodiment, an antibody that specifically and selectively binds to cardiac myosin will exhibit at least a two, and preferably three, or four or more orders of magnitude better binding affinity (i.e., binding exhibiting a two, three, or four or more orders of magnitude lower IQ value) for cardiac myosin than for myosin molecules other than cardiac myosin or for non-myosin proteins or peptides. Binding affinity and selectivity can be determined using any art-recognized methods for determining such characteristics, including, for example, using Scatchard analysis and/or competitive (competition) binding assays.

Binding may be assessed, and $K_d$ values determined, using any of a variety of techniques that are well known in the art. For example, binding to an MUC4α N-ter and/or MUC4α C-ter or fragment(s) thereof can assessed by coating an appropriate solid support (e.g., beads, ELISA plate or BIACORE chip) with MUC4α N-ter and/or MUC4α C-ter or fragment(s) thereof. Target specific, dose-dependent binding of the antibody of interest is then assessed by measuring the amount of antibody binding to target versus controls as a function of increasing dose using standard protocols corresponding to the solid support and binding technology being used. Representative such protocols include those described in Wassaf et al. (2006) *Anal. Biochem.* 351(2):241-53; Epub 2006 Feb. 10 (BIACORE); and Murray and Brown (1999) *J. Immunol. Meth.* 127(1): 25-28 (ELISA). In addition, studies that vary the amount of immobilized target molecule or that include increasing levels of soluble target molecule as a competitor may also be performed to monitor binding and specificity.

In certain embodiments, the IQ is determined using a biosensor (e.g., by surface plasmon resonance (e.g., BIAcore) or resonant mirror analysis (IAsys)). Such determinations may be performed as described by Hefta et al., *Measuring Affinity Using Biosensors*, in "Antibody Engineering: A Practical Approach," McCafferty et al. (eds), pp. 99-116 (Oxford University Press, 1996), and references cited therein. Briefly, kinetic on and off rates (k- and $k_{off}$) can be determined using a sensor chip to which the MUC4α N-ter (SEQ ID NO: 1) and/or MUC4α C-ter (SEQ ID NO: 2) or fragment(s) thereof has been coupled. To evaluate association ($k_{on}$), solutions of different concentrations of antibody (or chimeric moiety comprising an antibody) flow across the chip while binding is monitored using mass sensitive detection. Using the BIAcore system (GE Healthcare; Piscataway, N.J.), $k_{on}$ is the slope of the plot of dR/dt versus R, where R is the signal observed. Following binding, dissociation is observed by passing a buffer solution across the chip, and $k_{off}$ is determined in an analogous fashion. $K_d$ is then calculated using the equation: $K_d = k_{off}/k_{on}$.

The antibodies contemplated herein also encompass "conservative amino acid substitutions" in the sequences of the antibodies described herein that do not abrogate the binding of the antibody to MUC4α N-ter and/or MUC4α C-ter. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (H is, Arg, Lys); Class V (Ile, Leu, Val, Met); and Class VI (Phe, Tyr, Tip). For example, substitution of an Asp for another class III residue such as Asn, Gln, or Glu, is a conservative substitution. Thus, a predicted nonessential amino acid residue in an anti-MUC4α N-ter and/or anti-MUC4α C-ter antibody is preferably replaced with another amino acid residue from the same class. Methods of identifying amino acid conservative substitutions that do not eliminate antigen binding are well-known in the art (see, e.g., Brummell et al. (1993) *Biochem.* 32: 1180-1187; Kobayashi et al. (1999) *Protein Eng.* 12(10): 879-884); and Burks et al. (1997) *Proc. Natl. Acad. Sci. USA* 94: 412-417, and the like).

The terms "treat," "treating," and "treatment," as used herein, refer to therapeutic or preventative measures described herein. The methods of "treatment" employ administration to a subject, an antibody or antigen binding portion of the present invention, for example, a subject having a cancer/neoplasias characterized by upregulation of MUC4 or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer treated or diagnosed using the methods of the present invention is selected from pancreatic cancer, lung cancer, breast cancer, gall bladder cancer, salivary gland cancer, prostate cancer, biliary tract cancer, cervical cancer, and ovarian cancer.

The term "effective amount," as used herein, refers to that amount of an antibody or an antigen binding portion thereof that binds MUC4α N-ter and/or MUC4α C-ter, or a chimeric moiety comprising such an antibody, that is sufficient to effect treatment, prognosis or diagnosis of a disease (e.g., a cancer) associated with upregulation of MUC4, as described herein, when administered to a subject. A therapeutically effective amount will vary depending upon the subject and particular cancer condition being treated, the weight and age of the subject, the severity of the disease condition, the manner of administration and the like, which can readily be determined by one of ordinary skill in the art. In certain embodiments the dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, according to the invention. Dosage regimen may be adjusted to provide the optimum therapeutic response. An effective amount is also one in which any toxic or detrimental effects (e.g., side effects) of an antibody or antigen binding portion thereof are minimized and/or outweighed by the beneficial effects. Additional preferred dosages regimens are described further below in the section pertaining to pharmaceutical compositions.

The terms "patient" and "subject" are used interchangeably. The term "patient" includes human and other mammalian subjects that receive either prophylactic or therapeutic treatment. The "subject" includes any human or non-human animal. For example, the methods and compositions of the present invention can be used to treat a subject having cancer. In one particular embodiment, the subject is a human. The term "non-human animal" includes all vertebrates, e.g., mammals and non-mammals, such as non-human primates, felines, canines, equines, bovines, largomorphs, and the like. Thus, veterinary as well as medical applications of the methods and compositions described herein are contemplated.

The terms "anti-cancer agent" and "antineoplastic agent" refer to drugs used to treat malignancies, such as cancerous growths. Drug therapy may be used alone, or in combination with other treatments such as surgery or radiation therapy. Several classes of drugs may be used in cancer treatment, depending on the nature of the organ involved. Anti-cancer agents contemplated herein include, among others, the agents shown in Table 3.

The term "biological sample" or "test sample" refers to sample is a sample of biological tissue, cells, or fluid that, in a healthy and/or pathological state, contains an analyte that is to be detected, e.g., a MUC4 protein, a cell bearing a MUC4 protein etc. Such samples include, but are not limited to sputum/oral fluid, amniotic fluid, blood, a blood fraction, or fine needle biopsy samples (e.g., surgical biopsy, fine needle biopsy, etc.) urine, peritoneal fluid, pleural fluid, and the like. Although the sample is typically taken from a human subject (e.g., patient), the assays can be used to detect cells expressing MUC4 antibodies in samples from any mammal, such as dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, inactivation of interfering components, the addition of reagents, lysing, etc. If such methods of pretreatment are employed with respect to the sample, such pretreatment methods are typically such that the analyte of interest (e.g., MUC4 or cells expressing MUC4) remains in the test sample, preferably at a concentration proportional to that in an untreated test sample (e.g., namely, a sample that is not subjected to any such pretreatment method(s)). Such "treated" or "processed" samples are still considered to be biological samples with respect to the methods described herein.

The term "blood" includes whole blood, or blood fractions such as serum or plasma.

By "diagnostic test" is meant any kind of medical test performed to aid in the diagnosis or detection of disease and/or pathology.

BRIEF DESCRIPTION OF THE DRAWINGS

FIGS. 1A and 1B show the amino acid sequences for MUC4α N-Ter (SEQ ID NO:1) (FIG. 1A) and for MUC4α C-Ter (SEQ ID NO:2) (FIG. 1B).

FIG. 2A: Schematic structure of MUC4 and recombinant proteins used in the study. MUC4 is putatively cleaved at the GDPH site to generate an N-terminal mucin-type subunit MUC4-α and a C-terminal growth factor-type subunit MUC4-β. Important domains of MUC4 are marked. Recombinant domains of MUC4-a corresponding to the fragments upstream and downstream of the tandem-repeat (TR) domain were cloned and expressed as described in Materials and Methods in Example 1 and termed MUC4-α-N-ter and MUC4-α-C-Ter, respectively. The nucleotide numbers corresponding to the boundaries of the recombinant domains are marked and are described in Moniaux et al. (1999) *Biochem. J.* 338: 325-333 and Choudhury et al. (2000) *J. Biochem. (Tokyo)*, 128: 233-243 according to the original numbering. Cys-cystein-rich domain EGF-epidermal growth factor-like domain; TM-transmembrane domain; CT-cytoplasmic tail. FIG. 2B: ELISA showing the reactivity of anti-MUC4 MAbs to recombinant immunogens. The indicated MAbs were incubated with the 2.5 mg/ml of GST-tagged N-terminal and tandem repeat recombinant domains of MUC4. The specificities were also tested against the MUC4 TR peptide, GST and a non-specific control protein bovine serum albumin and the antibodies exhibited negative reactivity against these antigens. The assay also included a non-specific isotype matched control K2G6

FIG. 8A: Western blot analysis of MUC4 expression and its derived sub lines SKOV3 Vec (empty vector p-SecTaq) and SKOV3 MUC4. A total of 20 µg protein from cell extracts was resolved by electrophoresis on a 2% SDS-agarose gel for MUC4 and 10% SDS-PAGE for HER2, transferred to polyvinylidene difluoride membrane, and incubated with anti-MUC4 monoclonal antibody. The membrane was then probed with horseradish peroxidase-labeled goat anti-mouse immunoglobulin. The signal was detected using an electrochemiluminescence reagent kit. MUC4 mucin is a high molecular weight glycoprotein and the predicted size of the mini MUC4 protein is 320 kda. β-actin served as a loading control. FIG. 8B: Localization of MUC4 and HER2 by confocal microscopy in both the derived cells. Cells were grown at low density on sterilized cover slips, washed, and fixed in ice-cold methanol at −20° C. After blocking in 10% goat serum, cells were incubated with the anti-MUC4 mouse monoclonal and anti-HER2 rabbit polyclonal antibodies, washed, and followed by secondary incubation with FITC-conjugated goat anti-mouse IgG and anti-rabbit PI used for nuclear staining (Scale bar-20 µm).

FIGS. 9A and 9B illustrate cancer stem cell population analysis in MUC4 overexpressed cells. FIG. 9A: Hoechest33342 dye analysis showed an increased (0.1%) side population (SP) in SKOV3-MUC4 cells compared to SKOV3-Vector cells. FIG. 9A: FACS analysis of the CD133-positive population showed an enriched cancer stem cell population (0.1%) in MUC4-transfected SKOV3 cells compared to vector-transfected cells.

FIG. 11A: Confocal analysis showed significant expression of CD133 in isolated colonies compared to SKOV3-MUC4 cells. MUC4 expression was seen in both isolated colonies and SKOV3-MUC4 cells. DAPI was used as nuclear counter staining FIG. 11B: Western blot analysis showed MUC4, HER2, ALDH1, CD133 and Shh expression in SKOV3-MUC4 and isolated colonies from MUC4 overexpressed SKOV3 cells. b-actin served as a loading control. DIC—differential interference contrast and staining (Scale bar-20 µm).

DETAILED DESCRIPTION

Figure 2A:
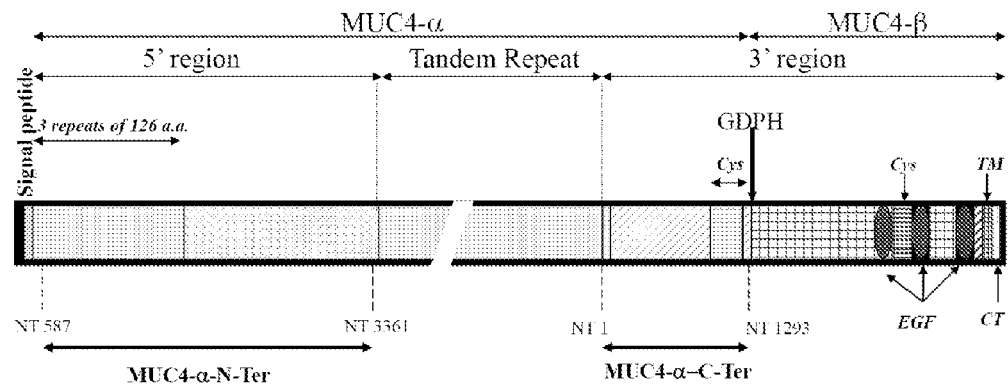
FIGS. 2A and 2B show a schematic structure of the recombinant MUC4 domains and reactivity of various anti-MUC4 antibodies.

In various embodiments improved antibodies that specifically bind human MUC 4 are provided. These antibodies and conjugates comprising these antibodies find use in the detection/diagnosis and treatment of cancers, particular cancers characterized by upregulation of MUC4.

Human MUC4 is a highly glycosylated membrane-associated mucin, consisting of a large 850-kD mucin-like subunit MUC4α, and a membrane-bound 80 kD growth factor-like subunit MUC4β (Moniaux et al. (1999) *Biochem. J.* 338: 325-333; Chaturvedi et al. (2008) *FASEB J.*, 22: 966-981). MUC4α contains a central tandem repeat (TR) domain containing variable numbers of 16 amino-acid residue motifs that can be repeated up to 400 times per molecule. The TR domain is flanked by a C-terminal cysteine rich domain and an N-terminal domain which contains three repeats of 123 amino acid residues (Moniaux et al. (1999) *Biochem. J.* 338: 325-333). MUC4β contains a cysteine rich domain, a domain rich in N-glycosylation sites and three EGF-like domains (Id.). MUC4 is considered to be a human homologue of rat sialomucin complex (SMC, rat Muc4) because of similarities in structural organization (Moniaux et al. (1999) *Biochem. J.* 338: 325-333; Sheng et al. (1992) *J. Biol. Chem.,* 267: 16341-16346; Wu et al. (1994) J. Biol. Chem., 269: 11950-11955). SMC is a heterodimeric glycoprotein composed of an O-glycosylated mucin subunit, ascites sialoglycoprotein (ASGP-1), tightly bound to a N-glycosylated transmembrane subunit, ASGP-2, which contains two epidermal growth factor-like domains in its extracellular part (Sheng et al. (1992) *J. Biol. Chem.,* 267: 16341-16346; Wu et al. (1994) *J. Biol. Chem.,* 269: 11950-11955). MUC4 is expressed in various epithelial tissues, including the epithelia of fetal lungs and the adult respiratory tract from the trachea to the collecting ducts lung trachea (Copin et al. (2000) *Int. J. Cancer,* 86: 162-168), colon (Ogata et al. (1992) *Cancer Res.,* 52: 5971-5978), endocervix (Gipson (2001) *Front Biosci.* 6: D1245-D1255), conjunctiva (Inatomi et al. (1996) *Invest. Ophthalmol. Vis. Sci.* 37: 1684-1692), cornea (Corrales et al. (2003) *Curr. Eye Res.* 27: 323-328), salivary glands (Liu et al. (2002) *J. Histochem. Cytochem.* 50: 811-820), middle ear and eustachian tube (Lin et al. (2001) *Am. J. Physiol. Lung Cell Mol. Physiol.,* 280: L1157-L1167). In recent studies, a progressive increase in MUC4 expression has been observed in pancreatic intraepithelial neoplastic lesions, indicating its role in disease development (Swartz et al. (2002) *Am. J. Clin. Pathol.,* 117: 791-796).

Previous studies from our laboratory have shown that inhibition of MUC4 expression using anti-sense or short-interfering RNA (siRNA) oligonucleotides specific to MUC4 results in a decreased tumorigenicity and dissemination of cancer cells (Singh et al. (2004) *Cancer Res.,* 64: 622-630). Further, our recent studies have demonstrated that MUC4 results in oncogenic transformation of mouse fibroblasts (Bafna et al. (2008) *Cancer Res.,* 68: 9231-9238), contributes to the drug-resistance of pancreatic cancer cells by activating anti-apoptotic pathways (Bafna et al. (2009) *Br. J. Cancer,* 101: 1155-1161), and is involved in the epithelial-to-mesenchymal transition in ovarian cancer cells (Ponnusamy et al. (2010) *Oncogene,* 29(42): 5741-5754). These studies from our laboratory indicate the importance of this mucin in various aspects of tumor biology.

We have previously generated a panel of monoclonal antibodies directed against the TR region of MUC4 (Moniaux et al. (2004) J. Histochem. Cytochem., 52: 253-261). One of the anti-MUC4 TR antibodies, 8G7, has served as a valuable reagent to study the expression of the MUC4 mucin in various tissues and unravel its involvement in various malignancies including, pancreatic (Swartz et al. (2002) *Am. J. Clin. Pathol.,* 117: 791-796; Jhala et al. (2006) *Am. J. Clin. Pathol.,* 126: 572-579), gastric (Senapati et al. (2008) *Br. J. Cancer,* 99: 949-956), cervical (Munro et al. (2009) *Int. J. Gynecol. Pathol.* 28(2): 127-133), ovarian cancers (Chauhan et al. (2006) *Mod. Pathol.,* 19: 1386-1394), extra hepatic bile duct carcinoma (Tamada et al. (2006) *Clin. Cancer Res.,* 12: 4257-4264), colangiocarcinoma (Shibahara et al. (2004) *Hepatology* 39: 220-229), and cutaneous squamous cell carcinoma.

MUC4 contains many structural and functional domains both upstream and downstream of the TR region (Moniaux et al. (1999) *Biochem. J.* 338: 325-333; Chaturvedi et al. (2008) *FASEB J.,* 22: 966-981), and many spliced forms of MUC4 are completely devoid of TR region (Choudhury et al. (2000) *J. Biochem.* (Tokyo), 128: 233-243; Moniaux et al. (2000) *Eur. J. Biochem.,* 267: 4536-4544). Further, the TR region is heavily O-glycosylated. Given the alteration in glycosylation status of solid tumors, it is possible that reactivity to the antibody can be obscured in certain malignancies.

In view of the structural complexity of MUC4, the existence of numerous splice variants and glycoforms, and heavy O-glycosylation in the TR domain we generated additional antibodies to fully understand the structure-function relationship of various MUC4 domains under physiological and pathological conditions. Here, we report the generation and characterization of a novel anti-MUC4 antibodies (e.g., monoclonal antibodies) that recognize the regions of MUC4α both upstream and downstream of the TR domain.

Purified recombinant MUC4 fragments, fused in frame with GST, were used as immunogens and positive clones were selected based on their reactivity in ELISA. Selected clones were characterized by their reactivity toward MUC4 in immunoblotting, immunoprecipitation, immunofluorescence and flow cytometry using pancreatic cancer cells. It was a surprising discovery that antibodies that do not bind the TR domain of MUC4 are capable of specifically binding native MUC4 in an isolate and when displayed on a cell (e.g., a cancer cell). Thus, it is believed that non-TR anti-MUC4 antibodies described herein are reagents for use in assays for quantification of MUC4 in tissues and biological fluids (e.g., biological samples) to diagnose the presence of a neoplastic cell, and/or for use in vivo to detect and/or to localize, and/or to image the size/mass of a cancer that expresses MUC4.

In addition, without being bound to a particular theory, it is believed that anti-MUC4 antibodies, particularly antibodies that do not bind the TR domain (e.g., that bind upstream and/or downstream from the TR domain) are effective in the treatment of cancers characterized by the upregulation of MUC4. Thus, for example, such antibodies can be used to inhibit the growth and/or proliferation of neoplastic cells that upregulate MUC4 and/or that kill such cells.

I. Antibodies that Bind the Non-TR Domain(s) of Human MUC4.

A) Anti-MUC4α Antibodies and Preparation Methods.

In various embodiments antibody are provided that bind the non-TR domains of human MUC4. In certain embodiments the antibodies include polyclonal antibodies, monoclonal antibodies (including, but not limited to IgG, IgA, IgM isotypes). In addition antibodies existing in a variety of other forms including, for example, Fv, Fab, and (Fab')$_2$, as well as bi-functional (e.g., bi-specific) hybrid antibodies single chains antibodies and the like are contemplated.

In certain embodiments antibodies that have a binding affinity ($K_d$) for MUC4α N-ter and/or MUC4α C-ter of at least about $10^{-6}$ M, or at least about $10^{-7}$ M, or at least about $10^{-8}$ M, or at least about $10^{-9}$ M, or at least about $10^{-10}$ M, or at least about $10^{-11}$ M, or at least about $10^{-12}$ M, or at least about $10^{-13}$ M are contemplated.

1) Antigen Preparation.

In general, antibodies that bind the no-TR domains of human MUC4 can be generated using and an antigen regions of MUC4α on either side of the TR domain (e.g. as described in Example 1). Regions on either side of the TR domain are cloned and expressed and proteins are purified using standard methods well known to those of skill in the art.

In one illustrative, but non-limiting embodiment, regions of MUC4-α on either side of the TR domain are cloned and expressed, and purified proteins are used as immunogens. As described in example 1, specific primers are designed using MUC4 sequence AJ000281 to amplify the fragments from nucleotides 587 to 3361 [MUC4α-Amino Terminal (MUC4α

N-ter)] and from nucleotides 1 to 1293 [MUC4α-carboxy terminal (MUC4α C-ter), representing the regions immediately upstream and downstream of the TR domain, respectively (see, e.g., FIG. 2A).

While, in certain embodiments, full length MUC4α N-ter and MUC4α C-ter domains are used to raise (and/or to select) antibodies, shorter fragments are also contemplated. In various embodiments shorter fragments still comprise a sufficient number of contiguous amino acids that the protein is immunogenic and/or such that the protein can be specifically recognized by an antibody. Typically the fragments comprise at least 10 contiguous amino acids, preferably at least 12 or 15 contiguous amino acids more preferably 20, or 25, or 30 contiguous amino acids of MUC4α N-ter and/or MUC4α C-ter.

Restriction sites (e.g., BamHI and an EcoRI restriction site) can be added in the forward and reverse primers, respectively, allowing in-frame cloning, for example with the GST and thrombin cleavage site of the pGEX-2TK vector (Pharmacia). Amplification can be done by the expand long RT-PCR system (Roche) as described previously using JER103 and JER109 as templates for sequence AJ00281 and AJ010901, respectively (see, e.g., Moniaux et al. (1999) *Biochem. J.* 338: 325-333). The constructs can be sequenced confirm the proper reading frame and can be maintained for example, in *E. coli* BL21 (New England Biolabs Inc.).

A method for obtaining an antibody using MUC4α N-ter and/or MUC4α C-ter or fragment(s) thereof as an antigen is not particularly limited, provided that such method can produce an antibody that specifically binds a non-TR domain of MUC4α.

2) Polyclonal Antibody Preparation.

In one illustrative embodiment, or fragment(s) thereof bound to or polymerized with proteins such as KLH (keyhole limpet hemocyanin), BSA (bovine serum albumin), or OVA (ovalbumin), or polymers, as carriers, are can be used as immunizing antigens, although such carriers are not necessarily required. In certain embodiments immunizing antigens may be prepared by mixing several types of antigens that have been prepared by different carrier-binding methods.

Animals to be immunized are not particularly limited, and suitable examples include, but are not limited to rabbits, goats, sheep, mice, rats, guinea pigs, and chickens, and the like. The animals are inoculated, e.g., subcutaneously, intramuscularly, or intraperitoneally with the immunizing antigen(s), that can be prepared by, for example, emulsifying the antigen(s) with the complete or incomplete Freund's adjuvant. In various embodiments inoculation is carried out every 2 to 5 weeks and continued until the antibody reactivity of the immunized animals with the inoculated antigen is sufficiently elevated. As long as the antibody reactivity of the immunized animals is sufficiently elevated, a dose of the antigen to be inoculated is not particularly limited. In various illustrative embodiments such dose ranges from about 1 to about 100 μg. In certain embodiments the immunization is repeated 3 to 20 times.

Blood, ascites, or other samples are extracted from the animals 7 to 10 days after the final immunization. In certain embodiments the immunized animals can be exsanguinated, and blood serum is prepared via centrifugation or other means.

The reactivity of the anti-MUC4 antibody contained in the blood serum may be analyzed any convenient method known to one of skill in the art. Examples of such methods include, but are not limited to ELISA assays, Western blotting, dot blotting, BiaCore analysis, and the like.

Antibodies can be separated and purified by conventional methods for separating and purifying immunoglobulin. Specific examples of such methods include salting out, alcohol precipitation, isoelectric precipitation, electrophoresis, adsorption ion exchangers, ultracentrifugation, gel filtration, and selective separation of specific antibodies via adsorption with the aid of an antigen-antibody conjugate or active absorbent.

The thus prepared antibody is typically a polyclonal antibody, which may be primarily composed of IgG and may contain other immunoglobulins such as IgM or IgA.

3) Monoclonal Antibody Production.

Monoclonal antibodies that bind the non-TR domain(s) of MUC4α can be produced using a variety of known techniques, such as the standard somatic cell hybridization technique described by Kohler and Milstein (1975) *Nature* 256: 495-497, viral or oncogenic transformation of B lymphocytes, or phage display technique using libraries of human antibody genes. In certain embodiments, the antibodies are fully human monoclonal antibodies.

Accordingly, in one embodiment, a hybridoma method is used for producing an antibody that binds MUC4α N-ter and/or MUC4α C-ter. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (see, e.g., Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (see, e.g., Goding, Monoclonal Antibodies: Principles and Practice, pp. 59-103 (Academic Press, 1986)). Suitable culture media for this purpose include, for example, D-MEM or RPMI-1640 medium.

In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another illustrative embodiment, antibodies and antibody portions that bind MUC4α N-ter and/or MUC4α C-ter can be isolated from antibody phage libraries generated using the techniques described in, for example, McCafferty et al. (1990) *Nature,* 348: 552-554, Clackson et al. (1991) *Nature,* 352: 624-628; Marks et al. (1991) *J. Mol. Biol.,* 222:581-597, Hoet et al. (2005) *Nature Biotechnology* 23: 344-348, U.S. Pat. Nos. 5,223,409; 5,403,484; and 5,571,698; 5,427,908, 5,580,717, 5,969,108, 6,172,197, 5,885,793, 6,521,404, 6,544,731, 6,555,313; 6,582,915, 6,593,081, and the like.

Additionally, production of high affinity (nM range) human antibodies by chain shuffling (Marks et al. (1992) *Bio/Technology,* 10:779-783, as well as combinatorial infection and in vivo recombination as a strategy for constructing very large phage libraries (Waterhouse et al. (1993) *Nuc. Acids. Res.,* 21: 2265-2266) may also be used.

In one particular embodiment, the monoclonal antibody or antigen binding portion thereof that binds MUC4α N-ter and/or MUC4α C-ter is produced using the phage display technique described by Hoet et al. (2005) *Nature Biotechnology* 23: 344-348. This technique involves the generation of a human Fab library having a unique combination of immunoglobulin sequences isolated from human donors and having synthetic diversity in the heavy-chain CDRs is generated. The library is then screened for Fabs that bind to MUC4α N-ter and/or to MUC4α C-ter.

In yet another embodiment, human monoclonal antibodies directed against MUC4α N-ter and/or MUC4α C-ter can be generated using transgenic or transchromosomic mice carrying parts of the human immune system rather than the mouse system (see e.g., Lonberg et al. (1994) *Nature* 368(6474): 856-859; Lonberg et al. (1994), supra; reviewed in Lonberg, (1994) *Handbook of Experimental Pharmacology* 113: 49-101; Lonberg and Huszar (1995) *Intern. Rev. Immunol.* 13: 65-93, and Harding and Lonberg (1995) *Ann. N.Y. Acad. Sci.* 764:536-546. See also U.S. Pat. Nos. 5,545,806; 5,569, 825; 5,625,126; 5,633,425; 5,789,650; 5,877,397; 5,661,016; 5,814,318; 5,874,299; 5,770,429; and 5,545,807, and PCT Publication Nos. WO 92/03918, WO 93/12227, WO 94/25585, WO 97/13852, WO 98/24884; WO 99/45962; and WO 01/14424.

In another embodiment, human antibodies that bind the non-TR domain(s) of human MUC4α can be raised using a mouse that carries human immunoglobulin sequences on transgenes and transchomosomes, such as a mouse that carries a human heavy chain transgene and a human light chain transchromosome (see e.g., PCT Publication WO 02/43478).

Alternative transgenic animal systems expressing human immunoglobulin genes are available in the art and can be used to raise antibodies that bind MUC4α N-ter and/or MUC4α C-ter. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and can be used to raise antibodies to MUC4α N-ter and/or MUC4α C-ter. For example, mice carrying both a human heavy chain transchromosome and a human light chain tranchromosome can be used; as described in Tomizuka et al. (2000) *Proc. Natl. Acad. Sci. USA* 97: 722-727. Cows carrying human heavy and light chain transchromosomes have been described in the art (Kuroiwa et al. (2002) *Nature Biotechnology* 20: 889-894) and can be used to raise antibodies to MUC4α N-ter and/or MUC4α C-ter.

In yet another embodiment, antibodies that bind MUC4α N-ter and/or MUC4α C-ter can be prepared using a transgenic plant and/or cultured plant cells (such as, for example, tobacco, maize and duckweed) that produce such antibodies. For example, transgenic tobacco leaves expressing antibodies or antigen binding portions thereof can be used to produce such antibodies by, for example, using an inducible promoter (see, e.g., Cramer et al. (1999) *Curr. Top. Microbol. Immunol.* 240: 95 118). Also, transgenic maize can be used to express such antibodies and antigen binding portions thereof (see, e.g., Hood et al. (1999) *Adv. Exp. Med. Biol.* 464: 127 147). Antibodies can also be produced in large amounts from transgenic plant seeds including antibody portions, such as single chain antibodies (scFv's), for example, using tobacco seeds and potato tubers (see, e.g., Conrad et al. (1998) *Plant Mol. Biol.* 38: 101 109). Methods of producing antibodies or antigen binding portions in plants can also be found in, e.g., Fischer et al. (1999) *Biotechnol. Appl. Biochem.* 30: 99 108, Ma et al. (1995) *Trends Biotechnol.* 13: 522-527; Ma et al. (1995) *Plant Physiol.* 109: 341-346; Whitelam et al. (1994) *Biochem. Soc. Trans.* 22: 940-944, and U.S. Pat. Nos. 6,040, 498 and 6,815,184.

In various embodiments the binding specificity of monoclonal antibodies or portions thereof that bind MUC4α N-ter and/or MUC4α C-ter prepared using any technique including those disclosed here, can be determined by immunoprecipitation or by an in vitro binding assay, such as radioimmunoassay (RIA) or enzyme-linked immunoabsorbent assay (ELISA). The binding affinity of a monoclonal antibody or portion thereof also can be determined by the Scatchard analysis of Munson et al. (1980) *Anal. Biochem.*, 107: 220-239.

In certain embodiments, an anti-MUC4α N-ter antibody or and anti-MUC4α C-ter or portion thereof produced using any of the methods discussed above may be further altered or optimized to achieve a desired binding specificity and/or affinity using art recognized techniques, such as those described herein.

4) Antibody Modification/Enhancement.

In one embodiment, partial antibody sequences derived from an antibody that binds to MUC4α N-ter and/or MUC4α C-ter may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332: 323-327; Jones et al. (1986) *Nature* 321: 522-525; Queen et al. (1989) *Proc. Natl. Acad. Sci. USA*, 86:10029-10033). Such framework sequences can be obtained from public DNA databases that include germline antibody gene sequences.

Thus, one or more structural features of an anti-MUC4α N-ter and/or an anti-MUC4α C-ter antibody described herein, such as the CDRs, can be used to create structurally related antibodies that retain at least one functional property of the antibodies of anti-MUC4 antibodies described herein (e.g., binding to MUC4α on a neoplastic cell, inducing apoptosis of a target cell, etc.)

In a particular embodiment, one or more CDR regions selected from clones 2172 (5H8), 2173 (6G2), 2175 (7F7), 2212 (3A2), 2213 (3F9), 2214 (7E10), 2382 (7H7), 2103 (5H7), 2106 (6E12), 2107 (8A12), described herein is combined recombinantly with known human framework regions and CDRs to create additional, recombinantly-engineered, anti-ErbB3 antibodies of the invention. The heavy and light chain variable framework regions can be derived from the same or different antibody sequences.

It is well known in the art that antibody heavy and light chain CDR3 domains play a particularly important role in the binding specificity/affinity of an antibody for an antigen (see, e.g., Hall et al. (1992) *J. Immunol.*, 149:1605-1612; Polymenis et al. (1994) *J. Immunol.*, 152:5318-5329; Jahn et al. 91995) *Immunobiol.*, 193: 400-419; Klimka et al. (2000) *Brit. J. Cancer*, 83: 252-260; Beiboer et al. (2000) *J. Mol. Biol.*, 296: 833-849; Rader et al. (1998) *Proc. Natl. Acad. Sci. USA*, 95: 8910-8915; Barbas et al. (1994) *J. Am. Chem. Soc.*, 116: 2161-2162; Ditzel et al. (1996) *J. Immunol.*, 157: 739-749).

Accordingly, in certain embodiments, antibodies are generated that include the heavy and/or light chain CDR3s of the particular antibodies described herein (e.g., clones 2172 (5H8), 2173 (6G2), 2175 (7F7), 2212 (3A2), 2213 (3F9), 2214 (7E10), 2382 (7H7), 2103 (5H7), 2106 (6E12), and 2107 (8A12)). The antibodies can further include the heavy and/or light chain CDR1 and/or CDR2s of the antibodies described herein (e.g., clones 2172 (5H8), 2173 (6G2), 2175 (7F7), 2212 (3A2), 2213 (3F9), 2214 (7E10), 2382 (7H7), 2103 (5H7), 2106 (6E12), 2107 (8A12) of the present invention In various embodiments the CDR1, 2, and/or 3 regions of the engineered antibodies described above can comprise the exact amino acid sequence(s) as those found in clones 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12). However, the ordinarily skilled artisan will appreciate that some deviation from the exact CDR sequences may be possible while still retaining the ability of the antibody to bind MUC4α N-ter and/or MUC4α C-ter effectively (e.g., conservative amino acid substitutions). Accordingly, in certain embodiments, the antibody may be composed of one or more CDRs that are, for example, 90%, 95%, 98%, 99% or 99.5% identical to one or more CDRs of clones 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12).

In another embodiment, one or more residues of a CDR may be altered to modify binding to achieve a more favored on-rate of binding. Using this strategy, an antibody having ultra high binding affinity of, for example, $10^{-10}$ M or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, in certain embodiments, modifications can also be made within one or more of the framework regions, FR1, FR2, FR3 and FR4, of the heavy and/or the light chain variable regions of an antibody, so long as these modifications do not eliminate the binding affinity of the antibody.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC) (see, e.g., Caron et al. (1992) *J. Exp Med.* 176: 1191-1195, and Shopes et al. (1992) *J. Immunol.* 148: 2918-2922, and the like). Homodimeric antibodies with enhanced anti-tumor activity may also be prepared using heterobifunctional cross-linkers as described in Wolff et al. (1993) *Cancer Res.*, 53: 2560-2565. Alternatively, an antibody can be engineered which has dual Fc regions and may thereby have enhanced complement lysis and ADCC capabilities (see, e.g., Stevenson et al. (1989) *Anti-Cancer Drug Design* 3: 219-230.

B) Identification of Other Antibodies Binding the Same Epitope(s) as Antibodies 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12).

Having identified useful anti-MUC4 antibodies that specifically bind MUC4α N-ter and/or MUC4α C-ter (e.g., 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12)), other "related" anti-MUC4 antibodies can be identified by screening for antibodies that cross-react with the identified antibodies, either at the epitope bound by the antibodies, and/or for antibodies that cross-react with the identified antibodies for binding to a cancer cell that overexpresses MUC4 (e.g., a pancreatic cancer cell), and/or with an idiotypic antibody raised against 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12) antibodies described herein.

1) Cross-Reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine) In general, it is desirable to use a myeloma cell line which does not secrete an immunoglobulin. Several such lines are known in the art. One generally preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology*, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

2) Cross-Reactivity with 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12) Antibodies.

In another approach, other MUC4 specific antibodies can be identified by the fact that they bind the same epitope as the "prototypic" antibodies of described herein (e.g., 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12)). In certain embodiments, one can screen, e.g. antibody libraries for antibodies that compete with the prototypic antibodies described herein for binding to a cancer cell the overexpresses MUC4 (e.g. a pancreatic cancer cell), while in certain other embodiments, one can screen antibody libraries for antibodies that compete with the prototypic antibodies described herein for binding to MUC4α-N-ter and/or MUC4α-C-ter.

Methods of screening libraries for competitive binding are well known to those of skill in the art. Such screening methods, done, for example in the presence of labeled prototypic antibodies described herein allows rapid identification of library members that compete with and exclude the prototypic antibodies of this invention from binding and to the designated the target protein or cell.

In certain embodiments, cross-reactive MUC4 specific antibodies show at least 60%, preferably 80%, more preferably 90%, and most preferably at least 95% or at least 99% cross-reactivity with one or more of the prototypic antibodies described herein.

C) Phage Display Methods to Select Other "Related" Antibodies that Bind MUC4 Non-TR Domains.

In certain embodiments phage display systems (or yeast display systems) can be used to identify, select, or improve antibodies that bind to MUC4α N-ter and/or to MUC4α C-ter. In phage- and yeast-display systems, single chain antibodies (antibodies that exist as a single polypeptide chain), more preferably single chain Fv antibodies (scFv) in which a variable heavy and a variable light chain are joined together (directly or through a peptide linker) to is expressed from a nucleic acid including $V_H$- and $V_L$-encoding sequences either joined directly or joined by a peptide-encoding linker (see e.g., Huston, et al. (1988) *Proc. Nat. Acad. Sci. USA*, 85: 5879-5883) that can be expressed on the surface of filamentous phage or yeast. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons. The two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Phase display systems can be used to screen numerous antibody constructs for binding to MUC4α N-ter and/or to MUC4α C-ter.

1) Chain Shuffling Methods.

One approach to creating modified single-chain antibody (scFv) gene repertoires has been to replace the original $V_H$ or $V_L$ gene with a repertoire of V-genes to create new partners (chain shuffling) (Clackson et al. (1991) *Nature*. 352: 624-628). Using chain shuffling and phage display, the affinity of a human scFv antibody fragment that bound the hapten phenyloxazolone (phOx) was increased from 300 nM to 1 nM (300 fold) (Marks et al. (1992) *Bio/Technology* 10: 779-783).

Thus, for example, to alter the affinity of an antibody that binds to MUC4α N-ter and/or to MUC4α C-ter, a mutant scFv gene repertoire can be created containing a $V_H$ gene of the prototypic antibodies (e.g. MAbs 2172, 2173, 2175, 2212, 2213, 2214, 2382 2103, 2106 and 2107) antibody and a human $V_L$ gene repertoire (light chain shuffling). The scFv gene repertoire can be cloned into a phage display vector, e.g., pHEN-1 (Hoogenboom et al. (1991) *Nucleic Acids Res.*, 19: 4133-4137) or other vectors, e.g. as described herein in the examples, and after transformation a library of transformants is obtained.

Similarly, for heavy chain shuffling, the anti-MUC4 antibody (e.g., MAbs 2172, 2173, 2175, 2212, 2213, 2214, 2382 2103, 2106 and 2107, etc.) $V_H$ CDR1 and/or CDR2, and/or CDR3 and light chain are cloned into a vector containing a human $V_H$ gene repertoire to create a phage antibody library of transformants. For detailed descriptions of chain shuffling to increase antibody affinity see Schier et al. (1996) *J. Mol. Biol.,* 255: 28-43, and the like.

2) Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.,* 196: 901-917; Chothia et al. (1986) *Science,* 233: 755-8; Nhan et al. (1991) *J. Mol. Biol.,* 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.,* 234: 564-578; Wells (1990) *Biochemistry,* 29: 8509-8516). Site-directed mutagenesis of CDRs and screening against the prostate cancer cells, e.g. as described herein in the examples, can produce antibodies having improved binding affinity.

3) CDR Randomization to Produce Higher Affinity Human scFv.

In an extension of simple site-directed mutagenesis, mutant antibody libraries can be created where partial or entire CDRs are randomized ($V_L$ CDR1CDR2 and/or CDR3 and/or $V_H$ CDR1, CDR2 and/or CDR3). In one embodiment, each CDR is randomized in a separate library, using a known antibody (e.g., MAbs 2172, 2173, 2175, 2212, 2213, 2214, 2382 2103, 2106 and 2107) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.,* 234: 564-578).

$V_H$ CDR3 often occupies the center of the binding pocket, and thus mutations in this region are likely to result in an increase in affinity (Clackson et al. (1995) *Science,* 267: 383-386). In one embodiment, four $V_H$ CDR3 residues are randomized at a time using the nucleotides NNS (see, e.g., Schier et al. (1996) *Gene,* 169: 147-155; Schier and Marks (1996) *Human Antibodies and Hybridomas.* 7: 97-105, 1996; and Schier et al. (1996) *J. Mol. Biol.* 263: 551-567).

D) Creation of Other Antibody Forms.

Using the sequences (e.g. $V_H$ and/or $V_L$ sequences) of the antibodies described herein (e.g., 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12)) other antibody forms can readily be created. Such forms include, but are not limited to multivalent antibodies, scFv, $(scFv')_2$, Fab, $(Fab')_2$, chimeric antibodies, and the like.

1) Creation of Homodimers.

For example, to create $(scFv')_2$ antibodies, two anti-MUC4 scFvs are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce $(scFv')_2$ dimers, the cysteine is reduced by incubation with 1 mM 3-mercaptoethanol, and half of the scFv blocked by the addition of DTNB. Blocked and unblocked scFvs are incubated together to form $(scFv')_2$ and the resulting material can be analyzed by gel filtration. The affinity of the resulting dimmer can be determined using standard methods, e.g. by BIAcore.

In one illustrative embodiment, the $(scFv')_2$ dimer is created by joining the scFv' fragments through a linker, more preferably through a peptide linker. This can be accomplished by a wide variety of means well known to those of skill in the art. For example, one preferred approach is described by Holliger et al. (1993) *Proc. Natl. Acad. Sci. USA,* 90: 6444-6448 (see also WO 94/13804).

It is noted that using the $V_H$ and/or $V_L$ sequences of the antibodies described herein Fabs and $(Fab')_2$ dimers can also readily be prepared. Fab is a light chain joined to $V_H$-$C_H$1 by a disulfide bond and can readily be created using standard methods known to those of skill in the art. The $F(ab)'_2$ can be produced by dimerizing the Fab, e.g. as described above for the $(scFv')_2$ dimer.

2) Chimeric Antibodies.

The antibodies contemplated herein also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein are mouse antibodies, chimeric antibodies are contemplated, particularly when such antibodies are to be used in species other than humans (e.g., in veterinary applications). Chimeric antibodies are antibodies comprising portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature,* 312: 643; and anti-tumor antigens: Sahagan et al.

(1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line that produces a prostate cancer specific antibody of this invention. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of a prostate cancer specific antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

3) Intact Human Antibodies.

In another embodiment, fully human or humanized anti-MUC4 antibodies that bind MUC4α domains other than the TR domain (e.g., that bind MUC4α-N-ter and/or MUC4α-C-ter) are contemplated. Such human or humanized antibodies can readily be produced in a manner analogous to making chimeric human antibodies.

A "humanized antibody" or "humanized immunoglobulin" refers to an non-human (e.g., mouse or rabbit) antibody containing one or more amino acids that have been substituted with a correspondingly positioned amino acid from a human antibody. In some cases, humanized antibodies produce a reduced immune response in a human host, as compared to a non-humanized version of the same antibody. It is understood that the humanized antibodies designed and produced by the methods described herein may have amino acid substitutions which have substantially no effect on antigen binding or other antibody functions.

In general, humanized antibodies are made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (see, e.g., EP 239,400; PCT publication WO 91/09967; U.S. Pat. Nos. 5,225,539; 5,530,101; and 5,585,089), veneering or resurfacing (see, e.g., EP 592,106; EP 519,596; Padlan (1991) *Molecular Immunol.*, 28(4/5):489-498; Studnicka et al. (1994) *Protein Engineering* 7(6): 805-814; Roguska et al. (1994) *Proc. Natl. Acad. Sci. USA*, 91: 969-973), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al. (1988) *Nature* 332: 323). Additional methods for humanizing antibodies contemplated for use are described in U.S. Pat. Nos. 5,750,078; 5,502,167; 5,705,154; 5,770,403; 5,698,417; 5,693,493; 5,558,864; 4,935,496; and 4,816,567, and PCT Publication Nos: WO 98/45331 and WO 98/45332. In certain illustrative embodiments, a subject rabbit antibody may be humanized according to the methods set forth in published U.S. Patent Publications US 2004/0086979 A1 and US 2005/0033031 A1.

In one embodiment of particular interest, a subject antibody may be humanized in accordance with the methods set forth in U.S. Patent Publication US 2006-0099204 A1. In general, this humanization method involves identifying a substitutable position of an antibody by comparing sequences of antibodies that bind to the same antigen, and replacing the amino acid at that position with a different amino acid that is present at the same position of a similar human antibody. In these methods, the amino acid sequence of a parental (e.g., rabbit antibody) is compared to (e.g., aligned with) the amino acid sequences of other related rabbit antibodies to identify variation tolerant positions. The amino acid sequence of the variable domain of the parental rabbit antibody is usually compared to a database of human antibody sequences, and a human antibody that has an amino acid sequence that is similar to that of the parental antibody is selected. The amino acid sequences of the parental antibody and the human antibody are compared (e.g., aligned), and amino acids at one or more of the variation tolerant positions of the parental antibody are substituted by correspondingly positioned amino acids in the human antibody. In this humanization method, the CDR regions of the antibody may be humanized in addition to the framework regions.

4) Diabodies.

In certain embodiments, this diabodies are contemplated comprising one or more of the $V_H$ and $V_L$ domains of an antibody selected from 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12). The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444-6448.

5) Unibodies.

In certain embodiments using the prototypical antibodies described herein (e.g., 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12)), can be used to produce unibodies having the same or similar binding specificity can be prepared. Unibodies are a stable, smaller antibody format with an anticipated longer therapeutic window than certain small antibody formats. In certain embodiments unibodies are produced from IgG antibodies (e.g., IgG4) by eliminating the hinge region of the antibody. Unlike the full size IgG4 antibody, the half molecule fragment is very stable and is termed a uniBody. Halving the IgG4 molecule leaves only one area on the UniBody that can bind to a target. Methods of producing unibodies are described in detail in PCT Publication WO2007/059782 and by Kolfschoten et al. (2007) *Science* 317: 1554-1557).

6) Affibodies.

In certain embodiments using the prototypical antibodies described herein (e.g., 2172 (5H8), 2173 (6G2), 2175 (7F7), 2212 (3A2), 2213 (3F9), 2214 (7E10), 2382 (7H7), 2103 (5H7), 2106 (6E12), and/or 2107 (8A12)), are used to construct affibody molecules that bind cancer cells. Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.*, 269: 2647-2655.). Details of Affibodies and methods of production are known to those of skill (see, e.g., U.S. Pat. No. 5,831,012).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the antibody and/or chimeric moiety is to be used. In other words, for use in a human, it is desirable to use a human, humanized, or chimeric human antibody.

7) Measurement of Antibody/Polypeptide Binding Affinity.

As explained above, selection for increased affinity/avidity can involve measuring the affinity of the antibody for the target antigen (e.g., MUC4, MUC4α-N-ter, and/or MUC4α-C-ter). Methods of making such measurements are well known to those of skill in the art. Briefly, for example, the $K_d$ of the antibody is determined from the kinetics of binding to, e.g. the target cell in a BIAcore, a biosensor based on surface plasmon resonance. For this technique, the antigen (e.g., MUC4, MUC4α-N-ter, and/or MUC4α-C-ter) or cell (e.g., a pancreatic cancer cell) is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

II. Chimeric Moieties Comprising Anti-MUC4 Antibodies Attached to One or More Effectors.

The antibodies described herein bind to regions of MUC4 that are not the TR domain (e.g., they bind to MUC4α-N-ter and/or to MUC4α-C-ter). Accordingly they are believed to specifically bind cells expressing MUC4 (e.g., cancer cells) despite the occurrence of post-translational modifications (e.g., glycosylation, etc.). The antibodies can be used alone as therapeutics (e.g. to inhibit growth and/or proliferation of a neoplastic cell), or in certain embodiments, they can be coupled to an effector to provide efficient and specific delivery of the effector (e.g. an effector molecule such as a cytotoxin, a radiolabel, a cancer drug, etc.) to various cancer cells (e.g. isolated cells, metastatic cells, solid tumor cells, etc.).

A chimeric molecule or chimeric composition or chimeric moiety refers to a molecule or composition wherein two or more molecules that exist separately in their native state are joined together to form a single molecule having the desired functionality of its constituent molecules. Typically, one of the constituent molecules of a chimeric molecule is a "targeting molecule" that specifically binds a target (e.g., a MUC4). In various embodiments, the use of an antibody that specifically binds a MUC4α-N-ter and/or MUC4α-C-ter region of MUC4 as a targeting molecule is contemplated. The targeting molecule (e.g., MUC4 antibody) is then used to specifically or preferentially deliver and/or localize the effector(s) to the target cell (e.g., a pancreatic cancer cell).

In one "direct targeting" approach, the effector is provided attached to the anti-MUC4 antibody thereby forming a chimeric construct. The effector can be directly attached, or attached through a linker. In certain embodiments, where the effector comprises a protein, the effector can be attached to the antibody directly or through a peptide linker (e.g., a (Gly$_4$Ser)$_3$ (SEQ ID NO:3) linker and in certain embodiments, at least a portion of the chimeric construct can be expressed as a fusion protein. As the antibody is attached to the effector binding of the antibody to the MUC4 target when presented on a cell (e.g., an ovarian cancer, cell, a pancreatic cancer cell, etc.) effectively delivers the effector to that cell.

In a "two-phase targeting" or "pre-targeting" approach, the anti-MUC4 antibody alone or a construct comprising the anti-MUC4 antibody attached to an effector comprising an epitope tag is first administered to the subject or sample. The antibody or antibody-epitope tag construct binds the cell.

Accordingly, in various embodiments constructs comprising one or more anti-MUC4 antibodies attached to an effector or one or more effectors attached to an anti-MUC4 antibody described herein are contemplated. In various embodiments the effector comprises a moiety such as a cytokine, a second antibody, a cytotoxin, a radionuclide, a detectable label, a radiosensitizer, a chelater, a drug carrier system (e.g., lipid, liposome, polymeric microparticle or nanoparticle, A) Illustrative Effectors.

1) Cytokines.

In certain embodiments the anti-MUC4 antibody is attached to an effector comprising a cytokine. The cytokine can be selected for its direct effect on the target cell, or for the ability to induce/recruit an immune response directed against the target cell bearing the marker (e.g., MUC4) to which the antibody binds.

Illustrative cytokines include, but are not limited to interleukin 2 (IL-2), interleukin 6 (IL-6), interleukin 7 (IL-7), interleukin 12 (IL-12), interleukin 10 (IL-10), interleukin 15

(IL-15), interleukin 17 (IL-17), interleukin 24 (IL-24), granulocyte-macrophage colony stimulating factor (GM-CSF), tumor necrosis factor (TNF), interferon (e.g., IFN-α, IFN-β, IFN-γ), TNF-related apoptosis inducing ligand (TRAIL), the Fas ligand (FasL), and/or active fragments thereof. Natural cytokines can occur as monomers, homo- or heterodimers, or as trimers. Single-chain derivatives have been generated for heterodimeric cytokines (e.g. IL-12) as well as homotrimeric cytokines (e.g. TNF).

The antibody can be attached directly to the cytokine or coupled to the cytokine through a linker. As indicated above, in certain embodiments, the antibody is chemically conjugated to the cytokine (see, below) or can be coupled to the cytokine through a peptide linker. In certain embodiments at least a portion of the antibody and the cytokine are expressed as a fusion protein. By way of example, in certain embodiments, IgG-cytokine fusion proteins are generated by fusing one or two cytokines to the C- or N-terminus of an anti-MUC4 antibody heavy or light chain. The dock-and-lock method (DNL) can be applied to generated tetravalent cytokine antibody fusion proteins. Alternatively, in certain embodiments, cytokines can be fused to the Fc region of an anti-MUC4 antibody or to scFv-Fc, scFc-CH3, scFv-CH1:scFv:CL, Fab or F(ab')$_2$ fragments. Furthermore, in certain embodiments, scFv or diabodies can be fused directly (or through a peptide linker) to a cytokine generating either monovalent or multivalent molecules.

In certain embodiments suitable for a "two-phase targeting" or "pre-targeting" approach, the cytokine is provided as a second construct comprising the cytokine attached to a second antibody that binds to the anti-MUC4 antibody or to an epitope tag attached to the anti-MUC4 antibody. The second construct then binds to the anti-MUC4 antibody bound to the target cell thereby delivering the cytokine to the target cell.

2) Second Antibody.

Figure 13A:
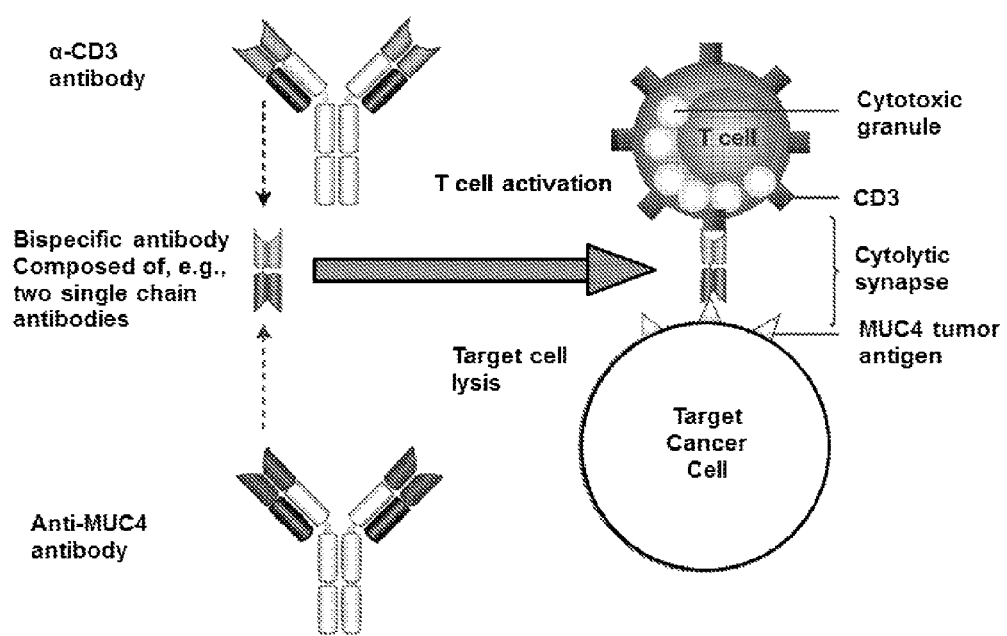
FIG. 13A illustrates the use of a bispecific antibody to direct an immune response against a cell expressing a MUC4 marker (e.g., a pancreatic cancer cell). Generation of a bispecific (anti-MUC4-anti-CD3) antibody from the variable domains of two distinct monoclonal antibodies is depicted on the left. The bispecific antibody can transiently connect a T cell and a cancer cell by simultaneously binding CD3 and a target antigen. This will trigger T-cell activation involving cytotoxic granule fusion, transient cytokine release, and proliferation. Redirected lysis of the attached cancer cell can involve membrane perforation by perforin, and subsequent programmed cell death as induced by granzymes.

In certain embodiments the effector comprises a second antibody and the construct thereby forms a bispecific antibody. In certain embodiments the second antibody is one that facilitates the recruitment of an immune response to the target cell. For example, in certain embodiments, the second antibody binds a marker on an immune effector cell (e.g., a T cell). For example, bispecific antibody constructs comprising an antibody that binds a tumor marker attached to an antibody that binds CD3 on T cells has been used to induced a cytotoxic T cell response directed against a cancer cell (see, e.g., Baeuerle, and Reinhardt (2009) Cancer Res., 69(12): 4941-4944). This strategy is illustrated schematically in FIG. 13A.

While, in certain embodiments, the effector comprises an antibody that binds CD3 the effector need not be limited to these antibodies. In various embodiments the effector can comprise a second antibody that binds a surface receptor listed in Table 1.

TABLE 1

Illustrative, but non-limiting list of surface receptors for use as targets in bispecific antibodies.

| Surface Receptor | Cell Type |
| --- | --- |
| TcR | T cells |
| CD2 | T-/NK cells |
| CD3 | T cells |
| CD5[b] | T cells |
| CD16 | NK cells/LGL PMN |

TABLE 1-continued

Illustrative, but non-limiting list of surface receptors for use as targets in bispecific antibodies.

| Surface Receptor | Cell Type |
| --- | --- |
| CD28[c] | T cells |
| CD32 | PMN/MQ macrophages |
| CD64 | PMN[d]/MQ macrophages |

TcR, T-cell receptor;
LGL, large granular lymphocyte;
PMN, polymorphonuclear leukocyte;
MQ, macrophage.
[b]Effective when used in conjunction with CD28 and/or CD3.
[c]Effective when used in conjunction with CD2 or CD5 and/or CD3.
[d]When activated with IFN-g or G-CSF.

Figure 13B:
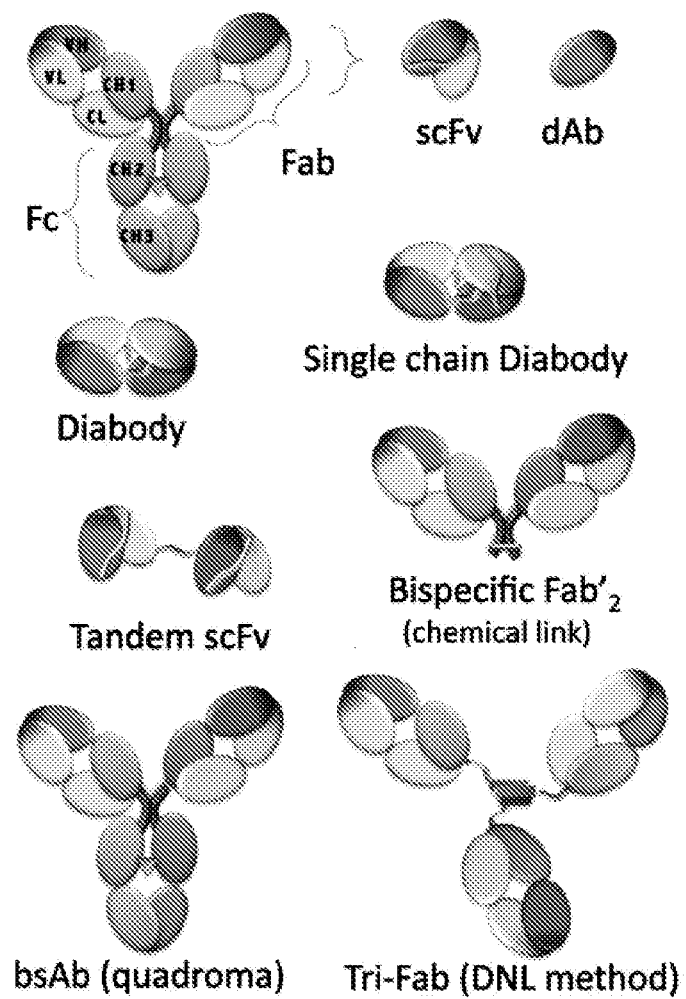
FIG. 13B illustrates various forms of bispecific antibody.

In various embodiments the bispecific antibody (anti-MUC4 antibody attached to a second antibody) is provides in a form a diabody, a single-chain diabody, a chemically conjugated bispecific (Fab')$_2$, an (Fab')2 fusion protein, a tandem ScFv, a quadroma (bsAb), and a tri-Fab (see, e.g., FIG. 13B).

Numerous method are available for making bispecific antibodies. For example, in one embodiment, bispecific antibodies are prepares using the hybrid hybridomal method of Milstein, and Cuello (1983) Nature 305: 537-540. This approach involves the biological fusion of two hybridomas each expressing one of the desired antibodies. In certain embodiments antibodies derived from two different hybridomas can be coupled directly to each other using bifunctional cross-linking reagents such as N-succinimidyl 3-(2-pyridyldithiol-propionate (SPDP) (see, e.g., Perez et al. (1985) Nature, 316: 354-356; Karpovsky et al. (1984) J. Exp. Med., 160: 1686-1701, and the like). Another illustrative approach uses 2-nitro benzoic acid (DTNB) or o-phenyl-dimaleimide (o-PDM), which are able to react with sulfhydryl groups present in the hinge-region of IgG molecules (Tutt et al. (1991) Eur. J. Immunol., 21: 1351-1358; Brennan et al. (1985) Science, 229: 81; Glennnie et al. (1987) J. Immunol., 139: 2367, and the like). Purified IgG or enzymatically produced fragments thereof, are reduced under mild conditions yielding Fab' reagents with free hinge-region region SH groups that are covalently linked to DTNB or o-PDM. A second antibody, reduced to yield Fab' fragments containing free hinge-region SH groups, IS added and disulfide- or thioether linked bispecific antibody molecules are generated by oxidation. In addition, various forms of genetically engineered bispecific antibodies have been produced. For example, scFv molecules, functionally expressed, for example, in E. coli have been modified to express a terminal cysteine by which they can be crosslinked using conventional sulfide-reactive crosslinkers (see, e.g., Cumber et al. (1992) J. Immunol., 149: 120-126). Secondly, by interconnecting two different scFv constructs with a long enough flexible linker, so-called bispecific single chain Fv fragments (Bs(scFv)2) have been generated (see, e.g., Mallender and Voss (1994) J. Biol. Chem., 269: 199-206; Mack et al. (1995) Proc. Natl. Acad. Sci., USA, 92: 7021-7025, and the like). In various embodiments scFv fragments can be coupled to form bispecific reagents using the fos-jun leucine zipper technique. This technique takes advantage of the property of the transcription factors fos and jun to spontaneously form stable fos-jun heterodimers (Kostelny et al. (1992) J. Immunol., 148: 1547-1553). Two different scFv fusion proteins are constructed, either containing fos or jun. Upon expression, fos-fos and jun-jun homodimers are formed, which can be monomerized by mild reduction. Subsequent mixing and oxidation of quantities of scFv-fos and scFv-jun fragments will preferentially yield bispecific fos-jun zippered antibody fragments. To further minimize the size of these antibody constructs, pepsin digestion to remove part of the fos-jun zipper is possible (Tso et al. (1995) *J. Hematother.*, 4: 389-394). Holliger et al. *Proc. Natl. Acad. Sci. USA,* 90: 6444-6448, showed that when scFv molecules were constructed with no or very short linkers, intrachain pairing was no longer possible, but, instead, interchain pairing occurred. This phenomenon apparently resulted from a natural affinity of VH for VL and vice versa. This concept was exploited to develop so-called diabodies in which the VH- and VL-encoding regions of two different antibody specificities were expressed on two separate chains, each containing a linker short enough to prevent self-assembly of the individual VH and VL domains. Simultaneous and equimolar expression of the two chains, e.g. using a dicistronic expression system, results in the formation of a bispecific molecule by dual interchain $V_H$-$V_L$ pairing (Perisic et al. (1994) *Structure,* 2: 1217-1226; Holliger et al. (1996) *Protein Eng.,* 9: 299-305). Optimizing the formation of true bismonomeric specific reagent has been described by introducing a disulfide bridge between one of the VH-VL chains. Thus, the possibilities for genetic engineering bispecific antibodies are numerous and readily available to one of skill in the art. Accordingly, these approaches are intended to be illustrative and non-limiting. Using the teachings provided herein numerous other bispecific antibodies will be available to one of skill in the art.

3) Cytotoxins.

The anti-MUC4 antibodies described herein can be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters, and the like as described herein. In certain embodiments the cytotoxin comprises a protein cytotoxin.

Enzymatically active toxins and fragments thereof are exemplified by *diphtheria* toxin A fragment, nonbinding active fragments of *diphtheria* toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example.

In certain embodiments the cytotoxins can include, but are not limited to *Pseudomonas* exotoxins, *Diphtheria* toxins, ricin, abrin, and derivatives thereof. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity (see, e.g., Siegall et al. (1989) *J. Biol. Chem.* 264: 14256-14261).

In certain embodiments the antibody is attached to a preferred molecule in which domain Ia (amino acids 1 through 252) is deleted and amino acids 365 to 380 have been deleted from domain Ib. In certain embodiments all of domain Ib and a portion of domain II (amino acids 350 to 394) can be deleted, particularly if the deleted sequences are replaced with a linking peptide.

In addition, the PE and other cytotoxic proteins can be further modified using site-directed mutagenesis or other techniques known in the art, to alter the molecule for a particular desired application. For example, means to alter the PE molecule in a manner that does not substantially affect the functional advantages provided by the PE molecules described here can also be used and such resulting molecules are intended to be covered herein.

Methods of cloning genes encoding PE fused to various ligands are well known to those of skill in the art (see, e.g., Siegall et al. (1989) *FASEB J.,* 3: 2647-2652; and Chaudhary et al. (1987) *Proc. Natl. Acad. Sci. USA,* 84: 4538-4542).

Like PE, *diphtheria* toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science,* 175: 901-903; Uchida et al. (1973) *J. Biol. Chem.,* 248: 3838-3844).

In certain embodiments, the antibody-*Diphtheria* toxin chimeric moieties of this invention have the native receptor-binding domain removed by truncation of the *Diphtheria* toxin B chain. One illustrative modified *Dipththeria* toxin is DT388, a DT in which the carboxyl terminal sequence beginning at residue 389 is removed (see, e.g., Chaudhary et al. (1991) *Bioch. Biophys. Res. Comm.,* 180: 545-551). Like the PE chimeric cytotoxins, the DT molecules can be chemically conjugated to the prostate cancer specific antibody, but, in certain preferred embodiments, the antibody will be fused to the *Diphtheria* toxin by recombinant means (see, e.g., Williams et al. (1990) *J. Biol. Chem.* 265: 11885-11889).

4) Radionuclides and Other Detectable Labels.

a) Imaging Compositions.

In certain embodiments, the chimeric moieties contemplated herein can be used to direct detectable labels to cancer cell and/or to a tumor site. This can facilitate tumor detection and/or localization. It can be effective for detecting primary tumors, or, in certain embodiments, secondary tumors produced by, e.g., prostate metastatic cells. In certain embodiments, the effector component of the chimeric moiety comprises a "radio-opaque" label, e.g. a label that can be easily visualized using x-rays. Radio-opaque materials are well known to those of skill in the art. The most common radio-opaque materials include iodide, bromide or barium salts. Other radiopaque materials are also known and include, but are not limited to, organic bismuth derivatives (see, e.g., U.S. Pat. No. 5,939,045), radio-opaque polyurethanes (see, e.g., U.S. Pat. No. 5,346,981), organobismuth composites (see, e.g., U.S. Pat. No. 5,256,334), radio-opaque barium polymer complexes (see, e.g., U.S. Pat. No. 4,866,132), and the like.

The anti-MUC4 antibodies described herein can be coupled directly to the radio-opaque moiety or they can be attached to a "package" (e.g., a chelate, a liposome, a polymer microbead, a nanoparticle, etc.) carrying, containing, or comprising the radio-opaque material, e.g., as described below.

In addition to radio-opaque labels, other labels are also suitable for use in the methods described herein. In various embodiments detectable labels suitable for use as the effector molecule component of the chimeric moieties of this invention include any composition detectable by spectroscopic, photochemical, biochemical, immunochemical, electrical, optical or chemical means. Useful labels include, but are not limited to, magnetic beads (e.g., DYNABEADS™), and the like), radiolabels (e.g. $^3$H, $^{125}$I, $^{35}$S, $^{14}$C, or $^{32}$P), enzymes (e.g., horse radish peroxidase fluorescent dyes (e.g., fluorescein isothiocyanate, texas red, rhodamine, green fluorescent protein, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In certain embodiments, suitable radiolabels include, but are not limited to, $^{99}$Tc, $^{203}$Pb, $^{67}$Ga, $^{68}$Ga, $^{72}$As, $^{111}$In, $^{113m}$In, $^{97}$Ru, $^{62}$Cu, 641Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, certain radiolabels may be detected using photographic film, scintillation detectors, PET imaging, MRI, and the like. Fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

b) Cytotoxic/Cytostatic Radionuclides.

In certain embodiments, the effector comprises one or more radioisotopes that when delivered to a target cell bring about radiation-induced cell death.

For medical purposes, the most important types of decay are gamma emission, beta decay, alpha decay, and electron capture. The gamma emitted by a radionuclide, such a $^{131}$I, exits the body, allowing the use of external scintigraphic imaging to determine the biodistribution of radiolabeled antibodies (the optimal energy range for immunoscintigraphy is 100-250 keV). In contrast, beta particles deposit most of their energy within a few millimeters of the point of decay. Beta emissions from radionuclides such as $^{131}$I or $^{90}$Y that have targeted antigen-positive tumor cells can kill nearby antigen-negative tumor cells through a "crossfire" effect.

Yttrium-90, a pure beta emitter, has several properties that make it an attractive choice for radioimmunotherapy: 1) a high beta energy ($E_{max}$=2.29 MeV; maximum range of particulate energy in tissue=11.9 mm) which enables it to kill adjacent tumor cells; 2) metal chemistry, which facilitates the synthesis of radioisotope-antibody conjugates and use of a pretargeting approach; and 3) a sufficiently long physical half-life (2.67 days) for use with intact SHALs, which may take 1-3 days to reach their peak concentration in tumors.

In certain embodiments, the effector can include an alpha emitter, i.e. a radioactive isotope that emits alpha particles and/or an auter-electron emitter. Alpha-emitters and auger-electron emitters have recently been shown to be effective in the treatment of cancer (see, e.g., Bodei et al. (2003) *Cancer Biotherapy and Radiopharmaceuticals*, 18:861). Suitable alpha emitters include, but are not limited $^{212}$Bi, $^{213}$Bi, $^{211}$At, and the like.

Table 2 illustrates some radionuclides suitable for radioimmunotherapy. This list is intended to be illustrative and not limiting.

TABLE 2

Illustrative radionuclides suitable for radioimmunotherapy.

| Radio-nuclide | Decay mode | Physical half life | Max. particulate energy (%) |
|---|---|---|---|
| I-131 | β, γ | 8 d | 807 keV (1)* |
|  |  |  | 606 keV (86)* |
|  |  |  | 336 keV (13)* |
| Cu-67 | β, γ | 62 h | 577 keV (20)* |
|  |  |  | 484 keV (35)* |
|  |  |  | 395 keV (45)* |
| Lu-177 | β, γ | 6.7 d | 497 keV (90)* |
|  |  |  | 384 keV (3)* |
|  |  |  | 175 keV (7)* |
| Re-186 | β, γ, electron capture | 91 h | 1.07 MeV (77)* |
|  |  |  | 934 keV (23)* |
| Y-90 | β | 64 h | 2.29 MeV (100)* |
| Re-188 | β | 17 h | 2.13 MeV (100)* |
| Bi-212 | α, β | 1 h | 6.09 MeV (27)** |
|  |  |  | 6.05 MeV (70)** |
|  |  |  | 5.77 MeV (2)** |
|  |  |  | 5.61 MeV (1)** |
| At-211 | α, electron capture | 7 h | 5.87 MeV (100)** |
| I-125 | Electron capture | 60 d | 35 keV (100) |

*beta irradiation,
**alpha irradiation,
RBE, relative biologic effectiveness

In certain embodiments, the effector can include an alpha emitter, i.e. a radioactive isotope that emits alpha particles. Alpha-emitters have recently been shown to be effective in the treatment of cancer (see, e.g., McDevitt et al. (2001) *Science* 294:1537-1540; Ballangrud et al. (2001) *Cancer Res.* 61: 2008-2014; Borchardt et al. (2003) *Cancer Res.* 63: 5084-50). Suitable alpha emitters include, but are not limited to Bi, $^{213}$Bi, $^{211}$At, and the like.

5) Radiosensitizers.

In another embodiment, the effector can comprise a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849, 738), compounds containing certain diamines (see, e.g., U.S. Pat. No. 5,700,825), BCNT (see, e.g., U.S. Pat. No. 5,872, 107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

6) Chelates

Many of the pharmaceuticals and/or radiolabels described herein can be provided as a chelate, particularly where a pre-targeting strategy is utilized. The chelating molecule is typically coupled to a molecule (e.g. biotin, avidin, streptavidin, etc.) that specifically binds an epitope tag attached to a prostate cancer specific antibody of this invention.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, and the like.

Examples of certain illustrative chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N,N,N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

In certain embodiments the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl):154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

7) Drug Carrier Systems.

In certain embodiments the effector comprises a drug carrier moiety. Such moieties include, but are not limited to lipid microparticle or nanoparticles such a lipids, micelles, liposomes, polymeric microparticles or nanoparticles and the like. These moieties can be attached to the antibody and can further comprise a drug or other active agent which is delivered to the target (cell) by the anti-MUC4 antibody attached thereto.

a) Lipidic Microparticles or Nanoparticles.

In various embodiments the effector comprises a lipid microparticles or nanoparticles that includes at least one lipid component forming a condensed lipid phase. Typically, a lipidic microparticle or nanoparticle has preponderance of lipids in its composition. The exemplary condensed lipid phases are solid amorphous or true crystalline phases; isomorphic liquid phases (droplets); and various hydrated mesomorphic oriented lipid phases such as liquid crystalline and pseudocrystalline bilayer phases (L-alpha, L-beta, P-beta, Lc), interdigitated bilayer phases, and nonlamellar phases (inverted hexagonal H-I, H-II, cubic Pn3m) (see The Structure of Biological Membranes, ed. by P. Yeagle, CRC Press, Bora Raton, Fla., 1991, in particular ch. 1-5, incorporated herein by reference.). Lipidic microparticles include, but are not limited to a liposome, a lipid-nucleic acid complex, a lipid-drug complex, a solid lipid particle, and a microemulsion droplet. Methods of making and using these types of lipidic microparticles and nanoparticles, as well as attachment of affinity moieties, e.g., antibodies, to them are known in the art (see, e.g., U.S. Pat. Nos. 5,077,057; 5,100,591; 5,616,334; 6,406,713 (drug-lipid complexes); U.S. Pat. Nos. 5,576,016; 6,248,363; Bondi et al. (2003) *Drug Delivery* 10: 245-250; Pedersen et al. (2006) *Eur. J. Pharm. Biopharm.* 62: 155-162 (solid lipid particles); U.S. Pat. Nos. 5,534,502; 6,720,001; Shiokawa et al. (2005) *Clin. Cancer Res.* 11: 2018-2025 (microemulsions); U.S. Pat. No. 6,071,533 (lipid-nucleic acid complexes)).

Lipid particles also include liposomes. A liposome is generally defined as a particle comprising one or more lipid bilayers enclosing an interior, typically an aqueous interior. Thus, a liposome is often a vesicle formed by a bilayer lipid membrane. There are many methods for the preparation of liposomes. Some of them are used to prepare small vesicles (d<0.05 micrometer), some for larger vesicles (d>0.05 micrometer). Some are used to prepare multilamellar vesicles, some for unilamellar ones. In certain embodiments for the present invention, unilamellar vesicles are preferred because a lytic event on the membrane means the lysis of the entire vesicle. However, multilamellar vesicles can also be used, perhaps with reduced efficiency. Methods for liposome preparation are exhaustively described in several review articles such as Szoka and Papahadjopoulos (1980) *Ann. Rev. Biophys. Bioeng.*, 9: 467, Deamer and Uster (1983) Pp. 27-51 In: *Liposomes*, ed. M. J. Ostro, Marcel Dekker, New York, and the like.

In various embodiments, liposomes are composed of vesicle-forming lipids, generally including amphipathic lipids having both hydrophobic tail groups and polar head groups. A characteristic of a vesicle-forming lipid is its ability to either (a) form spontaneously into bilayer vesicles in water, as exemplified by the phospholipids, or (b) be stably incorporated into lipid bilayers, by having the hydrophobic portion in contact with the interior, hydrophobic region of the bilayer membrane, and the polar head group oriented toward the exterior, polar surface of the membrane. A vesicle-forming lipid for use in the present invention is any conventional lipid possessing one of the characteristics described above.

In certain embodiments the vesicle-forming lipids of this type are preferably those having two hydrocarbon tails or chains, typically acyl groups, and a polar head group. Included in this class are the phospholipids, such as phosphatidylcholine (PC), phosphatidylethanolamine (PE), phosphatidic acid (PA), phosphatidylglycerol (PG), and phosphatidylinositol (PI), where the two hydrocarbon chains are typically between about 14-22 carbon atoms in length, and have varying degrees of unsaturation. In certain embodiments preferred phospholipids include PE and PC. One illustrative PC is hydrogenated soy phosphatidylcholine (HSPC). Single chain lipids, such as sphingomyelin (SM), and the like can also be used.

The above-described lipids and phospholipids whose acyl chains have a variety of degrees of saturation can be obtained commercially, or prepared according to published methods. Other lipids that can be included in certain embodiments are sphingolipids and glycolipids. The term "sphingolipid" as used herein encompasses lipids having two hydrocarbon chains, one of which is the hydrocarbon chain of sphingosine. The term "glycolipids" refers to sphingolipids comprising also one or more sugar residues.

Lipids for use in the lipidic microparticles or nanoparticles contemplated herein can include relatively "fluid" lipids, meaning that the lipid phase has a relatively low lipid melting temperature, e.g., at or below room temperature, or alternately, relatively "rigid" lipids, meaning that the lipid has a relatively high melting point, e.g., at temperatures up to 50° C. As a general rule, the more rigid, i.e., saturated lipids, contribute to greater membrane rigidity in the lipid bilayer structure, and thus to more stable drug retention after active drug loading. In certain embodiments preferred lipids of this type are those having phase transition temperatures above about 37° C.

In various embodiments the liposomes may additionally include lipids that can stabilize a vesicle or liposome composed predominantly of phospholipids. An illustrative lipids of this group is cholesterol at levels between 25 to 45 mole percent.

In certain embodiments liposomes used in the chimeric constructs contain between 30-75 percent phospholipids, e.g., phosphatidylcholine (PC), 25-45 percent cholesterol. One illustrative liposome formulation contains 60 mole percent phosphatidylcholine and 40 mole percent cholesterol.

In various embodiments the liposomes can include a surface coating of a hydrophilic polymer chain. "Surface-coating" refers to the coating of any hydrophilic polymer on the surface of liposomes. The hydrophilic polymer is included in the liposome by including in the liposome composition one or more vesicle-forming lipids derivatized with a hydrophilic polymer chain. The vesicle-forming lipids which can be used are any of those described above for the first vesicle-forming lipid component, however, in certain embodiments, vesicle-forming lipids with diacyl chains, such as phospholipids, are preferred. One illustrative phospholipid is phosphatidylethanolamine (PE), which contains a reactive amino group convenient for coupling to the activated polymers. One illustrative PE is distearoyl PE (DSPE). Another example is non-phospholipid double chain amphiphilic lipids, such as diacyl- or dialkylglycerols, derivatized with a hydrophilic polymer chain.

In certain embodiments a hydrophilic polymer for use in coupling to a vesicle forming lipid is polyethyleneglycol (PEG), preferably as a PEG chain having a molecular weight between 1,000-10,000 Daltons, more preferably between 1,000-5,000 Daltons, most preferably between 2,000-5,000 Daltons. Methoxy or ethoxy-capped analogues of PEG are also useful hydrophilic polymers, commercially available in a variety of polymer sizes, e.g., 120-20,000 Daltons.

Other hydrophilic polymers that can be suitable include, but are not limited to polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethylcellulose.

Preparation of lipid-polymer conjugates containing these polymers attached to a suitable lipid, such as PE, have been described, for example in U.S. Pat. No. 5,395,619, which is expressly incorporated herein by reference, and by Zalipsky in STEALTH LIPOSOMES (1995). In certain embodiments, typically, between about 1-20 mole percent of the polymer-derivatized lipid is included in the liposome-forming components during liposome formation. Polymer-derivatized lipids suitable for practicing the invention are also commercially available (e.g. SUNBRITE®, NOF Corporation, Japan.).

In various embodiments the hydrophilic polymer chains provide a surface coating of hydrophilic chains sufficient to extend the blood circulation time of the liposomes in the absence of such a coating. The extent of enhancement of blood circulation time is severalfold over that achieved in the absence of the polymer coating, as described in U.S. Pat. No. 5,013,556, which is expressly incorporated herein by reference.

The liposomes may be prepared by a variety of techniques, such as those detailed in Szoka et al. (1980) *Ann. Rev. Biophys. Bioeng.* 9: 467, and a specific example of liposomes prepared in support of the present invention is set forth in Example 1. In certain embodiments the liposomes are multilamellar vesicles (MLVs), which can be formed by simple lipid-film hydration techniques. In this procedure, a mixture of liposome-forming lipids and including a vesicle-forming lipid derivatized with a hydrophilic polymer are dissolved in a suitable organic solvent which is evaporated in a vessel to form a dried thin film. The film is then covered by an aqueous medium to form MLVs, typically with sizes between about 0.1 to 10 microns. Illustrative methods of preparing derivatized lipids and of forming polymer-coated liposomes have been described in U.S. Pat. Nos. 5,013,556, 5,631,018 and 5,395,619, which are incorporated herein by reference.

After liposome formation, the vesicles may be sized to achieve a size distribution of liposomes within a selected range, according to known methods. In certain embodiments the liposomes are uniformly sized to a selected size range between 0.04 to 0.25 µm. Small unilamellar vesicles (SUVs), typically in the 0.04 to 0.08 µm range, can be prepared by extensive sonication or homogenization of the liposomes. Homogeneously sized liposomes having sizes in a selected range between about 0.08 to 0.4 microns can be produced, e.g., by extrusion through polycarbonate membranes or other defined pore size membranes having selected uniform pore sizes ranging from 0.03 to 0.5 microns, typically, 0.05, 0.08, 0.1, or 0.2 microns. The pore size of the membrane corresponds roughly to the largest size of liposomes produced by extrusion through that membrane, particularly where the preparation is extruded two or more times through the same membrane. The sizing is typically carried out in the original lipid-hydrating buffer, so that the liposome interior spaces retain this medium throughout the initial liposome processing steps.

In certain embodiments the liposomes are prepared to include an ion gradient, such as a pH gradient or an ammonium or amine ion gradient, across the liposome lipid bilayer in order to effect loading of the liposomes with a substance of interest, e.g., a pharmaceutical (drug). A liposome may also contain substances, such as polyvalent ions, reducing the rate of drug escape from the liposome. One method for preparing such liposomes loaded with a drug is set forth in U.S. Patent Publication 2007/0116753 which is incorporated herein by reference.

In one illustrative approach a mixture of liposome-forming lipids is dissolved in a suitable organic solvent and evaporated in a vessel to form a thin film. The film is then covered with an aqueous medium containing the solute species that will form the aqueous phase in the liposome interior spaces in the final liposome preparation. The lipid film hydrates to form multilamellar vesicles (MLVs), typically with heterogeneous sizes between about 0.1 to 10 microns. The liposome are then sized, as described above, to a uniform selected size range.

After sizing, the external medium of the liposomes is treated to produce an ion gradient across the liposome membrane, which is typically a lower inside/higher outside concentration gradient. This may be done in a variety of ways, e.g., by (i) diluting the external medium, (ii) dialysis against the desired final medium, (iii) molecular-sieve chromatography, e.g., using SEPHADEX G-50, against the desired medium, or (iv) high-speed centrifugation and resuspension of pelleted liposomes in the desired final medium. The external medium which is selected will depend on the mechanism of gradient formation and the external pH desired, as will now be considered.

In one approach for generating a pH gradient, the hydrated sized liposomes have a selected internal-medium pH. The suspension of the liposomes is titrated until a desired final pH is reached, or treated as above to exchange the external phase buffer with one having the desired external pH. For example, the original medium may have a pH of 5.5, in a selected buffer, e.g., glutamate or phosphate buffer, and the final external medium may have a pH of 8.5 in the same or different buffer. The internal and external media are preferably selected to contain about the same osmolarity, e.g., by suitable adjustment of the concentration of buffer, salt, or low molecular weight solute, such as sucrose.

In another approach, the proton gradient used for drug loading is produced by creating an ammonium ion gradient across the liposome membrane, as described, for example, in U.S. Pat. No. 5,192,549. Here the liposomes are prepared in an aqueous buffer containing an ammonium salt, typically 0.1 to 0.3 M ammonium salt, such as ammonium sulfate, at a suitable pH, e.g., 5.5 to 7.5. After liposome formation and sizing, the external medium is exchanged for one lacking ammonium ions, e.g., the same buffer but one in which ammonium sulfate is replaced by NaCl or a sugar that gives the same osmolarity inside and outside of the liposomes.

After liposome formation, the ammonium ions inside the liposomes are in equilibrium with ammonia and protons. Ammonia is able to penetrate the liposome bilayer and escape from the liposome interior. Escape of ammonia continuously shifts the equilibrium within the liposome toward the right, to production of protons.

While the foregoing discussion pertains to the formation of liposomes, similar lipids and lipid compositions can be used to form other lipidic microparticles or nanoparticles such as a solid lipid particle, a microemulsion, and the like.

Further, the liposomes may be prepared for attachment to EGFR affinity moieties (e.g. C10 mutant antibodies). Here the lipid component included in the liposomes would include either a lipid derivatized with the affinity moiety, or a lipid having a polar-head chemical group, e.g., on a linker, that can be derivatized with the targeting molecule in preformed liposomes, according to known methods.

Methods of functionalizing lipids and liposomes with affinity moieties such as antibodies are well known to those of skill in the art (see, e.g., DE 3,218,121; Epstein et al. (1985) *Proc. Natl. Acad. Sci.*, USA, 82:3688 (1985); Hwang et al. (1980) *Proc. Natl. Acad. Sci.*, USA, 77: 4030; EP 52,322; EP 36,676; EP 88,046; EP 143,949; EP 142,641; Japanese patent application 83-118008; U.S. Pat. Nos. 4,485,045 and 4,544,545; and EP 102,324, all of which are incorporated herein by reference). One illustrative method for attachment of proteinaceous affinity moieties to lipidic microparticles is described in U.S. Pat. No. 6,210,707.

b) Polymeric Microparticles or Nanoparticles and Micelles.

Microparticle and especially nanoparticle-based drug delivery systems have considerable potential for treatment of various pathologies. Technological advantages of polymeric microparticles or nanoparticles used as drug carriers are high stability, high carrier capacity, feasibility of incorporation of both hydrophilic and hydrophobic substances, and feasibility of variable routes of administration, including oral application and inhalation. Polymeric nanoparticles can also be designed to allow controlled (sustained) drug release from the matrix. These properties of nanoparticles enable improvement of drug bioavailability and reduction of the dosing frequency.

Polymeric nanoparticles are typically micron or submicron (<1 μm) colloidal particles. This definition includes monolithic nanoparticles (nanospheres) in which the drug is adsorbed, dissolved, or dispersed throughout the matrix and nanocapsules in which the drug is confined to an aqueous or oily core surrounded by a shell-like wall. Alternatively, in certain embodiments, the drug can be covalently attached to the surface or into the matrix.

Polymeric microparticles and nanoparticles are typically made from biocompatible and biodegradable materials such as polymers, either natural (e.g., gelatin, albumin) or synthetic (e.g., polylactides, polyalkylcyanoacrylates), or solid lipids. In the body, the drug loaded in nanoparticles is usually released from the matrix by diffusion, swelling, erosion, or degradation. One commonly used material is poly(lactide-co-glycolide) (PLG).

Methods of fabricating and loading polymeric nanoparticles or microparticles are well known to those of skill in the art. Thus, for example, Matsumoto et al. (1999) *Intl. J. Pharmaceutics*, 185: 93-101, teaches the fabrication of poly(L-lactide)-poly(ethylene glycol)-poly(L-lactide) nanoparticles, Chawla et al. (2002) *Intl. J. Pharmaceutics* 249: 127-138, teaches the fabrication and use of poly(ε-caprolactone) nanoparticles delivery of tamifoxen, and Bodmeier et al. (1988) *Intl. J. Pharmaceutics,* 43: 179-186, teaches the preparation of poly(D,L-lactide) microspheres using a solvent evaporation method. "Intl. J. Pharmaceutics, 1988, 43, 179-186. Other nanoparticle formulations are described, for example, by Williams et al. (2003) *J. Controlled Release,* 91: 167-172; Leroux et al. (1996) *J. Controlled Release,* 39: 339-350; Soppimath et al. (2001) *J. Controlled Release,* 70:1-20; Brannon-Peppas (1995) *Intl. J. Pharmaceutics,* 116: 1-9; and the like.

Another kind of nanoparticle suitable for the constructs described herein is a micelle. As used herein, a "micelle" refers to an aggregate of amphiphilic molecules in an aqueous medium, having an interior core and an exterior surface, wherein the amphiphilic molecules are predominantly oriented with their hydrophobic portions forming the core and hydrophilic portions forming the exterior surface. Micelles are typically in a dynamic equilibrium with the amphiphilic molecules or ions from which they are formed existing in solution in a non-aggregated form. Many amphiphilic compounds, including detergents, surfactants, amphiphilic polymers, lipopolymers (such as PEG-lipids), bile salts, single-chain phospholipids and other single-chain amphiphiles, and amphipathic pharmaceutical compounds are known to spontaneously form micelles in aqueous media above certain concentration, known as critical micellization concentration, or CMC. Unlike lipidic microparticles and nanoparticles, amphipathic, e.g., lipid, components of a micelle, as defined herein, do not form bilayer phases, nonbilayer mesophases, isotropic liquid phases or solid amorphous or crystalline phases. The concept of a micelle, as well as the methods and conditions for their formation, are well known to skilled in the art. Micelles can co-exist in solution with lipidic microparticles and nanoparticles (see, e.g., .Liposome Technology, Third Edition, vol. 1, ch. 11, p. 209-239, Informa, London, 2007). Micelles are useful in carrying and targeting pharmaceutical agents. The uses of micelles as carriers for pharmaceuticals as well as the methods of making pharmaceutical micelles and attachment to micelles of moieties having affinity to target cells and/or tissues, including affinity moieties binding to EGFR, are known in the art (see, e.g., Torchilin (2007) *Pharmaceutical Res.* 24: 1-16; Lukyanov and Torchilin (2004) *Adv. Drug Delivery Reviews* 56: 1273-1289; Torchilin et al. (2003) *Proc. Natl. Acad. Sci.*, USA, 100: 6039-6044; Zeng et al. (2006) *Bioconjugate Chemistry* 17: 399-409; Sutton et al. (2007) *Pharmaceutical Research* 24: 1029-1046; Lee et al. (2007) *Molecular Pharmacology*, 4: 769-781.

8) Viral Particles.

In certain embodiments, the effector comprises a viral particle (e.g., a filamentous phage, an adeno-associated virus (AAV), a lentivirus, and the like). The anti-MUC4 antibody can be conjugated to the viral particle and/or can be expressed on the surface of the viral particle (e.g. a filamentous phage). The viral particle can additionally include a nucleic acid that is to be delivered to the target (e.g., a pancreatic cancer) cell. The use of viral particles to deliver nucleic acids to cells is described in detail in WO 99/55720, U.S. Pat. No. 6,670,188, U.S. Pat. No. 6,642,051, and U.S. Pat. No. 6,669,936.

9) Ligands/Epitope Tads).

In certain embodiments, particular where an indirect targeting approach is to be used, the anti-MUC4 antibody is attached to an effector comprising an epitope tag. The terms "epitope tag" or "affinity tag" are used interchangeably herein, and refers to a molecule or domain of a molecule that is specifically recognized by an antibody or other binding partner. In certain embodiments the term can also refer to the binding partner complex as well. Thus, for example, avidin, streptavidin, biotin or a biotin/avidin complex regarded as an affinity tags. In addition to epitopes recognized in epitope/antibody interactions, affinity tags also comprise "epitopes" recognized by other binding molecules (e.g. ligands bound by receptors), ligands bound by other ligands to form heterodimers or homodimers, $His_6$ bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:4) epitope, c-myc antibodies (available from Sigma, St. Louis), the HNK-1 carbohydrate epitope, the HA epitope, the HSV epitope, the $His_4$ (SEQ ID NO:5), $His_5$ (SEQ ID NO:6), and $His_6$ (SEQ ID NO:7) epitopes that are recognized by the H is epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG® epitope (N-terminal, C-terminal or internal tagging), the c-myc epitope (C-terminal) or both the FLAG (N-terminal) and c-myc (C-terminal) epitopes.

Chimeric moieties utilizing such epitope tags as effector molecules can act as bifunctional linkers establishing an association between the cell(s) expressing MUC4 and constructs bearing the binding partner for the epitope tag and another effector (e.g., a radionuclide, a cytotoxin, etc.).

10) Therapeutic Moieties.

In various embodiments the effector comprises a therapeutic agent (e.g., an anti-cancer drug or other moiety). In certain embodiments the anti-MUC4 antibodies can be conjugated to a drug (e.g., a cytotoxic, cytostatic, anti-angiogenic, or immunomodulatory agent). The conjugates can be used therapeutically or prophylactically, e.g., the anti-MUC4 antibody can target the drug, to a cancer cell (e.g., a tumor or site or metastatic cell) such that the drug affects the target cell(s) (e.g., causes a cytostatic or cytotoxic effect on targeted cells).

In some embodiments, the anti-MUC4 antibody itself has therapeutic or prophylactic efficacy (e.g., the antibody can cause a cytostatic or cytotoxic effect on a cell that expresses (or overexpresses MUC4) (e.g., an endothelial cell or tumor cell)). In certain embodiments the antibody-drug conjugate can be used such that the antibody and drug both contribute (e.g., additively or synergistically) to an effect on the target cell(s). The drug and/or binding protein can be, for example, cytotoxic, cytostatic or otherwise prevent or reduce the ability of a targeted cell to divide and/or survive (e.g., when the drug is taken up or internalized by the targeted cell and/or upon binding of the antibody to the surface of the target cell(s). For example, in certain embodiments the drug and/or antibody can prevent or reduce the ability of the cell to divide and/or metastasize.

Useful classes of drugs that can be used in the antibody-drug conjugates described herein include, but are not limited to cytotoxic or immunomodulatory agents such as, for example, antitubulin agents, auristatins, DNA minor groove binders, DNA replication inhibitors, alkylating agents (e.g., platinum complexes such as cis-platin, mono(platinum), bis (platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

One useful class of anti-cancer pharmaceutical includes the retinoids. Retinoids are useful in treating a wide variety of epithelial cell carcinomas, including, but not limited to pulmonary, head, neck, esophagus, adrenal, prostate, ovary, testes, pancreas, and gut.

Retinoic acid, analogues, derivatives, and mimetics are well known to those of skill in the art. Such retinoids include, but are not limited to retinoic acid, ceramide-generating retinoid such as fenretinide (see, e.g., U.S. Pat. No. 6,352,844), 13-cis retinoic acid (see, e.g., U.S. Pat. Nos. 6,794,416, 6,339, 107, 6,177,579, 6,124,485, etc.), 9-cis retinoic acid (see, e.g., U.S. Pat. Nos. 5,932,622, 5,929,057, etc.), 9-cis retinoic acid esters and amides (see, e.g., U.S. Pat. No. 5,837,728), 11-cis retinoic acid (see, e.g., U.S. Pat. No. 5,719,195), all trans retinoic acid (see, e.g., U.S. Pat. Nos. 4,885,311, 4,994,491, 5,124,356, etc.), 9-(Z)-retinoic acid (see, e.g., U.S. Pat. Nos. 5,504,230, 5,424,465, etc.), retinoic acid mimetic anlides (see, e.g., U.S. Pat. No. 6,319,939), ethynylheteroaromatic-acids having retinoic acid-like activity (see, e.g., U.S. Pat. Nos. 4,980,484, 4,927,947, 4,923,884 Ethynylheteroaromatic-acids having retinoic acid-like activity, U.S. Pat. No. 4,739,098, etc.) aromatic retinoic acid analogues (see, e.g., U.S. Pat. No. 4,532,343), N-heterocyclic retinoic acid analogues (see, e.g., U.S. Pat. No. 4,526,7874), naphtenic and heterocyclic retinoic acid analogues (see, e.g., U.S. Pat. No. 518,609), open chain analogues of retinoic acid (see, e.g., U.S. Pat. No. 4,490,414), entaerythritol and monobenzal acetals of retinoic acid esters (see, e.g., U.S. Pat. No. 4,464, 389), naphthenic and heterocyclic retinoic acid analogues (see, e.g., U.S. Pat. No. 4,456,618), azetidinone derivatives of retinoic acid (see, e.g., U.S. Pat. No. 4,456,618), and the like.

In various embodiments the retinoic acid, retinoic acid analogue, derivative, or mimetics can be coupled (e.g., conjugated) to the anti-MUC4 antibody or it can be contained within a liposome or complexed with a lipid or a polymeric nanoparticle that is coupled to the targeting moiety, e.g. as described herein.

In certain embodiments the methods and compositions of this invention can be used to deliver other cancer therapeutics instead of or in addition to the retinoic acid or retinoic acid analogue/derivative. Such agents include, but are not limited to alkylating agents (e.g., mechlorethamine (Mustargen), cyclophosphamide (Cytoxan, Neosar), ifosfamide (Ifex), phenylalanine mustard; melphalen (Alkeran), chlorambucol (Leukeran), uracil mustard, estramustine (Emcyt), thiotepa (Thioplex), busulfan (Myerlan), lomustine (CeeNU), carmustine (BiCNU, BCNU), streptozocin (Zanosar), dacarbazine (DTIC-Dome), cis-platinum, cisplatin (Platinol, Platinol AQ), carboplatin (Paraplatin), altretamine (Hexylen), etc.), antimetabolites (e.g. methotrexate (Amethopterin, Folex, Mexate, Rheumatrex), 5-fluoruracil (Adrucil, Efudex, Fluoroplex), floxuridine, 5-fluorodeoxyuridine (FUDR), capecitabine (Xeloda), fludarabine: (Fludara), cytosine arabinoside (Cytaribine, Cytosar, ARA-C), 6-mercaptopurine (Purinethol), 6-thioguanine (Thioguanine), gemcitabine (Gemzar), cladribine (Leustatin), deoxycoformycin; pentostatin (Nipent), etc.), antibiotics (e.g. doxorubicin (Adriamycin, Rubex, Doxil, Daunoxome-liposomal preparation), daunorubicin (Daunomycin, Cerubidine), idarubicin (Idamycin), valrubicin (Valstar), mitoxantrone (Novantrone), dactinomycin (Actinomycin D, Cosmegen), mithramycin, plicamycin (Mithracin), mitomycin C (Mutamycin), bleomycin (Blenoxane), procarbazine (Matulane), etc.), mitotic inhibitors (e.g. paclitaxel (Taxol), docetaxel (Taxotere), vinblatine sulfate (Velban, Velsar, VLB), vincristine sulfate (Oncovin, Vincasar PFS, Vincrex), vinorelbine sulfate (Navelbine), etc.), chromatin function inhibitors (e.g., topotecan (Camptosar), irinotecan (Hycamtin), etoposide (VP-16, VePesid, Toposar), teniposide (VM-26, Vumon), etc.), hormones and hormone inhibitors (e.g. diethylstilbesterol (Stilbesterol, Stilphostrol), estradiol, estrogen, esterified estrogens (Estratab, Menest), estramustine (Emcyt), tamoxifen (Nolvadex), toremifene (Fareston) anastrozole (Arimidex), letrozole (Femara), 17-OH-progesterone, medroxyprogesterone, megestrol acetate (Megace), goserelin (Zoladex), leuprolide (Leupron), testosteraone, methyltestosterone, fluoxmesterone (Android-F, Halotestin), flutamide (Eulexin), bicalutamide (Casodex), nilutamide (Nilandron), etc.), inhibitors of synthesis (e.g., aminoglutethimide (Cytadren), ketoconazole (Nizoral), etc.), immunomodulators (e.g., rituximab (Rituxan), trastuzumab (Herceptin), denileukin diftitox (Ontak), levamisole (Ergamisol), *bacillus* Calmette-Guerin, BCG (TheraCys, TICE BCG), interferon alpha-2a, alpha 2b (Roferon-A, Intron A), interleukin-2, aldesleukin (ProLeukin), etc.) and other agents such as 1-aspariginase (Elspar, Kidrolase), pegaspasgase (Oncaspar), hydroxyurea (Hydrea, Doxia), leucovorin (Wellcovorin), mitotane (Lysodren), porfimer (Photofrin), tretinoin (Veasnoid), and the like. An illustrative list of anti-cancer agents (drugs) organized by function is shown in Table 3.

TABLE 3

Illustrative, but non-limiting list of various anti-cancer agents contemplated for incorporation in the effector(s) described herein and/or for administration in conjunction with the anti-MUC4 antibodies and/or anti-MUC4 antibodies attached to an effector (chimeric constructs) described herein.

| | | |
|---|---|---|
| Antibodies | IGF-1R (insulin-like growth factor type 1 receptor) is expressed on the cell surface of most human cancers. | A12 (fully humanized mAb) 19D12 (fully humanized mAb) CP751-871 (fully humanized mAb) H7C10 (humanized mAb) alphaIR3 (mouse) scFV/FC (mouse/human chimera) EM/164 (mouse) AMG 479 (fully humanized mAb; Amgen) IMCA 12 (fully humanized mAb; Imclone) NSC-742460 (Dyax) MR-0646, F50035 (Pierre Fabre Medicament, Merck) |
| | Antibodies that bind EGFR (epidermal growth factor receptor); Mutations affecting EGFR expression or activity could result in cancer | Matuzumab (EMD72000) Erbitux ®/Cetuximab (Imclone) Vectibix ®/Panitumumab (Amgen) mAb 806 Nimotuzumab (TheraCIM) INCB7839 (Incyte) Matuzumab (EMD72000) Panitumumab (Vectibix ®; Amgen) |
| | Antibodies that bind cMET (Mesenchymal epithelial transition factor); a member of the MET family of receptor tyrosine kinases) antibodies | AVEO (AV299) (AVEO) AMG102 (Amgen 5D5 (OA-5D5) (Genentech) |
| | Anti-ErbB3 antibodies which bind different epitopes | Ab #14 (MM 121-14) 1B4C3; 2D1D12 (U3 Pharma AG) U3-1287/AMG888 (U3 Pharma/Amgen) |
| | Anti-ErbB2 (HER) antibodies | Herceptin (trastuzumab; Genentech/Roche); Omnitarg (pertuzumab; 2C4, R1273; Genentech/Roche) |
| Small Molecules Targeting IGF1R | IGF1R growth factor type 1 receptor), is expressed on the cell surface of most human cancers | NVP-AEW541-A BMS-536,924 (1H-benzoimidazol 2 yl) 1H pyridin-2-one) BMS-554,417 Cycloligan TAE226 PQ401 |

TABLE 3-continued

Illustrative, but non-limiting list of various anti-cancer agents contemplated for incorporation in the effector(s) described herein and/or for administration in conjunction with the anti-MUC4 antibodies and/or anti-MUC4 antibodies attached to an effector (chimeric constructs) described herein.

| | | |
|---|---|---|
| Small Molecules Targeting EGFR receptor | Mutations affecting EGFR expression or activity can result in cancer | Iressa ®/Gefitinib (AstraZeneca)<br>CI-1033 (PD 183805) (Pfizer)<br>Lapatinib (GW-572016) (GlaxoSmithKline)<br>Tykerb ®/Lapatinib Ditosylate (SmithKline Beecham)<br>Tarceva ®/Erlotinib HCL (OSI-774) (OSI Pharma)<br>PKI-166 (Novartis)<br>PD-158780<br>EKB-569<br>Tyrphostin AG 1478(4-(3-Chloroanillino)-6,7-dimethoxyquinazoline) |
| Small Molecules Targeting ErbB2 | ErbB2 (HER2) is a member of the ErbB family of receptors, which is expressed on certain cancer cells | HKI-272 (neratinib; Wyeth)<br>KOS-953 (tanespimycin; Kosan Biosciences) |
| Small molecules Targeting cMET | cMET (Mesenchymal epithelial transition factor) is a member of the MET family of receptor tyrosine kinases) | PHA665752<br>ARQ 197 (ArQule)<br>ARQ-650RP (ArQule) |
| Antimetabolites | An antimetabolite is a chemical with a similar structure to a substance (a metabolite) required for normal biochemical reactions, yet different enough to interfere with the normal functions of cells, including for example cell division. | Flourouracil (5-FU)<br>Capecitabine/XELODA (HLR Roche)<br>5-Trifluoromethyl-2'-deoxyuridine<br>Methotrexate sodium (Trexall) (Barr)<br>Raltitrexed/Tomudex (AstraZaneca)<br>Pemetrexed/Alimta ® (Lilly) Tegafur<br>Cytosine Arabinoside (Cytarabine, Ara-C)/Thioguanine (GlaxoSmithKline) 5-azacytidine<br>6-mercaptopurine (Mercaptopurine, 6-MP)<br>Azathioprine/Azasan (AAIPHARMA LLC)<br>6-thioguanine (6-TG)/Purinethol (TEVA)<br>Pentostatin/Nipent (Hospira Inc.)<br>Fludarabine phosphate/Fludara ® (Bayer Health Care)<br>Cladribine (2-CdA, 2-chlorodeoxyadenosine)/Leustatin (Ortho Biotech)<br>Floxuridine (5-fluoro-2)/FUDR (Hospira, Inc.) |
| Alkylating agents | An alkylating antineoplastic agent is an alkylating agent that attaches an alkyl group to DNA. Since cancer cells generally proliferate more than healthy cells they are more sensitive to DNA damage. and alkylating agents are used clinically to treat a variety of tumours. | Ribonucleotide Reductase Inhibitor (RNR)<br>Cyclophosphamide/Cytoxan (BMS)<br>Neosar (TEVA)<br>Ifosfamide/Mitoxana (ASTA Medica)<br>Thiotepa (Bedford, Abraxis, Teva)<br>BCNU -- 1,3-bis(2-chloroethyl)-1-nitosourea<br>CCNU -- 1,-(2-chloroethyl)-3-cyclohexyl-lnitrosourea<br>(methyl CCNU)<br>Hexamethylmelamine (Altretamine, HMM)/Hexalen (MGI Pharma Inc.)<br>Busulfan/Myleran (GlaxoSmithKline)<br>Procarbazine HCL/Matulane (Sigma Tau Pharmaceuticals, Inc.)<br>Dacarbazine (DTIC)<br>Chlorambucil/Leukaran ® (SmithKline Beecham)<br>Melphalan/Alkeran (GlaxoSmithKline)<br>Cisplatin (Cisplatinum, CDDP)/Platinol (Bristol Myers)<br>Carboplatin/Paraplatin (BMS)<br>Oxaliplatin/Eloxitan (Sanofi-Aventis US)<br>Bendamustine<br>Carmustine<br>Chloromethine<br>Dacarbazine (DTIC)<br>Fotemustine<br>Lomustine<br>Mannosulfan<br>Nedaplatin<br>Nimustine<br>Prednimustine |

TABLE 3-continued

Illustrative, but non-limiting list of various anti-cancer agents contemplated for incorporation in the effector(s) described herein and/or for administration in conjunction with the anti-MUC4 antibodies and/or anti-MUC4 antibodies attached to an effector (chimeric constructs) described herein.

| | | |
|---|---|---|
| | | Ranimustine |
| | | Satraplatin |
| | | Semustine |
| | | Streptozocin |
| | | Temozolomide |
| | | Treosulfan |
| | | Triaziquone |
| | | Triethylene melamine |
| | | ThioTEPA (Bedford, Abraxis, Teva) |
| | | Triplatin tetranitrate |
| | | Trofosfamide |
| | | Uramustine |
| Topoisomerase inhibitors | Topoisomerase inhibitors are chemotherapy agents designed to interfere with the action of topoisomerase enzymes (topoisomerase I and II). These enzymes control the changes in DNA structure by catalyzing the breaking and rejoining of the phosphodiester backbone of DNA strands during the normal cell cycle. | Doxorubicin HCL/Doxil (Alza) Daunorubicin citrate/Daunoxome ® (Gilead) Mitoxantrone HCL/Novantrone (EMD Serono) Actinomycin D Etoposide/Vepesid (BMS)/Etopophos (Hospira, Bedford, Teva Parenteral, etc.) Topotecan HCL/Hycamtin (GlaxoSmithKline) Teniposide (VM-26)/Vumon (BMS) Irinotecan HCL(CPT-11)/ Camptosar ® (Pharmacia & Upjohn) Camptothecin (CPT) Belotecan Rubitecan |
| Microtubule targeting agents | Microtubules are one of the components of the cytoskeleton. Microtubules serve as structural components within cells and are involved in many cellular processes including mitosis, cytokinesis, and vesicular transport. | Vincristine/Oncovin ® (Lilly) Vinblastine sulfate/Velbane (discontinued) (Lilly) Vinorelbine tartrate/Navelbine (PierreFabre) Vindesine sulphate/Eldisine ® (Lilly) Paclitaxel/Taxol (BMS) Docetaxel/Taxotere (Sanofi Aventis US) Nanoparticle paclitaxel (ABI-007)/ Abraxane (Abraxis BioScience, Inc.) Ixabepilone/IXEMPRA TM (BMS) Larotaxel Ortataxel Tesetaxel Vinflunine |
| Kinse inhibitors | Tyrosine kinases are enzymes within the cell that function to attach phosphate groups to the amino acid tyrosine. By blocking the ability of protein tyrosine kinases to function, these compounds provide a tool for controlling cancerous cell growth | Imatinib mesylate/Gleevec (Novartis) Sunitinib malate/Sutent ® (Pfizer) Sorafenib tosylate/Nexavar ® (Bayer) Nilotinib hydrochloride monohydrate/ Tasigna (Novartis) AMG 386 (Amgen) Axitinib (AG-013736; Pfizer, Inc.) Bosutinib (SKI-606; Wyeth) Brivanib alalinate (BMS-582664; BMS) Cediranib (AZD2171; Recentin, AstraZeneca) Dasatinib (BMS-354825: Sprycel e; BMS) Lestaurtinib (CEP-701; Cephalon) Motesanib diphosphage (AMG-706; Amgen/Takeda) Pazopanib HCL (GW786034; Armala, GSK) Semaxanib (5U5416; Pharmacia) Vandetanib (AZD647; Zactima; AstraZeneca) Vatalanib (PTK-787; Novartis, Bayer Schering Pharma) XL184 (NSC718781; Exelixis, GSK) |
| Protein sysnthesis inhibitors | Induces cell apoptosis | L-asparaginase/Elspar ® (Merck & Co.) |
| Somatostatin analog | | Octreotide acetate (Sandostatin (X; Novartis) |
| Immunotherapeutic agents | Induces cancer patients to exhibit immune responsiveness | Alpha interferon Angiogenesis Inhibitor/Avastin (Genentech) IL-2 -- Interleukin 2 (Aldesleukin)/Proleukin (Chiron) IL-12 -- Interleukin 12 |

TABLE 3-continued

Illustrative, but non-limiting list of various anti-cancer agents contemplated for incorporation in the effector(s) described herein and/or for administration in conjunction with the anti-MUC4 antibodies and/or anti-MUC4 antibodies attached to an effector (chimeric constructs) described herein.

| | | |
|---|---|---|
| | Hormone therapy as a cancer treatment either reduces the level of specific hormones or alters the cancer's ability to use these hormones to grow and spread. | Toremifene citrate/Fareston (GTX, Inc.) Fulvestrant/Faslodex (AstraZeneca) Raloxifene HCL/Evista ® (Lilly) Anastrazole/Arimidex (AstraZeneca) Letrozole/Femara (Novartis) Fadrozole (CGS 16949A) Exemestane/Aromasin ® (Pharmacia & Upjohn) Leuprolide acetate/Eligard (QTL USA) Lupron (TAP Pharm.) Goserelin acetate/Zoladex (AstraZeneca) Triptorelin pamoate/Trelstar ® (Watson Labs) Buserelin/Suprefact (Sanofi Aventis) Nafarelin Cetrorelix/Cetrotide (EMD Serono) Bicalutamide/Casodex (AstraZeneca) Nilutamide/Nilandron (Aventis Pharm.) Megestrol acetate/Megace (BMS) Somatostatin Analogs (Octreotide acetate/Sandostatin (Novartis)) Abarelix (Plenaxis; Amgen) Abiraterone acetate (CB7630; BTG plc) Afimoxifene (TamoGel; Ascend Therapeutics, Inc.) Aromatase inhibitor (Atamestane plus toremifene; Intarcia Therapeutics, Inc.) Arzoxifene (Eli Lilly & Co) Asentar; DN-101 (Novartis; Oregon Health & Science U) Flutamide (Eulexin ®, Schering; Prostacur, Laboratories Almirall, S.A) Letrozole (CGS20267) (Femara, Chugai; Estrochek, Jagsonpal Pharmaceuticals Ltd;) Magestrol acetate (Estradiol Valerate (Delestrogen) Jagsonpal Pharmaceuticals Ltd) Medroxyprogesterone acetate (Veraplex; Combiphar) MT206 (Medisyn Technologies, Inc.) Nandrolone decanoate (Zestabolin; Mankind Pharma Ltd) Tamoxifen (Taxifen, Yung Shin Pharmaceutical; Tomifen, Alkem Laboratories Ltd.) Tamoxifen citrate (Nolvadex, AstraZeneca; Soltamox, EUSA Pharma Inc; Tamoxifen citrate SOPHARMA, Sopharma JSCo.) |
| Glucocorticoids | Anti-inflammatory drugs used to reduce swelling that causes cancer pain | Predinsolone Dexamethasone/Decadron (Wyeth) Prednisone (Deltasone, Orasone, Liquid Pred, Sterapred (X) |
| Aromatose inhibitors mTOR inhibitors | Includes imidazoles The mTOR signaling pathway was originally discovered during studies of the immunosuppressive agent rapamycin. This highly conserved pathway regulates cell proliferation and metabolism in response to environmental factors, linking cell growth factor receptor signaling via phosphoinositide-3-kinase (PI-3K) to cell | Ketoconazole Sirolimus (Rapamycin)/Rapamune (Wyeth) Temsirolimus (CCI-779)/Torisel (Wyeth) Deforolimus (AP23573) (Ariad Pharm.) Everolimus (RAD001)/Certican (Novartis) |

TABLE 3-continued

Illustrative, but non-limiting list of various anti-cancer agents contemplated for incorporation in the effector(s) described herein and/or for administration in conjunction with the anti-MUC4 antibodies and/or anti-MUC4 antibodies attached to an effector (chimeric constructs) described herein.

| | | |
|---|---|---|
| | growth, proliferation, and angiogenesis. | |
| Chemotherapeutic agents | | Adriamycin, 5-Fluorouracil, Cytoxin, Bleomycin, Mitomycin C, Daunomycin, Carminomycin, Aminopterin, Dactinomycin, Mitomycins, Esperamicins, Clofarabine, Mercaptopurine, Pentostatin, Thioguanine, Cytarabine, Decitabine, Floxuridine, Gemcitabine (Gemzar), Enocitabine, Sapacitabine |
| Protein Kinase B (PKB) inhibitors | | Akt Inhibitor ASTEX (Astex Therapeutics) Akt Inhibitors NERVIANO (Nerviano Medical Sciences) AKT Kinase Inhibitor TELIK (Telik Inc) AKT DECIPHERA (Deciphera Pharmaceuticals, LLC) Perifosine (KRX0401, D-21266; Keryx Biopharmaceuticals Inc, AEterna Zentaris Inc) Perifosine with Docetaxel (Keryx Biopharmaceuticals Inc, AEterna Zentaris Inc) Perifosine with Gemcitabine (AEterna Zentaris Inc) Perifosine with Paclitaxel (AEterna Zentaris Inc) Protein Kinase-B inhibitor DEVELOGEN (DeveloGen AG) PX316 (Oncothyreon, Inc.) RX0183 (Rexahn Pharmaceuticals Inc) RX0201 (Rexahn Pharmaceuticals Inc) VQD002 (VioQuest Pharmaceuticals Inc) XL418 (Exelixis Inc) ZEN027 (AEterna Zentaris Inc) |
| Phosphatidylinositol 3-Kinase (PI3K) Inhibitors | | BEZ235 (Novartis AG) BGT226 (Novartis AG) CAL101 (Calistoga Pharmaceuticals, Inc.) CHR4432 (Chroma Therapeutics Ltd) Erk/PI3K Inhibitors ETERNA (AEterna Zentaris Inc) GDC0941 (Genentech Inc/Piramed Limited/Roche Holdings Ltd) Enzastaurin HCL (LY317615; Enzastaurin; Eli Lilly) LY294002/Wortmannin PI3K Inhibitors SEMAFORE (Semafore Pharmaceuticals) PX866 (Oncothyreon, Inc.) SF1126 (Semafore Pharmaceuticals) VMD-8000 (VM Discovery, Inc.) XL147 (Exelixis Inc) XL147 with XL647 (Exelixis Inc) XL765 (Exelixis Inc) PI-103 (Roche/Piramed) |
| Cyclin dependent kinase inhibitors | | CYC200, r-roscovitine (Seliciclib; Cyclacel Pharma) NSC-649890, L86-8275, HMR-1275 (Alvocidib; NCI) |
| TLr9, CD289 | | IMOxine (Merck KGaA) HYB2055 (Idera) IMO-2055 (Isis Pharma) 1018 ISS (Dynavax Technologies/UCSF) PF-3512676 (Pfizer) |
| Enzyme Inhibitor | | Lonafarnib(SCH66336; Sarasar; SuperGen, U Arizona) |
| Anti-TRAIL | | AMG-655 (Aeterna Zentaris, Keryx Biopharma) Apo2L/TRAIL, AMG951 (Genentech, Amgen) Apomab (fully humanized mAb; Genentech) |
| MEK Inhibitors | [Mitogen-Activated Protein Kinase Kinase 1 (MAP2K1); Mitogen Activated Protein | ARRY162 (Array BioPharma Inc) ARRY704 (Array BioPharma Inc) ARRY886 (Array BioPharma Inc) AS703026 (Merck Serono S.A) |

TABLE 3-continued

Illustrative, but non-limiting list of various anti-cancer agents contemplated for incorporation in the effector(s) described herein and/or for administration in conjunction with the anti-MUC4 antibodies and/or anti-MUC4 antibodies attached to an effector (chimeric constructs) described herein.

| | | |
|---|---|---|
| | Kinase | AZD6244 (AstraZeneca Plc) |
| | Kinase 2 (MAP2K2)] | AZD8330 (AstraZeneca Plc) |
| | | RDEA119 (Ardea Biosciences, Inc.) |
| | | RDEA436 (Ardea Biosciences, Inc.) |
| | | XL518 (Exelixis Inc; Genentech Inc) |
| Other Inhibitors | | Imprime PGG (Biothera) |
| | | CHR-2797 (AminopeptidaseM1 inhibitor; Chroma Therapeutics) |
| | | E7820, NSC 719239 (Integrin-alpha2 inhibitor, Eisai) |
| | | INCB007839 (ADAM 17, TACE Inhibitor; Incyte) |
| | | CNF2024, BIIB021 (Hsp90 Inhibitor; Biogen Idec) |
| | | MP470, HPK-56 (Kit/Mel/Ret Inhibitor; Shering-Plough) |
| | | SNDX-275/MS-275 (HDAC Inhibitor; Syndax) |
| | | Zarnestra, Tipifarnib, R115777 (Ras Inhibitor; Janssen Pharma) |
| | | Volociximab; Eos 200-4, M200 (alpha581 integrin inhibitor; Biogen Idec; Eli Lilly/UCSF/PDL BioPharma) |
| | | Apricoxib (TP2001; COX-2 Inhibitor, Daiichi Sankyo; Tragara Pharma) |

In certain embodiments the cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluorodeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbazine, rapamycin (Sirolimus), streptozotocin, tenoposide, 6-thioguanine, thioTEPA, topotecan, vinblastine, vincristine, vinorelbine, VP-16 and VM-26. In certain embodiments the drugs include, but are not limited to, abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antisense molecule, an SiRNA, and the like. In certain embodiments the drugs include one or more drugs shown in Table 3.

In certain embodiments the drugs include one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

In various embodiments the drug can be provided in an encapsulation/containment/carrier moiety for attachment to the antibody, e.g., as described herein. Such systems/moietieis include, but are not limited to, lipids, liposomes, polymeric particles, chelates, viral capsids, and the like e.g., as described herein.

B) Attachment of the Antibody to the Effector.

One of skill will appreciate that the antibodies described herein and the effector molecule(s) can be joined together in any order. Thus, the effector can be joined to either the amino or carboxy termini of the antibody. The targeting molecule can also be joined to an internal region of the effector molecule, or conversely, the effector molecule can be joined to an internal location of the targeting molecule, as long as the attachment does not interfere with the respective activities of the molecules.

The antibody and the effector can be attached by any of a number of means well known to those of skill in the art. In certain embodiments, the effector is conjugated, either directly or through a linker (spacer), to the targeting molecule. However, In certain embodiments, where both the effector molecule and the antibody are polypeptides the chimeric construct, or a portion thereof, can be recombinantly expressed as a single-chain fusion protein.

1) Chemical Conjugation of the Effector to the Antibody.

In one embodiment, the anti-MUC4 antibody is chemically conjugated to the effector (e.g., a cytotoxin, a label, a ligand, or a drug or liposome, etc.). Means of chemically conjugating molecules are well known to those of skill.

The procedure for attaching an effector to the antibody will vary according to the chemical structure of the effector and/or antibody. Polypeptides typically contain variety of functional groups; e.g., carboxylic acid (COOH) or free amine ($-NH_2$) groups, that are available for reaction with a suitable functional group on an effector molecule to bind the effector thereto.

Alternatively, the antibody and/or the effector can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

A bifunctional linker having one functional group reactive with a group on a particular agent, and another group reactive with an antibody, may be used to form the desired immunoconjugate. In certain embodiments, derivatization can involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann (1991) *Science,* 252: 1657, U.S. Pat. Nos. 4,545,985 and 4,894,443.

In some circumstances, it is desirable to free the effector from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, which are known to hydrolyze dipeptide drug derivatives resulting in the release of active drug inside target cells (see, e.g., Dubowchik and Walker (1999) *Pharm. Therapeutics* 83:67-123). In some embodiments, peptidyl linkers are cleavable by enzymes that are present in targeted cells (e.g., cancer cells). For example, a peptidyl linker that is cleavable by the thiol-dependent protease cathepsin-B, which is highly expressed in cancerous tissue, can be used (e.g., a Phe-Leu or a Gly-Phe-Leu-Gly (SEQ ID NO:8) linker). Other such linkers are described, e.g., in U.S. Pat. No. 6,214,345. In some embodiments, the peptidyl linker cleavable by an intracellular protease is a Val-Cit (vc) linker or a Phe-Lys linker (fk) (see, e.g., U.S. Pat. No. 6,214,345, which describes the synthesis of doxorubicin with the val-cit linker). One advantage of using intracellular proteolytic release of the drug is that the drug can be attenuated when conjugated and the serum stabilities of the conjugates are typically high.

In some embodiments, the cleavable linker is pH-sensitive, i.e., sensitive to hydrolysis at certain pH values. For example, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal., ketal., or the like) can be used (see, e.g., U.S. Pat. Nos. 5,122,368; 5,824,805; 5,622,929; Dubowchik and Walker (1999) *Pharm. Therapeutics* 83: 67-123; Neville et al. (1989) *Biol. Chem.* 264: 14653-14661, and the like). Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet another embodiment, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (see, e.g., Thorpe et al. (1987) *Cancer Res.* 47: 5924-5931; Wawrzynczak et al. (1987) *In Immunoconjugates: Antibody Conjugates in Radioimagery and Therapy of Cancer*, C. W. Vogel ed., Oxford U. Press; U.S. Pat. No. 4,880,935, and the like).

In certain embodiments the linker is a malonate linker (see, e.g., Johnson et al. (1995) *Anticancer Res.* 15:1387-1393), a maleimidobenzoyl linker (see, e.g. Lau et al. (1995) *Bioorg-Med-Chem.* 3(10): 1299-1304), or a 3'-N-amide analog (see, e.g., Lau et al. (1995) *Bioorg-Med-Chem.* 3(10):1305-1312, and the like).

In some embodiments, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of a binding protein-drug conjugate, are cleaved when the binding protein-drug conjugate is present in an extracellular environment (e.g., in plasma). Whether a linker is not substantially sensitive to the extracellular environment can be determined, for example, by incubating independently with plasma both (a) the binding protein-drug conjugate (the "conjugate sample") and (b) an equal molar amount of unconjugated binding protein or drug (the "control sample") for a predetermined time period (e.g., 2, 4, 8, 16, or 24 hours) and then comparing the amount of unconjugated binding protein or drug present in the conjugate sample with that present in control sample, as measured, for example, by high performance liquid chromatography.

In other, non-mutually exclusive embodiments, the linker promotes cellular internalization. In certain embodiments, the linker promotes cellular internalization when conjugated to the drug (e.g., in the milieu of the linker-drug moiety of the binding protein-drug conjugate described herein). In yet other embodiments, the linker promotes cellular internalization when conjugated to both the drug and the anti-MUC4 antibody.

A variety of linkers that can be used with the present compositions and methods are described in WO 2004010957.

2) Conjugation of Chelates.

In certain embodiments, the effector comprises a chelate that is attached to an antibody or to an epitope tag. The anti-MUC4 antibody bears a corresponding epitope tag or antibody so that simple contacting of the antibody to the chelate results in attachment of the antibody with the effector. The combining step can be performed before the moiety is used (targeting strategy) or the target tissue can be bound to the antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

3) Expression as a Fusion Protein.

Where the effector comprises a protein, the chimeric construct (or a portion thereof) can be expressed as a fusion protein in which the protein component of the effector is fused directly, or through a peptide linker (e.g., a $(Gly_4Ser)_3$ (SEQ ID NO:9) linker, a $Gly_3$ linker, etc.) to the amino or carboxyl terminus of a component of the anti-MUC4 peptide. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins can be prepared by any suitable method, including, for example, cloning and restriction of appropriate sequences or direct chemical synthesis by methods such as the phosphotriester method of Narang et al. (1970) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; the solid support method of U.S. Pat. No. 4,458,066, and the like.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence. In certain embodiments DNA encoding fusion proteins may be cloned using DNA amplification methods such as polymerase chain reaction (PCR). Thus, for example, a nucleic acid encoding an anti-MUC4 antibody may be amplified from a nucleic acid template (clone) using a sense primer containing a first restriction site and an antisense primer containing a second restriction site. This produces a nucleic acid encoding the mature antibody sequence and having terminal restriction sites. A cytotoxin (or other polypeptide effector) may be cut out of a plasmid encoding that effector using restriction enzymes to produce cut ends suitable for annealing to the anti-MUC4 antibody. Ligation of the sequences and introduction of the construct into a vector produces a vector encoding the anti-MUC4-effector molecule fusion protein. Such PCR cloning methods are well known to those of skill in the art (see, for example, Debinski et al. *Int. J. Cancer,* 58: 744-748 (1994), for an example of the preparation of a PE fusion protein).

While the two molecules may be directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity. One of skill will appreciate that PCR primers may be selected to introduce an amino acid linker or spacer between the antibody and the effector molecule if desired.

The nucleic acid sequences encoding the fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher (1990) *Meth. Enzymology,* 182: *Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the anti-MUC4 antibody-effector fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan 91993) *Bioconjug. Chem.*, 4: 581-585; and Buchner et al. (1992) *Anal. Biochem.*, 205: 263-270, and the like).

One of skill would recognize that modifications can be made to the anti-MUC4 antibody-effector fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

III. Pharmaceutical Compositions

In another aspect, pharmaceutical compositions are provided containing one or a combination of anti-MUC4 antibodies as described herein, and/or antigen binding portion(s) thereof, and/or chimeric moieties comprising an anti-MUC4 antibody attached to one or more effectors, formulated together with a pharmaceutically acceptable carrier (e.g., excipient).

In certain embodiments, the anti-MUC4 antibodies as described herein, and/or antigen binding portion(s) thereof, and/or chimeric moieties comprising an anti-MUC4 antibody attached to one or more effectors are administered to a mammal in need thereof (e.g., an animal having or at risk for a cancer characterized by upregulation of MUC4). In various embodiments the compositions can be administered to detect and/or locate, and/or quantify the presence of MUC4 expressing/overexpressing cells (e.g., tumors). In various embodiments the compositions can be administered to inhibit growth and/or proliferation of a neoplastic cell that overexpresses MUC4

Accordingly, in certain embodiments, a composition, e.g., a pharmaceutical composition, containing one or a combination of anti-MUC4 antibodies, or antigen binding portion(s) thereof, and/or chimeric moieties comprising the anti-MUC4 antibodies described herein together with a pharmaceutically acceptable carrier/excipient. In one embodiment, the compositions include a combination of multiple (e.g., two or more) isolated antibodies or chimeric constructs described herein.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, chimeric moiety, bi-specific and multispecific molecule, may be coated in a material to protect the compound from the action of acids and other natural conditions that may inactivate the compound.

In certain embodiments the antibody and/or chimeric construct is provided in its native form, or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions*, Mechanisms and Structure, 4th Ed. N.Y. Wiley-Interscience.

A "pharmaceutically acceptable salt" refers to a salt that retains the desired biological activity of the parent compound and does not impart any undesired toxicological effects (see e.g., Berge et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Methods of formulating such derivatives are known to those of skill in the art. For example, the disulfide salts of a number of delivery agents are described in PCT Publication WO 2000/059863 and are well known to those of skill in the art. For example, acid salts of therapeutic peptides (antibodies and the like) can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

Pharmaceutical compositions of the invention can be administered alone or in combination therapy, i.e., combined with other agents. For example, the combination therapy can include a composition described herein with at least one or more additional therapeutic agents, such as the anti-cancer agents described in Table 3. The pharmaceutical compositions of the invention can also be administered in conjunction with radiation therapy and/or surgery.

An anti-MUC4 peptide or chimeric construct or formulation thereof can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., *Sustained and Controlled Release Drug Delivery Systems*, J. R. Robinson, ed., Marcel Dekker, Inc., New York, 1978).

To administer a composition described herein (e.g., an anti-MUC4 antibody or chimeric construct comprising an anti-MUC4 antibody) by certain routes of administration, it may be necessary to coat the compound with, or co-administer the compound with, a material to prevent its inactivation. For example, in certain embodiments the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *Neuroimmunol.* 7: 27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions are typically sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, certain preferred methods of preparation include vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the anti-MUC4 antibodies or chimeric constructs comprising the anti-MUC4 antibodies may be administered once or twice weekly by subcutaneous injection or once or twice monthly by subcutaneous injection.

Non-limiting examples of suitable dosage ranges and regiments include 2-50 mg/kg (body weight of the subject) administered once a week, or twice a week or once every three days, or once every two weeks, and 1-100 mg/kg administered once a week, or twice a week or once every three days, or once every two weeks. In various embodiments, an antibody or chimeric construct is administered at a dosage of 3.2 mg/kg, 6 mg/kg, 10 mg/kg, 15 mg/kg, 20 mg/kg, 25 mg/kg, 30 mg/kg, 35 mg/kg or 40 mg/kg at a timing of once a week, or twice a week or once every three days, or once every two weeks. Additional dosage ranges include: 1-1000 mg/kg, 1-500 mg/kg, 1-400 mg/kg, 1-300 mg/kg and 1-200 mg/kg. Suitable dosage schedules include once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

Use of an anti-MUC4 antibody described herein and/or a chimeric construct comparing an anti-MUC4 antibody described herein alone, or in combination with an additional therapeutic agent can lead to an additive effect for anti-tumor activity. Accordingly, for combination therapy, suboptimal dosages of the antibody or the second therapeutic agent, or both, can be used to achieve a desired therapeutic outcome due to the additive effects of the agents. For example, when used in combination with another therapeutic agent, in various embodiments an antibody or chimeric construct described herein may be administered at a dosage that is 90%, or 80%, or 70% or 60% or 50% of the dosage used when the antibody or chimeric construct is administered alone.

In certain embodiments it is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient that can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations that are suitable for vaginal administration also include pessaries, tampons, creams, gels, pastes, foams or spray formulations containing such carriers as are known in the art to be appropriate. Dosage forms for the topical or transdermal administration of compositions described herein include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Particular examples of adjuvants that are well-known in the art include, for example, inorganic adjuvants (such as aluminum salts, e.g., aluminum phosphate and aluminumhydroxide), organic adjuvants (e.g., squalene), oil-based adjuvants, virosomes (e.g., virosomes that contain a membrane-bound heagglutinin and neuraminidase derived from the influenza virus).

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When the anti-MUC4 antibodies and/or chimeric constructs comprising the anti-MUC4 antibodies described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds described herein, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for an antibody or a chimeric composition described herein to be administered alone, it is preferable to administer the compound as a pharmaceutical formulation (composition).

Therapeutic compositions can be administered with medical devices known in the art. For example, in certain embodiments, an anti-MUC4 antibody and/or a chimeric construct comprising an anti-MUC4 antibody described herein be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., Ranade (1989) *J. Clin. Pharmacol.* 29: 685). Exemplary targeting moieties include, but are not limited to folate or biotin (see, e.g., U.S. Pat. No. 5,416,016); mannosides (see, e.g., Umezawa et al., (1988) *Biochem. Biophys. Res. Commun.* 153:1038); antibodies (see, e.g., Bloeman et al. (1995) *FEBS Lett.* 357:140; M. Owais et al. (1995) *Antimicrob. Agents Chemother.* 39:180); surfactant protein A receptor (see, e.g., Briscoe et al. (1995) *Am. J. Physiol.* 1233:1234), different species of which may comprise the formulations of the inventions, as well as components of the invented molecules.

IV. Combined Formulations.

In certain embodiments combined formulations comprising an anti-MUC4 antibody described herein, and/or an anti-MUC4 chiimeric moiety as described herein and an anti-cancer formulation are contemplated.

Useful classes of drugs that can be used combined formulations include, but are not limited to cytotoxic or immuno-modulatory agents such as, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

In certain embodiments the cytotoxic or immunomodulatory agents include, for example, a retinoic acid or a retinoic acid derivative, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluorodeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbazine, rapamycin (Sirolimus), streptozotocin, tenoposide, 6-thioguanine, thioTEPA, topotecan, vinblastine, vincristine, vinorelbine, VP-16 and VM-26. In certain embodiments the drugs include, but are not limited to, abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antisense molecule, an SiRNA, and the like. In certain embodiments the drugs include one or more drugs shown in Table 3.

In certain embodiments the drugs include one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

These combined formulations are illustrative and non-limiting. Using the teachings provided herein, other combined formulations will be available to one of skill in the art.

V. Uses of Anti-MUC4 Antibodies.

A) Therapeutic/prophylactic uses.

In various embodiments the anti-MUC4 antibodies described herein (e.g., antibodies that bind MUC4α N-ter and/or MUC4α C-ter) are used in various therapeutic and/or prophylactic applications. In particular the antibodies are administered to a mammal in need thereof (e.g., a human or a non-human mammal) to inhibit the growth and/or proliferation of cells expressing or overexpressing MUC4. In certain embodiments the anti-MUC4 antibodies described herein are used in the treatment or prophylaxis of a neoplasias. In certain embodiments they are used in the treatment of a cancer such as pancreatic cancer, gastric cancer, cervical cancer, and ovarian cancer.

The antibodies can be used to inhibit the growth or proliferation of neoplastic cells in a primary tumor, in a secondary tumor, of a metastatic cell in the blood or lymph, or to inhibit the formation of metastatic cells. In certain embodiments the antibodies inhibit the onset, slow the progression, or reduce the ultimate severity of the disease.

In certain embodiments the use of a chimeric moiety comprising an anti-MUC4 antibody described herein (e.g., an antibody that binds to MUC4α N-ter and/or to MUC4α C-ter) attached to an effector is used to inhibit the growth or proliferation of neoplastic cells in a primary tumor, in a secondary tumor, of a metastatic cell in the blood or lymph, or to inhibit the formation of metastatic cells. In certain embodiments the antibodies inhibit the onset, slow the progression, or reduce the ultimate severity of the disease. In various embodiments the effector attached to the antibody comprises a moiety selected from the group consisting of a cytokine that stimulates and immune response, a second antibody that recruits an immune response, a cytotoxin, a radionuclide, a radiosensitizer, an anticancer drug, a carrier (e.g., lipid, liposome, polymeric particle) comprising an anti-cancer drug, and a chelate comprising a radionuclide and/or an anticancer drug, e.g. as described herein.

In various embodiments the antibody and/or chimeric construct (chimeric moiety) is provided as a pharmaceutical formulation, e.g., as described herein.

In certain embodiments the antibody and/or chimeric construct is administered in conjunction with an anti-cancer agent as described herein. The terms "coadministration" or "administration in conjunction with" when used in reference to the use of an anti-MUC4 antibody or a chimeric construct comprising an anti-MUC4 antibody in conjunction with an ant-cancer agent indicates that the anti-MUC4 antibody or a chimeric construct comprising an anti-MUC4 antibody and the anti-cancer agent administered so that there is at least some chronological overlap in the activity of the anti-MUC4 antibody or a chimeric construct comprising an anti-MUC4 antibody and the anti-cancer agent. The administration of the anti-MUC4 antibody or a chimeric construct comprising an anti-MUC4 antibody and the anti-cancer agent can be simultaneous (e.g., in a combined formulation) or sequential. In sequential administration there may even be some substantial delay (e.g., minutes or even hours) between administration of the anti-MUC4 antibody or a chimeric construct comprising an anti-MUC4 antibody and the anti-cancer agent.

In various embodiments, classes of anti-cancer agents that can be used in conjunction with the anti-MUC4 antibody or chimeric constructs comprising an anti-MUC4 antibody include, but are not limited to cytotoxic or immunomodulatory agents such as, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

In certain embodiments the cytotoxic or immunomodulatory agents include, for example, a retinoic acid or a retinoic acid derivative, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluorodeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbazine, rapamycin (Sirolimus), streptozotocin, tenoposide, 6-thioguanine, thioTEPA, topotecan, vinblastine, vincristine, vinorelbine, VP-16 and VM-26. In certain embodiments the drugs include, but are not limited to, abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antisense molecule, an SiRNA, and the like. In certain embodiments the drugs include one or more drugs shown in Table 3.

In certain embodiments the anti-cancer agents include one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

In certain embodiments treatment methods are contemplated that incorporate diagnostic methods utilizing one or more of the antibodies and/or chimeric constructs described herein. Thus, in one illustrative embodiments, the method can involve receiving the results of an in vivo or ex vivo diagnostic assay (e.g., as described herein) for cells, especially neoplastic cells showing MUC4 (e.g., upregulated MUC4) and when the assay is positive administering or causing to be administered an anti-MUC4 antibody or chimeric construct comprising an anti-MUC4 antibody as described herein, and/or performing a surgery and/or radiotherapy to treat the neoplasias, and/or administering or causing to be administered an anti-cancer agent as described herein.

B) Diagnostic Uses.

In various embodiments the anti-MUC4 antibodies described herein and/or chimeric constructs comprising the anti-MUC4 antibodies described herein are used in in vivo or ex vivo diagnostic methods.

1) In Vivo Diagnostic Methods.

In certain embodiments, the antibodies described herein are utilized in a "pretargeting" strategy (resulting in formation of a chimeric moiety at the target site after administration of the effector moiety) or in a "targeting" strategy where the antibody is coupled to an effector molecule prior to use to provide a chimeric molecule.

For in vivo diagnostic applications the effector typically comprises a detectable label or a radiopaque moiety or an epitope tag where the second construct that binds the epitope tag comprises a detectable label or a radiopaque moiety. Suitable detectable labels include, but are not limited to radioopaque labels, nanoparticles, PET labels, MRI labels, radioactive labels, and the like. Among the radionuclides and useful in various embodiments of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing cancer cells expressing MUC4. Such detection/visualization can be useful in various contexts including, but not limited to pre-operative and intraoperative settings. Thus, in certain embodiment this invention relates to a method of intraoperatively detecting and cancers (e.g., pancreatic cancer, gastric cancer, cervical cancer, and ovarian cancer) in the body of a mammal. These methods typically involve administering to the mammal a composition, in a quantity sufficient for detection by a detector (e.g. a gamma detecting probe), an anti-MUC4 antibody labeled with a detectable label (e.g. antibodies of this invention labeled with a radioisotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

In certain embodiments the label-bound antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place. In certain embodiments such methods are particularly useful in localizing and removing secondary cancers produced by metastatic cells from a primary tumor.

2) Ex Vivo Diagnostic Methods.

In certain embodiments the anti-MUC4 antibodies described herein and/or chimeric constructs comprising the anti-MUC4 antibodies described herein are used in ex vivo diagnostic methods.

The antibodies described herein can readily be used to detect cells expressing or overexpressing MUC4. The methods can be carried out in accordance with a number of known immunoassay methods, for example to measure the presence of a neoplastic cell (e.g., pancreatic cancer, gastric cancer, cervical cancer, ovarian cancer, etc.). In certain embodiments the assays determines the presence of a malignant state in said cells. The term "malignant state" means the presence of atypical tumor cells and the like a cancer. The presence of a neoplastic cell in a sample is confirmed by allowing the sample to react with the anti-MUC4 antibody described herein and then detecting the formation of an immune complex (e.g., an immune complex linked to cell(s) in the sample).

In one illustrative embodiment, neoplastic cells expressing MUC4 are detected in a biological sample (e.g., in a blood sample, sputum/oral fluid, amniotic fluid, a blood fraction, a biopsy sample (e.g., surgical biopsy, fine needle biopsy, etc.) urine, peritoneal fluid, pleural fluid, and the like) where the presence such cells is an indicator of the presence of a cancer (e.g., pancreatic cancer, gastric cancer, cervical cancer, ovarian cancer, etc.) or a cell from such a cancer (e.g., a metastatic cell).

In one illustrative, but non-limiting embodiment, a tumor section obtained by excision is fixed on a slide glass in the usual way. The tumor section is allowed to react with an anti-MUC4 antibody described herein. With regard to the reaction conditions, the reaction is carried out for example in an appropriate container such as a Petri dish. After removing non-specifically bound antibodies by washing, subsequent reaction is carried out with a second antibody that can react with said antibody and is labeled with a detectable marker. The marker is a substance which can generate a detectable signal, such as a radioactive element, a fluorescent material, an enzyme or the like.

Since binding of the antibody is an indicator of the presence and/or amount of MUC4 the presence of a neoplastic cell can be confirmed by detecting the detectable signal. In addition, binding of the antibody to a sample can also be measured by using the monoclonal antibody to which a radioactive material, an enzyme or the like marker capable of generating a detectable signal is linked, e.g., by covalent bonding. This method is not limited to excised tissues, and it can be used in the detection of cancer cells in a variety of biological samples (including for example, blood and blood fractions, and the like).

In certain illustrative and non-limiting embodiments the ex vivo detection methods involve contacting a sample derived from said mammal with an anti-MUC4 antibody described herein (e.g., an antibody that binds to MUC4α N-ter and/or MUC4α C-ter), and determining the presence or amount of the antibody associated with a cell or a cellular component in the sample, where the presence and/or amount of the antibody associated with a cell or a cellular component in said sample indicates the presence of a neoplastic cell that expresses or overexpresses MUC4 in said mammal. In certain embodiments the cell is a metastatic cell, and/or a solid tumor cell, and/or a cancer stem cell. In certain embodiments the cell is a cancer cell selected from the group consisting of pancreatic cancer, lung cancer, breast cancer, gall bladder cancer, salivary gland cancer, prostate cancer, biliary tract cancer, cervical cancer, and ovarian cancer. In certain embodiments the cell is a cancer cell selected from the group consisting of extra hepatic bile duct carcinoma, colangiocarcinoma, cutaneous squamous cell carcinoma, and pancreatic cancer.

Any of a number of biological samples are suitable for use in the assay. Such samples include, but need not be limited to whole blood, a blood fraction, saliva/oral fluid, urine, a tissue biopsy, pleural fluid, pericardial fluid, cerebral spinal fluid, and peritoneal fluid. In certain embodiments the biological sample comprises peripheral blood mononuclear cells.

In various embodiments the method involves detecting the formation of immune complexes by the anti-MUC4 antibody and a MUC4 by a method selected from the group consisting of labeled primary antibody detection, labeled secondary antibody detection, flow cytometric analysis, immunochemical detection, radioimmunoassy, fluorescent immunoassay, enzyme-linked immunoassay, immunohistochemistry, and immunoblot analysis. The assay can be a solution-based assay (e.g., the anti-MUC4 antibody is in solution) or a solid-phase assay (e.g., the anti-MUC4 antibody is immobilized on a solid support). The method need not be dispositive for the presence of a cancer to be useful. In certain embodiments the method comprises a component in a differential diagnosis for cancer.

The antibodies specific for MUC4α N-ter and/or MUC4α C-ter can be used in essentially any assay designed to detect and/or to quantitate target protein (e.g., MUC4). Such assays include, but are not limited to: flow cytometric analysis; (2) immunochemical detection and/or localization of MUC4 protein in tumor cells or cells in various stages of differentiation; immunoblot analysis (e.g., dot blot, Western blot) of extracts from various cells, cell sorting assays, immunohistochemistry, and the like.

Kits.

In certain embodiments, kits are provided for the treatment of neoplasias characterized by the expression of MUC4 or for the for the detection of certain cells (e.g. cells expressing MUC4). The kits typically comprise an anti-MUC4 antibody described herein and/or a chimeric moiety comprising an anti-MUC4 antibody described herein attached to an effector. In certain embodiments the effector has immunnomodulatory, cytostatic, or cytotoxic activity. In certain embodiments the effector is selected from the group consisting of a cytokine that induces an immune response directed to said cell, a second antibody that induces an immune response directed to said cell, a radionuclide that cytostatic or cytotoxic to said cell, a radiosensitizer, a prodrug, a chelate comprising a drug or radionuclide that is cytotoxic or cytostatic to said cell, an anti-cancer drug, and a lipid, liposome, or polymeric particle comprising an anti-cancer drug.

In certain embodiments the chimeric moiety comprises an comprising an anti-MUC4 antibody described herein attached to an epitope tag, in which case the kit optionally additional comprises a second construct comprising a binding partner that binds the epitope tag attaché to an effector (e.g., as described above).

In certain embodiments the kits are provided for the detection of cells (e.g., neoplastic cells) that express or overexpress MUC4. In certain embodiments these kits comprises an anti-MUC4 antibody described herein and, optionally, a detectable label for detecting the antibody. In certain embodiments the kit further comprises reagents suitable for detecting MUC4-antibody immunocomplexes, if present in a biological sample. In certain embodiments the detectable label is attached to an antibody that binds to immunocomplexes formed between said anti-MUC4 antibody and MUC4. In certain embodiments the detectable label is attached to the anti-MUC4 antibody. In certain embodiments the anti-MUC4 antibody is in solution. In certain embodiments the anti-MUC4 antibody is immobilized on a solid support (e.g., filter paper, multiwell dishes, microchips, and polymeric particles, test strips, derivatized magnetic particles, and the like). In certain embodiments the detectable label is a radioactive label or a fluorescent label. In certain embodiments the detectable label is selected from the group consisting of fluorescein, rhodamine, phycoerythrin, biotin, and strepavidin.

In addition the kits typically include instructional materials disclosing means of use of the antibody or chimeric moiety (e.g. as a therapeutic for a pancreatic cancer, gastric cancer, cervical cancer, and ovarian cancer, for detection of neoplastic cells, to augment an immune response, etc.). The kits may also include additional components to facilitate the particular application for which the kit is designed. Thus, for example, where a kit contains a chimeric molecule in which the effector molecule is a detectable label, the kit can additionally contain means of detecting the label (e.g. enzyme substrates for enzymatic labels, filter sets to detect fluorescent labels, appropriate secondary labels such as a sheep anti-mouse-HRP, or the like). The kits can additionally include buffers and other reagents routinely used for the practice of a particular method. Such kits and appropriate contents are well known to those of skill in the art.

In addition, the kits optionally include labeling and/or instructional materials providing directions (e.g., protocols) for the use of the antibodies and/or chimeric constructs described herein in the treatment of neoplasias, and/or in the detection of neoplastic cells expressing a MUC4.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Monoclonal Antibodies Recognizing the Non-Tandem Repeat Regions of the Human Mucin MUC4 in Pancreatic Cancer In this example, we report the generation and characterization of a novel anti-MUC4 MAbs that recognize the regions of MUC4α both upstream and downstream of the TR domain. Purified recombinant MUC4 fragments, fused in frame with GST, were used as immunogens and positive clones were selected based on their reactivity in ELISA. Selected clones were characterized by their reactivity toward MUC4 in immunoblotting, immunoprecipitation, immunofluorescence and flow cytometry using pancreatic cancer cells. The non-TR anti-MUC4 MAbs developed in this study are believed to be useful reagents for the development of assays for quantification of MUC4 in tissues and biological fluids, to study the functional role of MUC4 in various diseases and potentially for immunotherapy.

Results

Figure 2B:
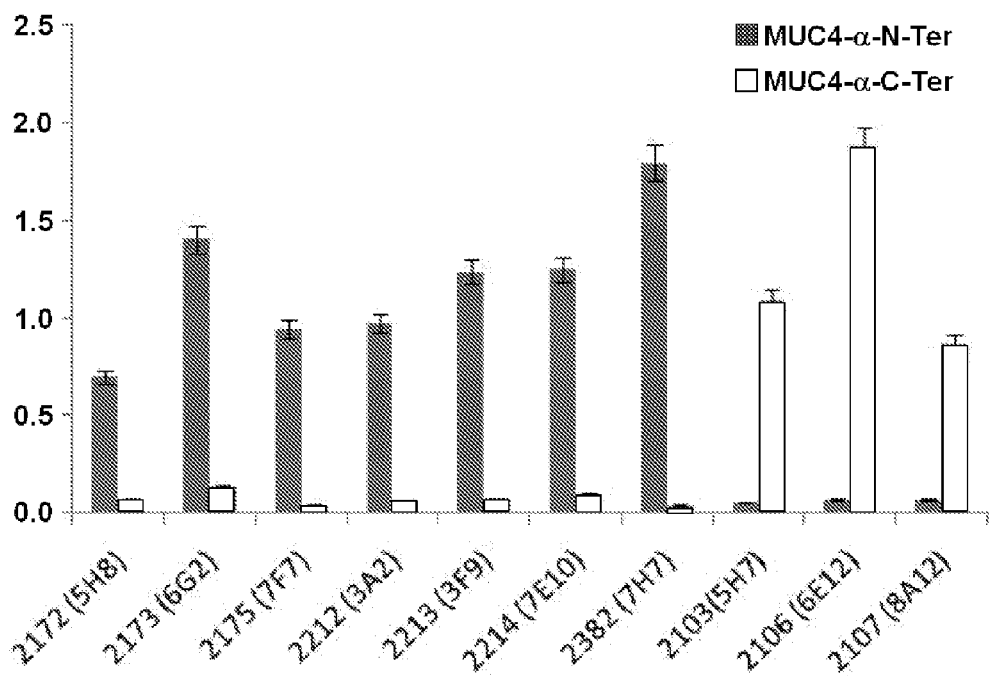

The schematic structure of MUC4 and the recombinant domains are indicated in FIG. 2A. Following cell fusion, culture supernatants from stable hybridomas were screened and the positive hybridomas exhibiting high reactivity with the recombinant protein and negative reactivity with GST were cloned by three rounds of limiting dilution. Seven stable clones reactive with MUC4α-N-Ter and three clones reactive with MUC4α-C-Ter were obtained (Table 4 and FIG. 2B). MAbs 2172, 2173, 2175, 2212, 2213, 2214 and 2382 exhibited specific reactivity toward MUC4α-N-Ter, while MAbs 2103, 2106 and 2107 were specific to MUC4α-C-Ter. Further, none of the selected antibodies showed any reactivity toward purified MUC4 TR peptide, BSA or GST (data not shown). Similarly, previously generated anti-MUC4 TR antibody 8G7 or anti-KLH antibody K2G6 showed no reactivity toward the recombinant MUC4 domains.

TABLE 4

Nomenclature, isotype, and origin of non-TR anti-MUC4 MAbs. The generation of control MAbs 8G7, and K2G6 has been described in Venkatraman et al. (2011) *PLoS ONE* 6(8): e23344. doi: 10.1371/journal.pone.0023344.

| Clone ID | Immunogen | Isotype |
| --- | --- | --- |
| 2172 (5H8) | MUC4α-N-Ter | IgG2b, κ |
| 2173 (6G2) | MUC4α-N-Ter | IgG1, κ |
| 2175 (7F7) | MUC4α-N-Ter | IgG1, κ |
| 2212 (3A2) | MUC4α-N-Ter | IgG1, κ |
| 2213 (3F9) | MUC4α-N-Ter | IgG1, κ |
| 2214 (7E10) | MUC4α-N-Ter | IgG1, κ |
| 2382 (7H7) | MUC4α-N-Ter | IgG1, κ |
| 2103 (5H7) | MUC4α-C-Ter | IgM, κ |
| 2106 (6E12) | MUC4α-C-Ter | IgG1, κ |
| 2107 (8A12) | MUC4α-C-Ter | IgG1, κ |
| 8G7 | MUC4-TR peptide | IgG1, κ |
| K2G6 | KLH | IgG1, κ |

Figure 3:
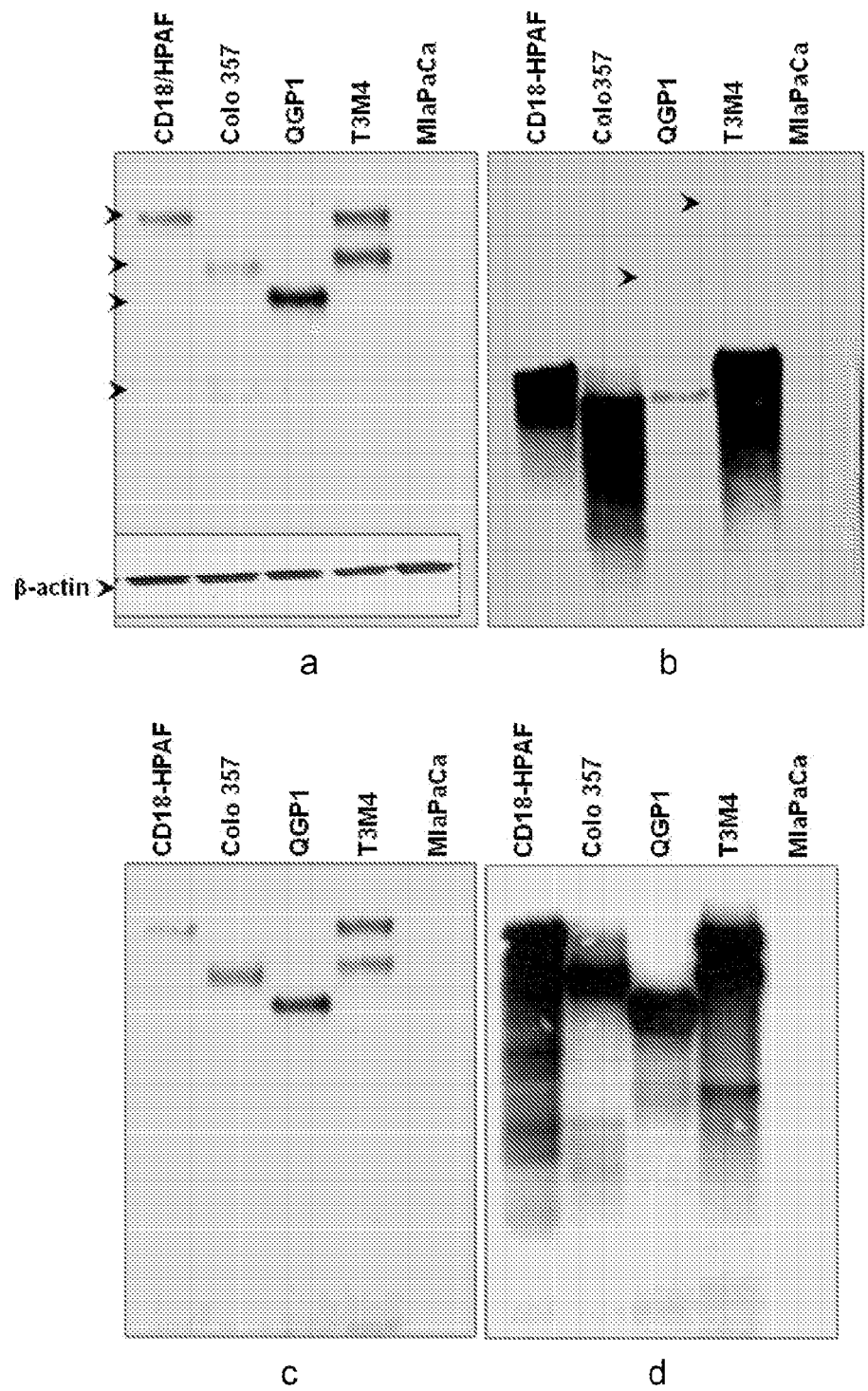
FIG. 3, panels a-d, shows comparative immunoblot analysis for MUC4 expression in various pancreatic cancer cell lines using various antibodies. A total of 20 µg of protein from cell extracts was resolved by electrophoresis on a 2% SDS-agarose gel, transferred to PVDF membrane, and incubated with 2 mg/ml of MAbs 2175 (panel a), 2214 (panel b), 2382 (panel c) or 1 µg/ml of anti-MUC4 TR Mab 8G7 (panel d). The membrane was then probed with horseradish peroxidase-labeled goat anti-mouse immunoglobulin. The signal was detected using an ECL reagent kit. The position of the detected bands is indicated by arrows. For loading control, immunoblot for the detection of β-actin (inset a) was done on lysates of respective cells resolved on 10% SDS-PAGE.

The antibodies were further tested for their ability to specifically recognize the MUC4 protein in the lysates of MUC4 expressing pancreatic cancer cell lines by immunoblotting. Of the seven MUC4α-N-Ter-specific antibodies only MAbs 2214, 2175 and 2382 recognized the MUC4 protein in the cell lysates (FIG. 3). MAbs 2215 and 2382 recognized high molecular weight protein bands in the lysates of the MUC4 positive cells (HPAF/CD18, Colo357, QGP1 and T3M4) (FIG. 3, panels a and c) and the reactivity pattern was similar to that of anti-TR MAb 8G7 (FIG. 3, panel d). Each of the MUC4 positive cell lines exhibited a characteristically distinct band size which is consistent with our previous reports of VNTR polymorphisms in MUC4 with HPAF/CD18, Colo357 and QGP1 showing a single band and T3M4 expressing two bands (allelic VNTR polymorphism). Unlike MAbs 2175, 2382 and 8G7, MAb 2214 reacted predominantly with the low molecular weight form of MUC4 but with the band pattern corresponding to the VNTR polymorphism (FIG. 3, panel b). Mab 2214 also showed very weak reactivity with the high molecular band corresponding to those recognized by other antibodies in QGP1 and T3M4 lysates. Immunoblot analysis of b-actin in the SDS-PAGE resolved lysates indicated equal protein loading (FIG. 3, inset). No reactivity was observed with any antibody with the lysate of the MUC4 negative cell line MiaPaCa. None of the anti-MUC4α-C-Ter antibodies reacted with MUC4 in the cell lysates in immunoblotting (data not shown).

Figure 4:
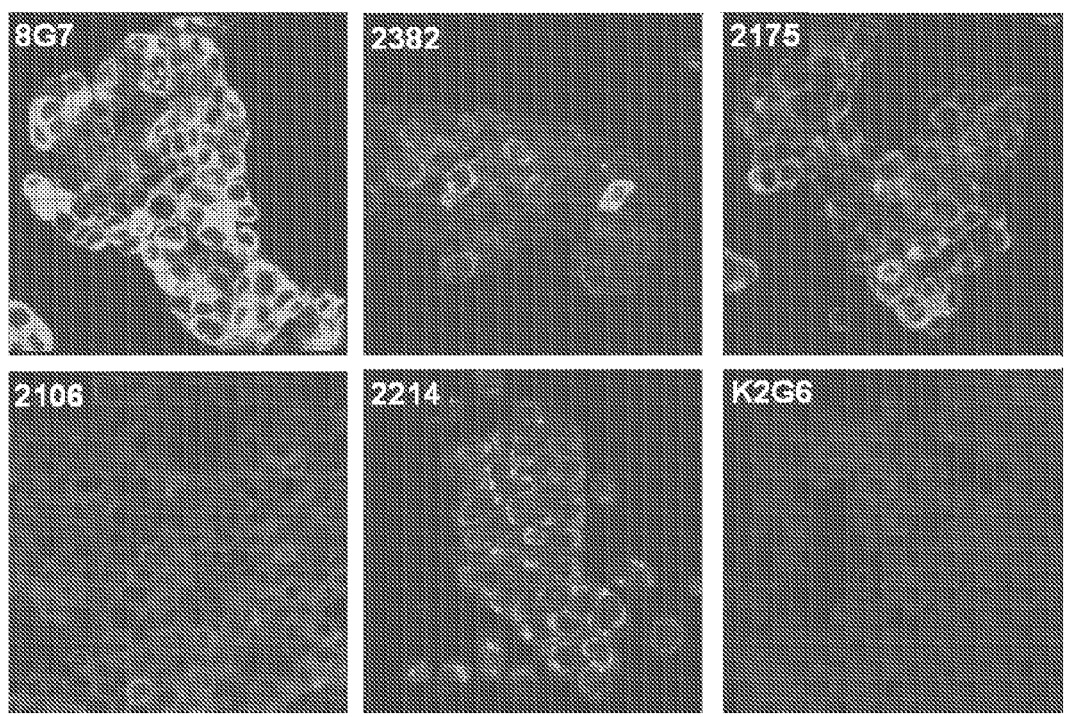
FIG. 4 shows immunofluorescence of MUC4 in CD18/HPAF cells with various anti-MUC4 MAbs. Cells were grown at low density on sterilized cover-slides, fixed in ice-cold methanol at −20° C. and were incubated with 10 µg/ml non-TR MAbs of 2214, 2175, 2382 and 2106, or 2 µg/ml of anti-MUC4 TR MAb 8G7 (Control) and detected using FITC conjugated secondary antibody. Anti-KLH antibody $K_2G6$ was used as an isotype control. Cells were mounted on glass slides using anti-fade Vectashield mounting medium and observed under a ZEISS confocal laser scanning microscope (magnification, 6630).
Figure 5:
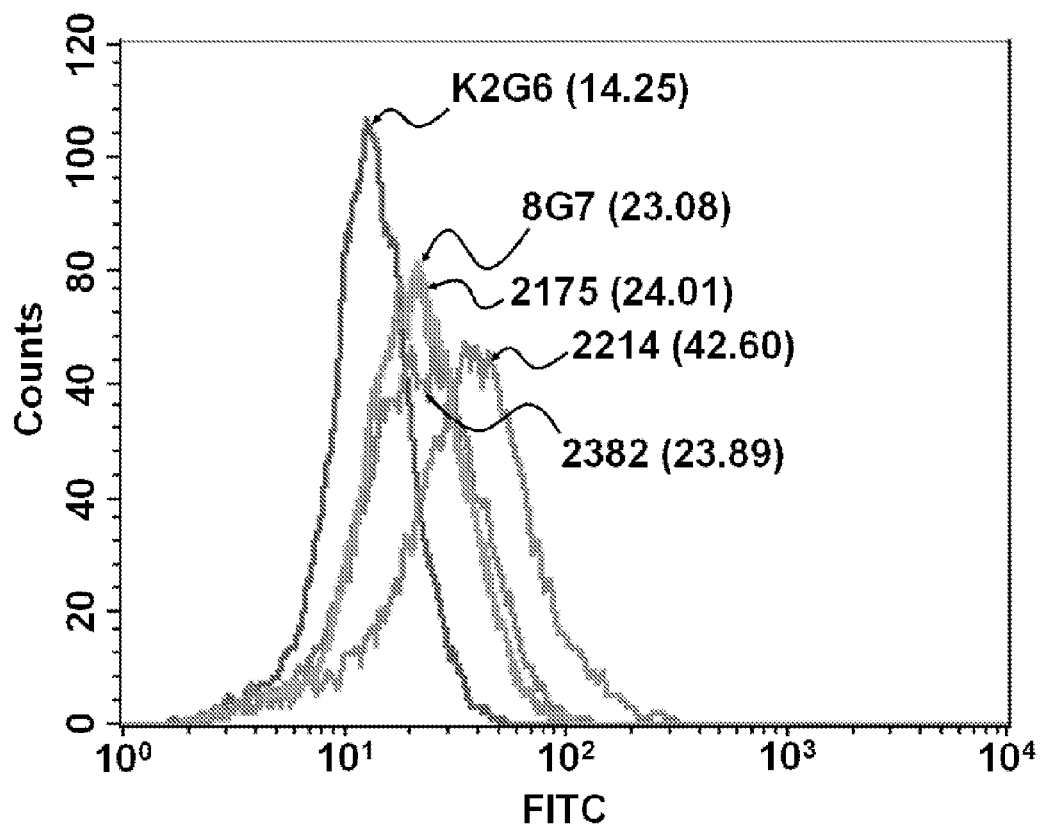
FIG. 5 shows cell-surface binding analysis of anti-MUC4 antibodies. Cells were harvested non-enzymatically, fixed with paraformaldehyde and incubated with the indicated antibodies. Following incubation with secondary antibody, cells were analyzed using BD FACSCalibur. The mean fluorescence intensities (MFI) values obtained with each antibody is indicated in parentheses.

The ability of antibodies to recognize MUC4 in the intact cells was studied by immunofluorescence and flow cytometry. In the methanol fixed and permeabilized assay HPAF/CD18 cells all the selected MAbs exhibited specific staining for MUC4; no staining was observed with the control anti-KLH antibody K2G6 (FIG. 4). MAb 2214 showed a both membrane and perinuclear staining, while MAbs 2175, 2382 and 2106 showed cytoplasmic and membrane staining. The anti-TR MAb 8G7 showed strongest reactivity due to the repetitive nature of the epitopes. Further, none of the antibodies showed any reactivity with MUC4 negative pancreatic cancer cell lines MiaPaCa or Panc1 (data not shown). For cell surface staining, parformaldehyde-fixed (unpermmeabilized) cells were used and the binding of the antibodies was analyzed by flow cytometry. MAb 2214 exhibited the strongest reactivity with the cell surface in paraformaldehyde-fixed cells, while the surface reactivity of MAbs 2175 and 2382 was weak and the mean fluorescence intensity (MFI) values were comparable to the values obtained with MAb 8G7 (FIG. 5).

Figure 6:
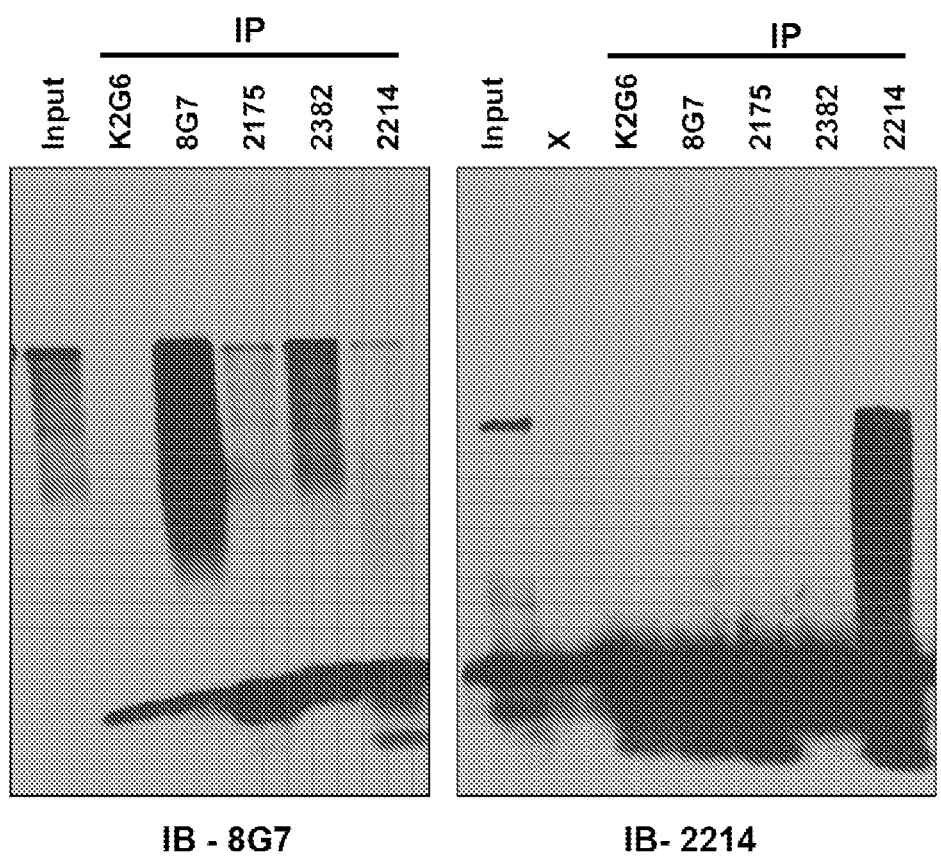
FIG. 6 shows the results of immunoprecipitation of MUC4 using various MAbs to MUC4. Protein lysates from the MUC4-expressing CD18/HPAF cells were immunoprecipitated using 5 mg/ml of 8G7 (Tandem repeat MAb), 2382, 2214 and 2175 (Non-tandem repeat MAbs) and K2G6 (Isotype matched control MAb) and were immunoblotted using MAbs 8G7 and 2214 as described in Materials and Methods in Example 1.

The domain-specific anti-MUC4 antibodies were also tested for their ability to immunoprecipitate MUC4 using the HPAF/CD18 lysate. MAbs 2382 2175, and 2214 immunoprecipitated full-length MUC4 from the total cell lysates, which was visualized when the processed samples were resolved on SAS-agarose gel and immunoblotted with anti-MUC4-TR MAb 8G7 (FIG. 6). The immunoprecipitated samples from various antibodies were also immunoblotted with MAb 2214 due to its predominant reactivity with a lower molecular weight form of MUC4. When probed with MAb 8G7, the highest amount of MUC4 was immunoprecipitated with 8G7, while MAb 2382 also resulted in considerable enrichment of the 8G7 reactive protein bands. MAbs 2175 and 2214 also immunoprecipitated the full-length 8G7 reactive band but the enrichment was not as strong as observed with MAbs 8G7 and 2382. Anti-C-terminal MAb 2106 and negative control anti-KLH antibody K2G6 did not pull down any 8G7 reactive protein band. However, none of the tested antibodies except 2214, immunopecipitated the MAb 2214-reactive low molecular weight form of MUC4.

Figure 7:
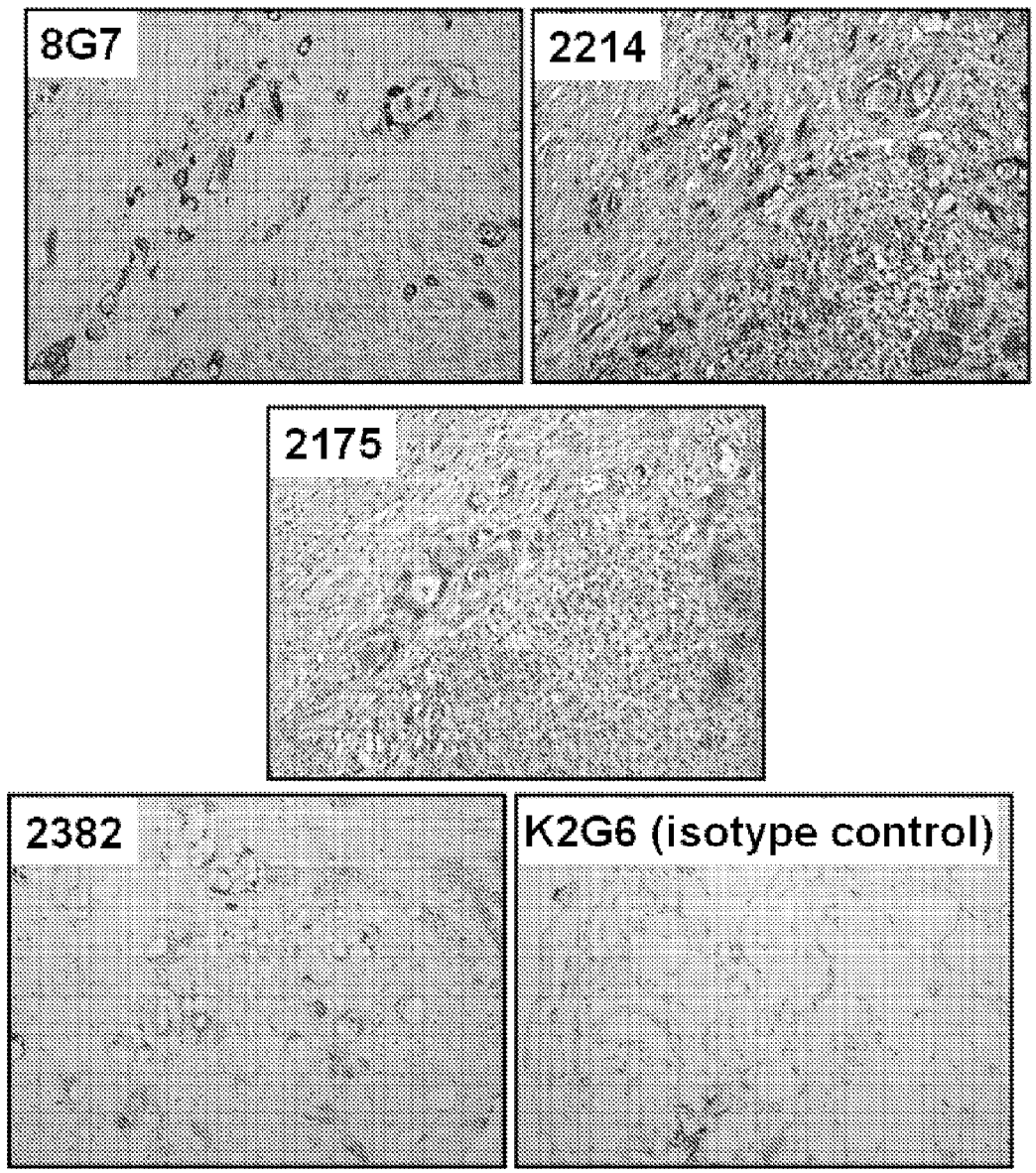
FIG. 7 shows immunoperoxidase staining for MUC4 in pancreatic cancer tissues using non-TR MAbs. Paraffin sections were incubated with the indicated test and control antibodies and binding was detected using VECTOR Universal staining Kit. MAb 8G7 was used at a concentration of 2 µg/ml, while all other antibodies were used at a concentration of 10 µg/ml.

The ability of antibodies to detect MUC4 in tumor tissues was tested by immunohistochemical analyses performed on pancreatic cancer tissues. MAbs 2214, 2175 and 2382 showed positive staining in the tumor tissue that was determined to be MUC4 positive based on its reactivity with anti-TR MAb 8G7 (FIG. 7). The pattern of staining with the new antibodies was similar to that observed with 8G7 showing diffuse staining in both the membrane and the cytoplasm of the tumor cells. No staining was observed with Mab 2106 or the non-specific isotype matched control MAb K2G6.

Discussion

MUC4 is a large glycoprotein involved in physiology and implicated in various disease states. Of particular importance is its role in pancreatic cancer development and progression (Chaturvedi et al. (2008) *FASEB J.,* 22: 966-981; Moniaux et al. (2004) *Br. J. Cancer,* 91: 1633-1638; Singh et al. (2007) *Cancer Res.,* 67: 433-436). A number of recent studies have established the role of the transmembrane mucin MUC4 in the pathogenesis of several malignancies. MUC4 consists of two domains, namely MUC4α which has the tandem repeat region and MUC4β which has the trans-membrane region and also possesses growth factor like domains (Moniaux et al. (1999) *Biochem. J.* 338: 325-333; Chaturvedi et al. (2008) *FASEB J.,* 22: 966-981). Due to the polymorphism in the number of tandem repeats (Nollet et al. (1998) *Biochem. J.,* 332: 739-748) and the existence of various splice forms completely devoid of the TR domain (Moniaux et al. (2000) *Eur. J. Biochem.,* 267: 4536-4544), the antibodies recognizing the nontandem repeat regions of the protein that could provide useful information about its function, possible interacting partners and more importantly can be used in quantitative assays.

Three of the antibodies raised against the region upstream of the central TR domain 2214, 2175 and 2382, and one of the antibodies generated against the downstream of the TR domain, 2106 showed strong reactivity against the respective recombinant domains in ELISA. None of the antibodies recognize the nonspecific recombinant domains, GST or synthetic TR peptides. These antibodies can serve as useful reagents for the development of MUC4 bioassays and can complement the existing anti-MUC4 TR antibody or other antibodies reactive against the carbohydrate epitopes present on mucins (DUPAN2, CA 19.9, TAG 72). Growing evidence suggests that the MUC4 mucin, due to its overexpression in several malignancies, is a potential marker for diagnosis (Singh et al. (2007) *Cancer Res.,* 67: 433-436), particularly for the lethal pancreatic cancer where its association with the early neoplastic lesions has been established (Saitou et al. (2005) *J. Clin. Pathol.,* 58: 845-852). Another recent study has shown MUC4 to be a novel prognostic factor of extrahepatic bile duct carcinoma (Tamada et al. (2006) *Clin. Cancer Res.,* 12: 4257-4264). MUC4 expression was correlated with poor prognosis in small sized lung adenocarcinoma (Tsutsumida et al. (2007) *Lung Cancer.* 55(2): 195-203). All of these studies have shown that MUC4 can be a key player in tumorigenesis; however, all of these studies have analyzed MUC4 in tissue samples, which could be limited by sampling errors, due to the heterogeneous expression of tumor antigens. Hence, it is be logical to develop quantitative assays for MUC4 in biological fluids, which are non-invasive, cost effective and easily automated. Due to the variable size of the tandem repeat region, the antibody recognizing the tandem repeat region could not be used for quantitative purposes. The domain specific antibodies can potentially aid in developing in vitro diagnostic assays to quantitate MUC4 in serum and other biological fluids.

All the antibodies reactive with the region upstream of the MUC4 TR domain were able to recognize MUC4 in the cell lysates of MUC4-expressing pancreatic cancer cells. MAbs 2175 and 2382 recognized the full-length MUC4 with a high molecular weight, with a band size similar to that recognized by anti-TR MAb 8G7. The difference in signal strength of the non-TR and TR antibodies could be attributed to the number of epitopes available for the MAb to bind, since 8G7 recognizes the tandem repeat region, which is represented multiple times in each molecule, whereas the epitopes recognized by 2175 and 2382 are represented only once per molecule. In contrast, Mab 2214 exhibited strong recognition of a protein band of smaller size than those recognized by MAbs 8G7, 2175 and 2382. Despite their lower molecular size, these bands mirrored the allelic variation exhibited by the full-length MUC4 for the respective cell lines, suggesting that Mab 2214 possibly reacts with an immature or underglycosylated form of MUC4. Very faint bands corresponding to the high molecular weight mature protein were still detected in QGP1 and T3M4. The stronger signal strength of Mab 2214 with the lower bands could be due to the abundance of an immature MUC4 protein in the cancer cells. In cancer cells it is well established that, due to aberrant and inefficient glycosylation, mucins are hypoglycosylated and these immature forms continuously undergo repeated cycles of internalization, resulting in a more immature form than the mature form. However, on-membrane deglycosylation (enzymatic or chemical) of resolved protein bands did not enhance the reactivity of Mab 2214 with the mature MUC4 bands (data not shown). However, in paraformadehyde fixed cells, MAb 2214 exhibited the highest reactivity with the cell surface. The immature protein is unlikely to be present on the cell surface, and possibly the fixation of cells with paraformaldehyde exposed the MAb 2214 reactive epitope. Further characterization of the low molecular weight form of MUC4 reactive with MAb 2214 is underway. Immunofluorescence analysis showed specific staining for MUC4 in membranes as well as in the cytoplasmic compartments of HPAF/CD18 cells. The staining pattern was comparable with the anti TR Mab 8G7 and their specificity to MUC4 was further supported by the lack of signal in MUC4 negative cells. The perinuclear staining of Mab 2214 further supports its reactivity to the immature protein.

Due to its large size and multi-domain organization, MUC4 can potentially interact with many proteins and these interactions could be the key to various functions attributed to MUC4. Its interaction with HER2 and the functional significance of this interaction has been well studied (Chaturvedi et al. (2008) *Cancer Res.*, 68: 2065-2070; Ponnusamy et al. (2008) *Br. J. Cancer*, 99: 520-526). However, there are many other potential interacting partners of MUC4 that could play an important role in modulating or mediating MUC4 function. MAbs 2175 and 2382 were able to immunoprecipitate the MUC4 protein from the cell lysates of HPAF/CD18 cells and could thus help in the isolation and identification of additional MUC4 interacting partners. Further, the predominant reactivity of MAb 2214 to lower molecular weight MUC4 is suggestive of a different form of MUC4 which co-exists with the mature protein. If, in fact, it is the immature form of the protein, then the MAb 2214 may potentially help in the isolation of various novel interacting partners that may interact with this form of MUC4 and unravel its functional significance.

MAbs 2214, 2175 and 2382 also recognized MUC4 expressed in the cancer tissues by immunohistochemical analysis with the reactivity pattern similar to that observed with anti-TR Mab 8G7. None of the normal pancreatic ducts were stained, which is in accordance with our earlier studies that have shown an absence of MUC4 expression in the non-neoplastic ducts. The new antibodies can be useful tools to corroborate the results obtained from 8G7, suggesting the overexpression of MUC4 in various malignancies. Further, due to the non-repetitive nature of their reactive epitope, the newly developed antibodies will provide a more reasonable measure of the extent of overexpression by negating the effects of VNTR polymorphism. The anti-TR antibody 8G7, however, would provide greater sensitivity of detection because of the multiplicity of the epitopes. Thus, the combination of anti-TR and anti-non TR MUC4 antibodies can provide better information about the extent of MUC4 overexpression in the tumor tissues. Efforts are underway to study the direct inhibitory effects of the antibodies on cancer cell growth, motility and invasion under both in vitro and in vivo conditions. Our recent studies have demonstrated that MUC4 contributes to the chemoresistance in pancreatic cancer cells by activating anti-apoptotic pathways and promoting cell survival (Bafna et al. (2009) *Br. J. Cancer*, 101: 1155-1161).

Hence it will be of interest to study the effect of anti-MUC4 antibodies in inducing apoptosis in cancer cells and augmenting their sensitivity to chemotherapeutic drugs. Further, these antibodies can be evaluated for their utility in radioimmunodiagnosis and radioimmunotherapy of MUC4 overexpressing tumors. Functional studies using the non-tandem repeat MAbs may probably provide a better understanding of MUC4 mediated mechanisms in cancer progression. These antibodies could also aid in understanding MUC4 structure-function relationships, regulation of expression and possibly identify a probable interacting partner on the tumor cell surface, which could be the reason for the metastatic phenotype. In conclusion, our studies indicate that MAbs 2175 and 2382 are highly specific in detecting the non-tandem repeat region of the mucin MUC4 by various immunoassays. These domain specific antibodies would serve as useful reagents to develop quantitative assays, and are valuable tools to study MUC4 structure-function relationships and possibly target MUC4 for therapy of solid tumors that overexpress MUC4.

Materials and Methods

Ethics Statement

The use of animals for immunization and isolation of spleen was approved by the Institutional Animal Care and Use Committee (IACUC) Protocol #94-025-12 titled "Monoclonal Antibody Core Facility Immunization Protocol".

Human pancreatic tumor tissues were obtained from the University of Nebraska Medical Center (UNMC) Tissue Bank and their use was approved via the UNMC Institutional Review Board (IRB) approval #491-97-EX.

Generation of Recombinant MUC4 Domains

Regions of MUC4-α on either side of the TR domain were cloned and expressed, and purified proteins were used as immunogens. Specific primers were designed using MUC4 sequence AJ000281 to amplify the fragments from nucleotides 587 to 3361 [MUC4α-Amino Terminal (MUC4α N-ter)] and from nucleotides 1 to 1293 [MUC4α-carboxy terminal (MUC4α C-ter), representing the regions immediately upstream and downstream of the TR domain, respectively (FIG. 2A). BamHI and an EcoRI restriction sites were added in the forward and reverse primers, respectively, allowing in-frame cloning with the GST and thrombin cleavage site of the pGEX-2TK vector (Pharmacia). Amplification was done by the expand long RT-PCR system (Roche) as described previously using JER103 and JER109 as templates for sequence AJ00281 and AJ010901, respectively (Moniaux et al. (1999) *Biochem. J.* 338: 325-333). The constructs were sequenced to confirm the proper reading frame and maintained in *E. coli* BL21 (New England Biolabs Inc.). A 5 ml overnight preculture of each recombinant strain was used to inoculate 1 liter of 26YTA medium (16 g tryptone, 10 g yeast extract, and 5 g NaCl in 900 ml of deionized water, 100 mg/ml ampicillin), and grown under agitation at 37 C for 3 to 4 h to reach an absorbance at 260 nm between 0.6-0.8, induced by 0.1 mM of IPTG, and cultured for an addition of 3 to 4 h. Cultures were centrifuged and washed three times in ice cold PBS, resuspended in 5 ml of ice cold PBS, and sonicated. Protein lysates were clarified by centrifugation and by filtration on a 0.22 mm filter. Lysates were passed through a 5 ml Glutathione Sepharose Fast Flow column (Pharmacia), washed three times with 5 column volumes of PBS, and eluted with 10 ml of 15 mM reduced gluthatione. Elution fractions of 1 ml were collected and 5 ml aliquot of each fraction was resolved on 10% SDS-PAGE, and proteins detected by coomassie blue staining Fractions containing pure GST-fusion proteins were pooled and quantified using the BIO-RAD D/C protein estimation kit (BIO-RAD).

Mouse Immunization

The immunization and selection of MAbs were carried out using established procedures at the UNMC Antibody Core Facility (Moniaux et al. (2004) *J. Histochem. Cytochem.*, 52: 253-261). Briefly, separate groups of mice (BALB/c) were immunized by repeated IP injections of recombinant GST fusion proteins MUC4α-N-Ter and MUC4α-C-Ter at two-week intervals. In each group, immunization with recombinant protein was alternated with the lysate of MUC4 positive HPAF/CD18 human pancreatic cancer cells (Id.). Sera from these mice were evaluated in direct binding assays for antibody reactivity with the recombinant MUC4 fusion protein, and GST was used as a negative control. Once an appropriate antibody response was observed in ELISA, the animals were given a final booster injection with the recombinant protein four days prior to exsanguination and splenectomy. Splenocytes were isolated and fused with NS-1 and/or Sp2/0 myeloma cells. Hybridomas producing the antibodies of interest were selected by screening for specific antibody binding to the immunogen of interest (recombinant proteins and HPAF/CD18 lysate) and lack of binding to irrelevant control antigens (GST and BSA). Screening for MUC4-positive Hybridomas Immulon plates were coated with 50 ml of the antigenic preparation (MUC4 recombinant proteins or GST or protein lysates from MUC4 positive cell lines) at a concentration of 2.5 mg/well in bicarbonate buffer (pH 9.6). The plates were incubated overnight at 4° C. The plates were washed in PBST and the free binding sites of the wells were saturated to eliminate nonspecific binding of the immunoglobulins by incubating with 200 ml/well of 2% non-fat skimmed milk in PBS for 2 h at 37° C. and plates were washed in PBST. One hundred ml of the culture supernatant was transferred from wells of culture plates into corresponding wells in ELISA plates. Mouse pre-immune serum was used as a negative control in each assay, incubated for 1 h at 37° C., and then the plates washed again in PBST. One hundred ml/well of the peroxidase conjugated antibody (anti-mouse HRP, Amersham Biosciences, 1:2000 dilution in PBS) was added and incubated for 1 h at 37° C. The plates were washed in PBST and 100 ml of TMB substrate (Dako Substrate) was added to each well and incubated at 37° C. The reaction was arrested by adding 100 ml of 2 M sulfuric acid and the plates were scanned at 450 nm in a Biotech ELISA plate reader.

Immunoprecipitation

Protein lysates from the MUC4-expressing HPAF/CD18 cells were immunoprecipitated using 5 mg/ml of 2382, 2214, 2175, 8G7 (anti-TR antibody), and K2G6 (isotype matched control MAb reacting with KLH). Antigen-Antibody complexes formed were pulled down by using Protein A/G beads (Calbiochem) and the complexes were solublized by using SDS-sample buffer containing 2-mercaptoethanol. The samples were resolved on 2% SDS-agarose gel and were immunoblotted using 8G7.

Immunoblotting

A series of pancreatic cell lines were processed for protein extraction and Western blotting using standard procedures (Id.). Briefly, the cells were washed twice in PBS and scraped in radioimmunoprecipitation assay (RIPA) buffer [50 mM Tris, 5 mM EDTA, 150 mM NaCl, 0.25% sodium deoxycholate; 1% NP40 (pH 7.5)], containing protease inhibitor mixture (Roche Diagnostics, Mannheim, Germany) and phosphatase inhibitors (5 mM NaF and 5 mM Na3VO4; Sigma Chemicals, St. Louis, Mo.), and kept at 4° C. for at least 30 min. Cell lysates were passed through the needle syringe or alternatively subjected to one freezethaw cycle to facilitate the disruption of the cell membranes. Cell lysates were centrifuged at 14,000 rpm for 30 min at 4° C., and supernatants were collected. Protein concentrations were determined using a BIO-RAD D/C protein estimation kit. Because of the large size of MUC4, the proteins (20 mg) were resolved by electrophoresis on a 2% SDS-agarose gel under reducing conditions. SDS-PAGE was used for β-actin, (protein loading control), and run under similar conditions. Resolved proteins were transferred onto the polyvinylidene difluoride membrane and subjected to the standard immunodetection procedure using specific antibodies. For MUC4 immunodetection, anti-MUC4 mouse monoclonal antibody 8G7 (1 mg/ml) positive control, and 2 mg/ml of non-tandem repeat antibodies diluted in PBS were used. Anti human β-actin (1:10000, Sigma AC-15) was used or the protein loading control. Horseradish peroxidase-conjugated goat anti-mouse (Amersham Biosciences) secondary antibody was used at a dilution of 1:2000. The blots were processed with ECL Chemiluminescence kit (Amersham Biosciences), and the signal was detected by exposing the processed blots to X-ray films (Biomax Films, Kodak, N.Y.).

Confocal Immunofluorescence Microscopy

For immunofluorescence staining, HPAF/CD18 cells were grown at low density on sterilized glass cover slides overnight. After washing with 0.1 M HEPES containing Hanks buffer, the cells were fixed in ice-cold methanol at −20° C. for 2 min. Nonspecific blocking was done in 10% goat serum containing 0.05% Tween 20 for at least 30 min, followed by incubation with the non-TR MAbs 2382, 2214, 2175 and anti-MUC4 TR MAb 8G7 was used as the positive control diluted in PBS. A non-specific isotype matched antibody, K2G6, was used as a negative control (1:100) for 1 h, at room temperature. Cells were washed 465 min with PBS containing 0.05% Tween 20 (PBS-T) and then incubated with FITC conjugated goat anti-mouse secondary antibodies for 30 min. Cells were washed twice with PBS-T, and mounted on glass slides in anti-fade Vectashield mounting medium (Vector Laboratories, Burlingame, Calif.). Immunostaining was observed under a ZEISS confocal laser-scanning microscope, and representative photographs were captured digitally using 510 LSM software.

Flow Cytometry

For flow cytometry, cells were harvested non-enzymatically using Cellstripper™ (Mediatech, Va.), washed with PBS (1% goat serum) and counted. Cells were fixed for 30 min with 2% paraformaldehyde (in PBS) and blocked with 5% goat serum. Cells were then incubated with indicated antibodies (1 μg/$10^6$ cells) for 1 h on ice. Subsequently, cells were washed three times with PBS and incubated with FITC conjugated anti-mouse antibody (0.75 μg/μl, 1:300 dilution) for 1 h on ice. Cells were washed again three times with PBS and analyzed using the BD FACSCALIBUR™ flow cytometer.

Immunohistochemical Analysis

Tissues were fixed in 10% buffered formalin and embedded in paraffin. Sections (5 μm) were cut and processed as described previously. Briefly, tissue sections were deparaffinized in xylene, and rehydrated in graded ethanol. Endogenous peroxidase activity was quenched by incubating sections in 0.3% $H_2O_2$ in PBS for 20 min. Nonspecific binding was blocked by incubating the sections with normal goat-serum for 30 min at room temperature. Sections were then incubated with the anti MUC4 antibody (1:100) diluted in PBS and a non-specific isotype matched antibody, K2G6, as a negative control for 1 h, at room temperature and washed with PBS-T (365 min) followed by incubation with secondary antibody for 30 min. Slides were washed (365 min) with PBS-T and incubated with the ABC solution. The reaction color was developed by incubating sections with 3,39-diaminobenzidine reagent. The slides were washed with water and counterstained with hematoxylin. The sections were then dehydrated in graded alcohols and mounted with Permount permanent mounting media (Fisher Scientific, Fair Lawn, N.J.). All slides were observed under Nikon E400 Light Microscope and representative photographs were taken.

Example 2

MUC4 Stabilizes HER2 Expression and Maintains the Cancer Stem Cell Population in Ovarian Cancer Cells Ovarian cancer is a highly lethal disease which represents a great clinical challenge in gynecologic oncology. It is asymptomatic until the disease is in the late stage, causing it to have the highest fatality-to-case ratio of all gynecologic malignancies. There is emerging evidence showing that cancer stem cells are capable of regenerating tumors and they are responsible for the aggressiveness of the disease, metastasis and resistance to therapy (Ponnusamy and Batra (2008) *J. Ovarian Res.*, 1: 4). Cancer stem cells, like somatic stem cells, are thought to be capable of self-renewal or unlimited proliferation. A recent study describes that ovarian cancer cell lines were shown to possess "side population" (SP) cells that have been described as cancer stem cells due to their ability to differentiate into tumors with different histologies, similar to the pluripotent character of stem cells (Id.). It is now believed that cancer often relapses after the treatment due to the stem-like population in some solid tumors (Dean et al. (2005) *Nat. Rev. Cancer*, 5: 275-284). Although advanced ovarian cancer is generally initially responsive to standard chemotherapies (cisplatin and paclitaxel), it is almost inevitably followed by the drug resistant phenotype. One accepted hypothesis about chemoresistance is that standard therapies fail to target tumor progenitors, which are like normal stem cells, because of the expression of membrane efflux transporters (Ponnusamy and Batra (2008) *J. Ovarian Res.*, 1: 4).

The alterations in the mucin expression or glycosylation pattern is often associated with the development of cancer via influencing cellular growth, differentiation, transformation, adhesion, invasion and immunosuppression (Andrianifahanana et al. (2001) *Clin. Cancer. Res.*, 7: 4033-4040; Hollingsworth and Swanson (2004) *Nat. Rev. Cancer*, 2004, 4:45-60). MUC4 frequently displays an altered expression under the pathological conditions of many cancers (Id.). Previously, our study has revealed an aberrant expression of MUC4 mucin in >90% of different histological subtypes and grades of ovarian tumors with very low or undetectable expression in the normal ovary (Chauhan et al. (2006) *Mod. Pathol.*, 19: 1386-1394). Overexpression of MUC4 mRNA has also been reported in ovarian cancer (Giuntoli et al. (1998) *Cancer Res.*, 58: 5546-5550). In our previous study, we showed that MUC4 interacts and stabilizes HER2 in both ovarian and pancreatic cancer cells (Chaturvedi et al. (2008) *Cancer Res.* 68: 2065-2070; Ponnusamy et al. (2008) *Br. J. Cancer*, 99: 520-526). We have further shown that MUC4 induces the epithelial to mesenchymal transition (EMT) through the upregulation of N-cadherin, and thereby induces metastasis of human ovarian cancer cells (Ponnusamy et al. (2010) *Oncogene*, 29: 5741-5754). A recent study has shown that HER2 amplification regulates the mammary stem/progenitor cell population and promotes carcinogenesis, tumorigenicity and invasive properties (Korkaya et al. (2008) *Oncogene*, 27: 6120-6130). Recently, Engelmann et al have demonstrated that MUC1 (a membrane bound mucin) is also expressed in the mammary stem/progenitor cells (Engelmann et al. (2008) *Cancer Res.*, 68: 2419-2426) and is important in the future application of MUC1-based therapies for complete cancer eradication.

The aforementioned observations suggest that MUC4 may have an important role in the pathogenesis of ovarian cancer. In this study, we have investigated increased expression of HER2 and the cancer stem cell population in MUC4 overexpressed ovarian cancer cells. Further, we have analyzed cancer stem cell and self-renewal specific markers in the isolated populations. In particular, as explained below, MUC4 was ectopically overexpressed in SKOV3 ovarian cancer cells. Western blot analysis was performed for MUC4, HER2, CD133, ALDH1 and Shh expression in MUC4 overexpressed cells. Confocal analysis of MUC4, HER2 and CD133 was also done in the MUC4 overexpressed cells. CD133 and Hoechst33342 dye staining was used to analyze the cancer stem cell population via FACS method in SKOV3-MUC4 cells. MUC4 overexpressed SKOV3 cells showed an increased expression of HER2 compared to control cells. MUC4 overexpression leads to increased (0.1%) side population (SP) and CD133-positive cancer stem cells compared to the control cells. Interestingly, the tumor sphere type circular colony formation was observed only in the MUC4 overexpressed ovarian cancer cells. Furthermore, the cancer stem cell marker CD133 was expressed along with MUC4 in the isolated circular colonies as analyzed by both confocal and western blot analysis. HER2 and cancer stem cell specific marker ALDH1 along with Shh, a self-renewal marker, showed increased expression in the isolated circular colonies compared to MUC4-transfected cells.

As further explained below, these studies demonstrate that MUC4 overexpression leads to an enriched ovarian cancer stem cell population either directly or indirectly through HER2. In future, this study would be helpful for MUC4-directed therapy for the ovarian cancer stem cell population.

Methods

Generation of MUC4 Construct

We generated a MUC4 minigene construct to overcome the transfection associated problems due to its large size and to investigate the biological function and effect of MUC4 expression in OC cells (Ponnusamy et al. (2008) *Br. J. Cancer*, 99: 520-526; Moniaux et al. (2007) *Br. J. Cancer*, 97: 345-357). The resultant MUC4 cDNA was subcloned into the pSecTag-C vector for further transfection studies.

Cell Culture and Transfection Procedure

SKOV3 cells was procured from ATCC (Manassas, Va., U.S.A.) and cultured in DMEM supplemented with 10% fetal calf serum and antibiotics. The MUC4 gene construct along with the empty vector control pSecTag-C, were transfected in SKOV3 OC cells by Fugene (Invitrogen) following the manufacturer's protocol. Transfected cells were selected in the medium containing 200 µg/ml zeocin (30 Days) and the drug-resistance (zeo+) clones (three from the empty vector, five from the MUC4 gene construct transfected) were selected from different plates and studied after expansion (Ponnusamy et al. (2008) *Br. J. Cancer*, 99: 520-526; Ponnusamy et al. (2010) *Oncogene*, 29: 5741-5754).

Immunoblot Assay

SKOV3 derived cell lines were processed for protein extraction and Western blotting using standard procedures. Briefly, the cells were washed twice in PBS and lysate was prepared in RIPA buffer (100 mM Tris, 5 mM EDTA, 5% NP40; pH8.0) containing protease inhibitors (1 mM phenylmethyl sulphonyl fluoride, 1 µg/ml aprotinin, 1 µg/ml leupeptin). SDS-PAGE (10%) was performed under standard conditions. Resolved proteins were transferred on to the PVDF membrane. After quick washing in PBST (Phosphate buffered saline and 0.1% Tween 20), the membranes were blocked in 5% nonfat dry milk in PBS for at least 2 h and then incubated with primary antibodies MUC4 (mouse), HER2 (rabbit), ALDH1 (rabbit), CD133 (rabbit), Shh (rabbit) and β-actin (mouse) (diluted in 5% non fat dry milk in PBS) overnight at room temperature. Then the membranes were washed (3×10 min) in PBST at room temperature and probed with 1:2000 diluted secondary antibodies (anti-mouse and anti-rabbit) for 1 h at room temperature and washed 5×10 min with PBST. The signal was detected with an ECL chemiluminescence kit (Amersham Bioscience, UK).

Confocal Immunofluorescence Microscopy

MUC4 and vector transfected SKOV3 cells were grown on sterilized cover slips for 20 h. Cells were washed with Hanks buffer containing 0.1 M HEPES, and fixed in ice-cold methanol at 20° C. for two minutes and blocked with 10% goat serum (Jackson Immunoresearch Labs, Inc., West Grove, Pa., U.S.A.) containing 0.05% Tween-20 for at least 30 minutes. For Phalloidin staining, cells were fixed with 3.6% formaldehyde-PBS solution and followed by permeabilization with 0.1% TritonX-100 in PBS for 20 min at room temperature. After the blocking step and a quick wash in PBS, cells were incubated with the MUC4, HER2 and CD133 for 60 minutes at room temperature. Then cells were washed (4×5 minutes each washing) with PBS containing 0.05% Tween-20 (PBS-T) and then incubated with FITC-conjugated anti-mouse (green) and Texas red conjugated anti-rabbit (red) secondary antibodies (Jackson Immunoresearch labs, Inc., West Grove, Pa.) for 30 minutes at room temperature in the dark. Propidium iodide was used for nuclear staining Cells were washed (5×5 minutes) again and mounted on glass slides in anti-fade Vectashield mounting medium (Vector Laboratories, Burlingame, Calif.). Laser confocal microscopy was performed by using a LSM 510 microscope (Carl Zeiss GmbH, Germany). Microphotographs of different stainings were taken in different channels separately.

Hoechst 33342 Dye and CD133 Staining for Flow Cytometry Analysis

Hoechst 33342 dye based FACS analysis have been used to determine the SP and NSP population in MUC4 overexpressed and control SKOV3 cells. Cells were stained with Hoechst 33342 (Sigma) as previously described (Szotek et al. (2006) Proc. Natl. Acad. Sci. USA, 103: 11154-11159). SP cells actively pump-out the dye (Hoechst 33342) and hence exhibit low fluorescence as compared to the NSP cells. Briefly, single cell suspension of OC cells was prepared at a density of $2 \times 10^6$/ml in pre-warmed DMEM mixed with Hoechst 33342 dye (5 μg/ml). The cells were incubated in water bath at 37° C. for 60 minutes and subsequently spun and re-suspended in cold HBSS+ (Hanks Balanced Salt Solution) containing 2 μg/ml propidium iodide (PI) for dead cell discrimination. Finally, the samples were run directly on the FACS and counted according to the strength of staining. The Hoechst dye was excited with the UV laser at 350 nm and its fluorescence measured with a 450/20 BP filter (Hoechst blue) and a 675 EFLP optical filter (Hoechst red). For the CD133-FITC and FACS analysis, $2 \times 10^7$ cells were incubated with FcR blocking reagent (MACS, Miltenyi Biotech) for 30 minutes. Then it was incubated with surface marker antibody CD133-FITC (MACS, Miltenyi Biotech) for 10 minutes. Finally, FACS analysis was carried out to count CD133-positive populations in MUC4-transfected and control SKOV3 cells.

Results

Ectopic Expression of MUC4 in SKOV3-Ovarian Cancer Cells

Figure 8A:
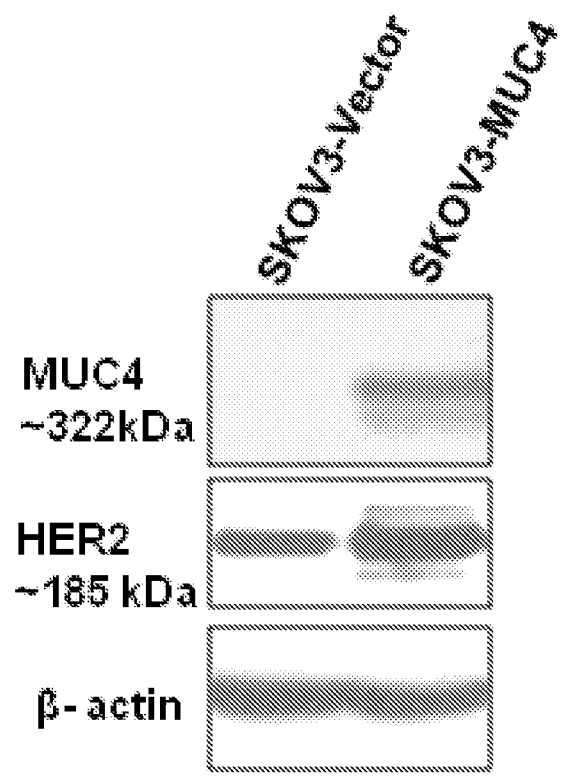
FIGS. 8A and 8B show the results of western blot and confocal analysis of MUC4 and HER2 in SKOV3 cells.
Figure 8B:
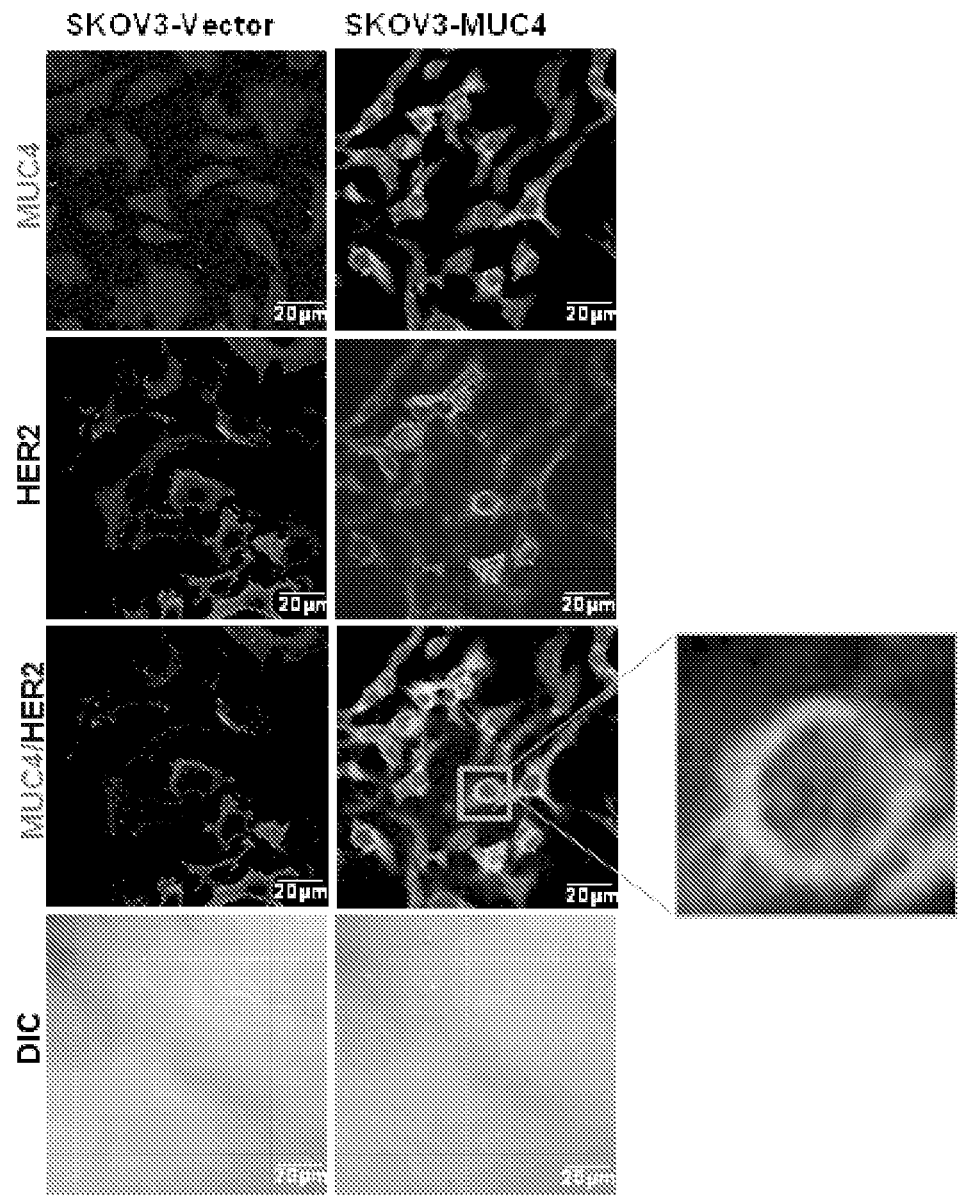

The MUC4 construct developed in our laboratory is similar to the wild-type MUC4 with 10% repetitive domain size of its originally described allele (Ponnusamy et al. (2008) Br. J. Cancer, 99: 520-526; Ponnusamy et al. (2010) Oncogene, 29: 5741-5754; Moniaux et al. (2007) Br. J. Cancer, 97: 345-357). Expression of MUC4 in stable cell transfectants were evaluated by Western blot analysis using a MUC4 antibody (8G7), which was developed in our laboratory that recognizes an epitope in the tandem repeat domain of MUC4. This antibody recognizes a MUC4 protein band of approximately 322 kDa specifically in the MUC4 gene transfected clone (SKOV3-MUC4) and not in the vector control (SKOV3-Vec) (FIG. 8A). Expression and localization of MUC4 was further confirmed by immunofluorescence confocal microscopy. Ninety percent of the SKOV3-MUC4 transfected cells showed localization of MUC4 in both cytoplasm and membranes (FIG. 8B) and an absence of MUC4 localization in vector-transfected SKOV3 cells (FIG. 8B).

Overexpression of MUC4 Stabilizes HER2 in Ovarian Cancer Cells

In our previous studies we have shown that MUC4 interacts with HER2 in ovarian cancer and pancreatic cancer cells (Chaturvedi et al. (2008) Cancer Res. 68: 2065-2070; Ponnusamy et al. (2008) Br. J. Cancer, 99: 520-526). In the present study we have analyzed the expression of HER2 in MUC4 overexpressed ovarian cancer cells. Our result showed that HER2 was upregulated in MUC4 overexpressed SKOV3 cells compared to the vector control (FIG. 8A). Furthermore, we have analyzed MUC4 and HER2 localization in the same cells by confocal immunofuorescence analysis. MUC4 and HER2 were co-localized in MUC4 overexpressed cells, most of which show an EMT phenotype (Ponnusamy et al. (2010) Oncogene, 29: 5741-5754). Interestingly, a few cells also showed a circular phenotype along with MUC4-HER2 co-localization (FIG. 8B). This suggests that ovarian cancer cells consist of a heterozygous population of cells having different phenotype. Side population and Non-side population in MUC4 transfected SKOV3 cells.

Recently, cancer stem cells have been identified as a minor population of cells sorted by flow cytometry based on their capacity to efflux the fluorescent DNA-binding dye Hoechst 33342. This is due to their overexpression of the ABCG2 drug resistance protein, one of the important characteristics of cancer stem/progenitor cells (Bunting (2002) Stem Cells, 20: 11-20; Kim et al. (2002) Clin. Cancer Res., 8: 22-28). This population of cells was termed side population (SP) and the other population was called the non-side population (NSP). In the present study we have analyzed the number of SP and NSP cells in MUC4-transfected and control cells. Our results showed that MUC4-transfected SKOV3 cells were 0.1% more enriched in the SP population as compared to the vector control cells (FIG. 9A). This suggests that overexpression of MUC4 leads to enrichment of the SP population in ovarian cancer cells.

Increased Number of CD133-Positive Cells in MUC4 Overexpressed SKOV3 Cells

CD133 is a cell surface antigen which was recognized as a stem cell specific marker for both normal and cancerous adult tissues. CD133 alone or along with other markers are currently used for the isolation of cancer stem cells from different cancer tissues and cell lines (Ferrandina et al. (2008) Int. J. Gynecol. Cancer, 18: 506-514; Ma et al. (2008) Oncogene, 27: 1749-1758). Qverexpressed MUC4 and control cells were stained with FITC-conjugated CD133 cells to analyze the percentage of the cancer stem cell population. Interestingly, MUC4-transfected SKOV3 cells showed a 0.1% increased CD133 population as compared to the control cells (FIG. 9B).

This further suggests that overexpression of MUC4 results in the enrichment of the cancer stem cell population in ovarian cancer cells.

Circular Colony Formation in MUC4-Transfected SKOV3 Cells

Figure 10:
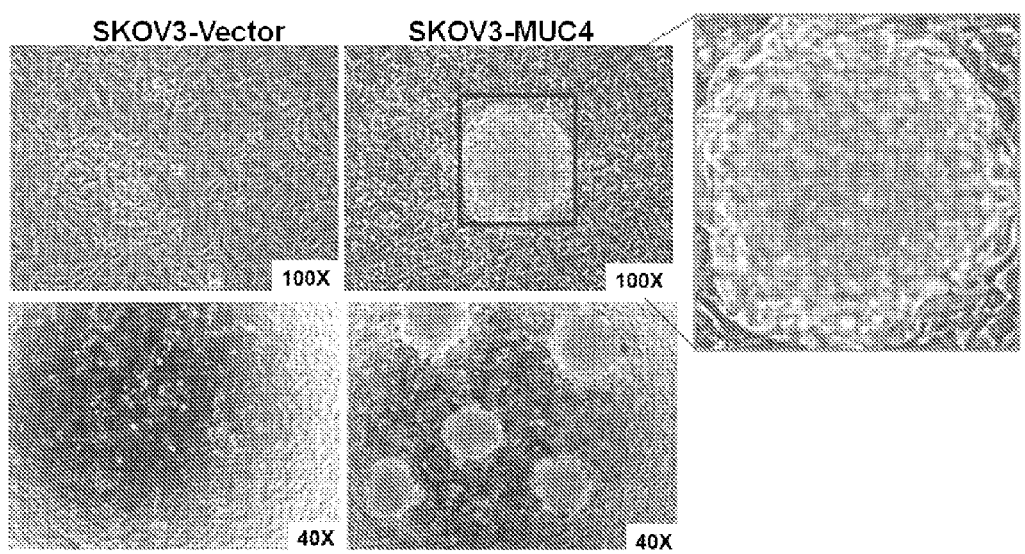
FIG. 10 illustrates colony formation in MUC4-trasfected cells. SKOV3-Vector and SKOV3-MUC4 cells were seeded in equal confluence and allowed to grow for up to 18 days. After the full confluence we observed a tumor sphere-like colony formation on the top of the cells. Circular colony formation was observed only in MUC4 overexpressed SKOV3 cells and no colonies were formed in SKOV3-vector cells. (Original magnification 100× upper panel and 40× lower panel).
Figure 11A:
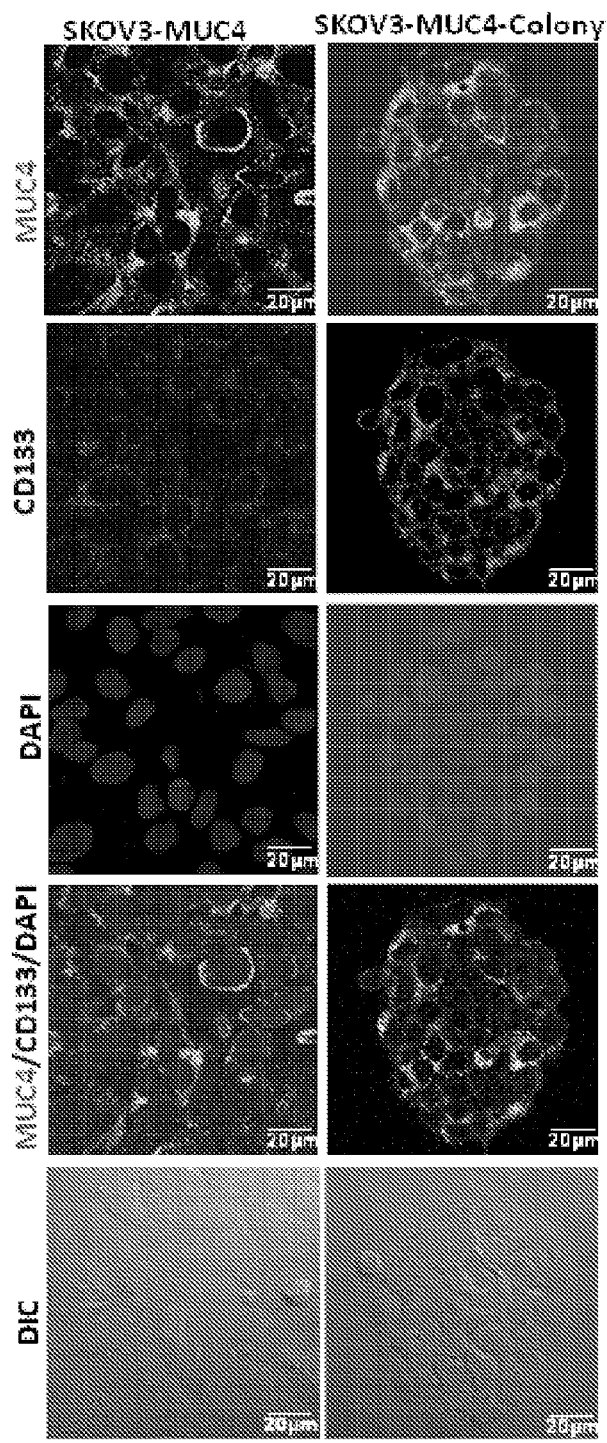
FIGS. 11A and 11B show the expression of cancer stem cell markers in circular colonies.
Figure 11B:
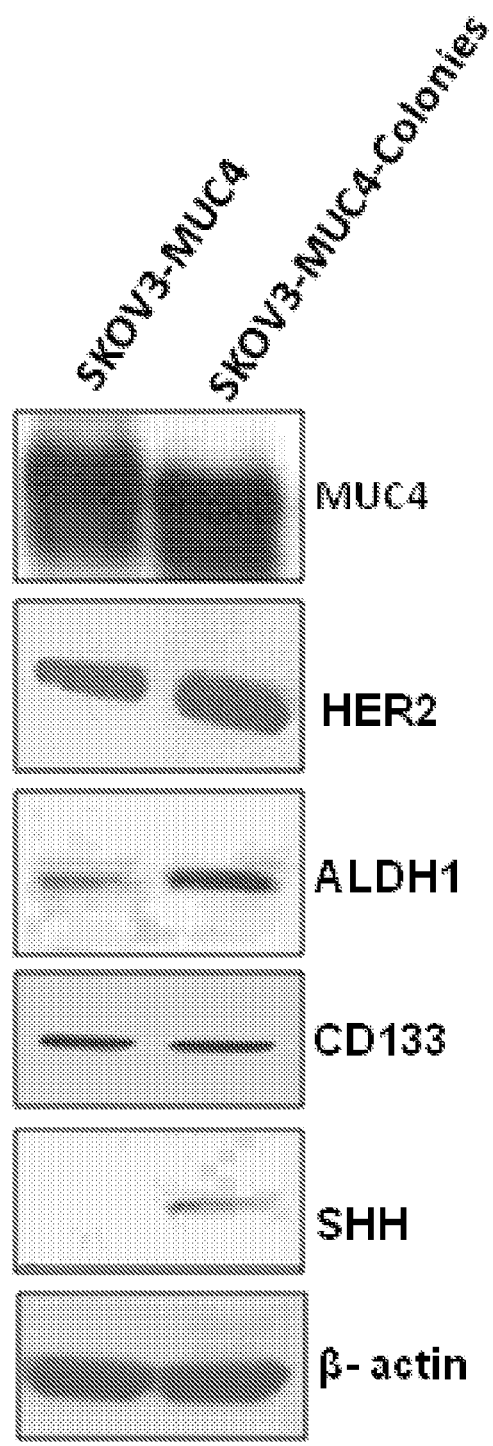
Figure 12:
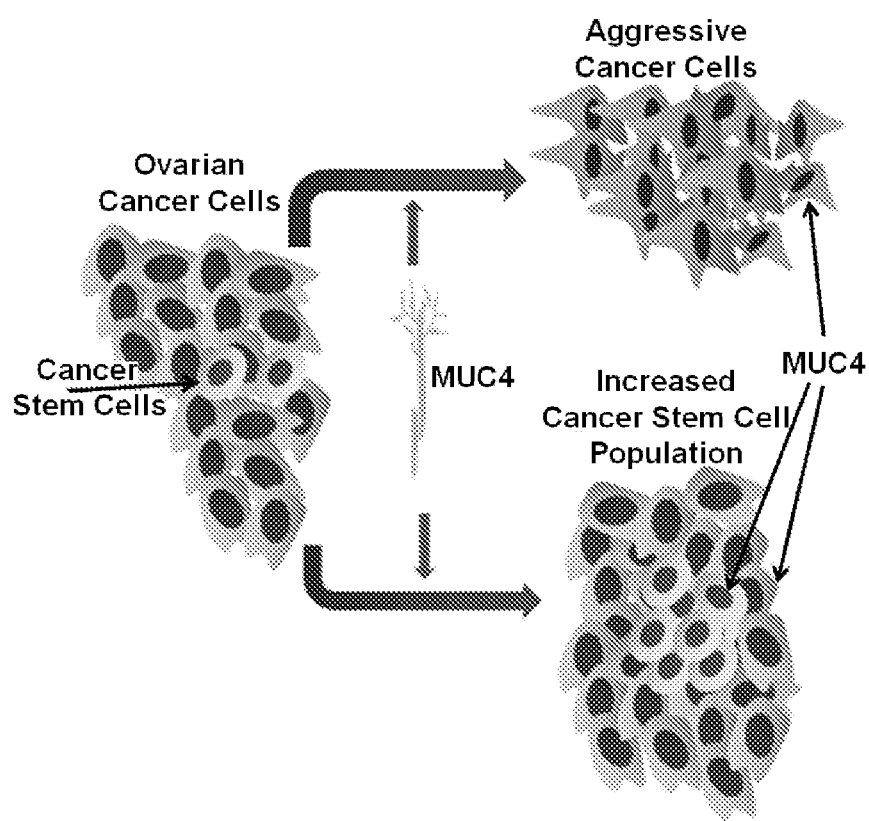
FIG. 12 provides a schematic representation showing that MUC4 overexpressed ovarian cancer cells induce the aggressiveness of the cancer cells and enrich the cancer stem cell population. It also shows that MUC4 is expressed in the ovarian cancer stem cell population.

Formation of spherical colonies has been reported to be a property characteristic of stem/progenitor cells and verifies a high developmental and proliferative potency of side population cells (Engelmann et al. (2008) Cancer Res., 68: 2419-2426). Interestingly, in our study we observed circular colony formation in MUC4-transfected SKOV3 cells when it became over confluent after three weeks (FIG. 10). In contrast, no colony formation was observed in vector-transfected SKOV3 cells (FIG. 10). We further isolated these colonies for the stem/progenitor marker analysis Expression of Cancer Stem Cell and Self-Renewal Markers in Circular Colonies Cancer stem cells express numerous universal markers such as CD133, CD44, CD24, ESA and ALDH1 in different cancers (Ponnusamy and Batra (2008) J. Ovarian Res., 1: 4). Few of these markers were used for the confirmation of an MUC4 enriched cancer stem cell population. Stem cells and cancer stem cells are known to possess the phenomenal property of self-renewal which is maintained by few specific pathways such as Shh, Wnt and Notch (Id.). The circular colonies or tumor spheres from MUC4-transfected SKOV3 cells were isolated and grown in a separate glass cover slip for the cancer stem cell marker analysis by confocal microscopy. The confocal results showed immunofluorescence staining of CD133 marker expression in the isolated colonies and SKOV3-MUC4 cells (FIG. 11A). On the other hand, MUC4 immunofluorescence staining is almost equal in both isolated colonies and SKOV3-MUC4 cells (FIG. 11A). In our study we have also analyzed MUC4, HER2, ALDH1 and CD133 for the cancer stem cells and Shh for the self-renewal pathway in the isolated colonies from MUC4 overexpressed SKOV3 cells and SKOV3-MUC4. MUC4 expression was observed at an almost equal level in both SKOV3-MUC4 and isolated colonies although there was a minor molecular weight change in isolated colonies (FIG. 11B). Interestingly, increased expression of HER2 was seen in isolated colonies compared to SKOV3-MUC4 cells. Expression of CD133 was also shown in both SKOV3-MUC4 and isolated colonies, whereas ALDH1 showed an increased expression in isolated colonies compared to MUC4 overexpressed SKOV3 cells (FIG. 11B). In addition, the Shh self-renewal protein expression was observed only in isolated colonies, while there was no expression in SKOV3-MUC4 (FIG. 11B). This suggests that the isolated colonies from MUC4 overexpressed cells behave like cancer stem cells which are capable of maintaining the self-renewal property (FIG. 12).

Discussion

Ovarian cancer is the fourth leading cause of cancer deaths among all women and has the highest mortality among the gynecologic cancers. It is one of the most challenging of all cancers to fight as it often goes undiagnosed until it has already advanced and metastasized. Furthermore, current therapeutic strategies have been inefficient and tumor recurrence is observed in up to 70% of patients with advanced stage ovarian cancer, even after treatment (Auersperg et al. (1998) Semin. Oncol. 25: 281-30; Jemal et al. (2009) CA Cancer J. Clin., 59: 225-249; Wong et al. (2003) Reprod. Biol. Endocrinol., 1: 70). Numerous evidences have revealed that a small population of cells behaving like stem-cells are responsible for the tumor recurrence and disease aggressiveness (Ponnusamy and Batra (2008) J. Ovarian Res., 1: 4). These populations of cells known as cancer stem cells have been demonstrated to have roles in many cancers, such as cancers of the hematopoietic system, ovarian, breast, brain, prostate, pancreas, colon and liver (Ponnusamy and Batra (2008) J. Ovarian Res., 1: 4; Dean et al. (2005) Nat. Rev. Cancer, 5: 275-284; Engelmann et al. (2008) Cancer Res., 68: 2419-2426; Szotek et al. (2006) Proc. Natl. Acad. Sci. USA, 103: 11154-11159; Ferrandina et al. (2008) Int. J. Gynecol. Cancer, 18: 506-514; Al-Hajj et al. (2003) Proc. Natl. Acad. Sci. USA, 100: 3983-3988; Collins et al. (2005) Cancer Res., 65: 10946-10951; Dalerba et al. (2007) Proc. Natl. Acad. Sci. USA, 104: 10158-10163; Marsden et al. (2009) Meth. Mol. Biol., 590: 363-375; Mimeault et al. (2007) J. Cell. Mol. Med., 11: 981-1011). To date, very few specific tumor antigens have been identified to target the cancer stem cell population to prevent tumor recurrence. Hence, the present study showed that MUC4 overexpression is enriching the cancer stem cell population and it is expressed in stem/progenitor cells in ovarian cancer cells.

MUC4 is known to be overexpressed in many types of carcinomas, including ovarian carcinoma (Andrianifahanana et al. (2001) Clin. Cancer. Res., 7: 4033-4040; Chauhan et al. (2006) Mod. Pathol., 19: 1386-1394; Boman et al. (2001) J. Pathol., 193: 339-344). The primary role of MUC4 is to protect the epithelial surface from injuries under normal physiological conditions, but overexpression is often correlated with the malignant phenotype. Our previous study reveals that MUC4 is aberrantly expressed in ovarian tumors (Chauhan et al. (2006) Mod. Pathol., 19: 1386-1394) and in pancreatic tumors (Andrianifahanana et al. (2001) Clin. Cancer. Res., 7: 4033-4040). Another study from our laboratory shows that down-regulation of MUC4 is involved in the suppression of pancreatic tumor cell growth and metastasis (Singh et al. (2004) Cancer Res., 64: 622-630). In our recent study, we have shown a direct association of the MUC4 mucin with the metastatic human ovarian cancer phenotype and also provided experimental evidence for a functional role of MUC4 in altered growth behavioral properties of the tumor cell (Ponnusamy et al. (2008) Br. J. Cancer, 99: 520-526). The ectopic expressed MUC4 gene has all the basic elements of the MUC4 gene but its tandem repeat region is only 10% of the wild-type MUC4 allele (Ponnusamy et al. (2008) Br. J. Cancer, 99: 520-526; Moniaux et al. (2007) Br. J. Cancer, 97: 345-357). As predicted, MUC4 overexpressed cells expressed an approximately 322 kDa protein. The localization of the MUC4 protein was observed in both the membrane and cytoplasm of SKOV3 ovarian cancer cells.

Our previous study demonstrates an altered expression of the human epidermal growth factor receptor 2 (HER2), also known as ErbB2, in MUC4 overexpressing cells (Ponnusamy et al. (2008) Br. J. Cancer, 99: 520-526). HER2 belongs to the epidermal growth factor receptor (EGFR) family. Most membrane-bound mucins have juxtamembrane domains with homology to the members of the EGF family (Hollingsworth and Swanson (2004) Nat. Rev. Cancer, 2004, 4:45-60). MUC4 has been shown to act as an unorthodox ligand for ErBB2/HER2 (Ramsauer et al. (2006) Mol. Biol. Cell, 17: 2931-2941), potentiating its responsiveness in cancer signaling (Chaturvedi et al. (2008) Cancer Res. 68: 2065-2070; Ponnusamy et al. (2008) Br. J. Cancer, 99: 520-526). Our recent finding showed that an overexpression of MUC4 increases the expression of HER2 in ovarian cancer cells (Ponnusamy et al. (2008) Br. J. Cancer, 99: 520-526) and stabilizes the HER2 oncoprotein in pancreatic cancer cells (Chaturvedi et al. (2008) Cancer Res. 68: 2065-2070). In the present study, we analyzed the expression of the HER2 protein in MUC4-transfected ovarian cancer cells. The exogenous MUC4 expression in ovarian cancer cells showed an increase in HER2 expression and colocalization, suggesting that MUC4 is involved in the stabilization of HER2 protein.

There is emerging evidence that small subpopulations that behave like stem cells are present in many types of cancer. These subpopulations are responsible for the initiation, drug resistance and tumor recurrence (Ponnusamy and Batra (2008) *J. Ovarian Res.,* 1: 4). Korkaya and colleagues showed that HER2-overexpression in breast cancer cells enriched the cancer stem cell population, evidenced by an increased number of tumor sphere formation and cancer stem cell marker aldehyde dehydrogenase expression (Korkaya et al. (2008) *Oncogene,* 27: 6120-6130). They have further shown an increased expression of stem cell regulatory genes, increased invasion in vitro and increased tumorigenesis in NOD/SCID mice (Id.). This suggests that, in addition to genetic alterations such as amplification, the expression of the HER2 level is important for the maintenance of CSCs. Recently, a minor population of cells was isolated by flow cytometry based on their capacity to efflux the fluorescent DNA-binding dye Hoechst 33342 to identify cancer stem cells. This is one of the important properties for cancer stem/progenitor cells (Bunting (2002) *Stem Cells,* 20: 11-20; Kim et al. (2002) *Clin. Cancer Res.,* 8: 22-28) because of the expression of ABCG2 drug resistance protein. In our study, we have observed enriched population of CSCs in MUC4-transfected ovarian cancer cells using Hoechst33342 dye and CD133-positive population analysis. Further, an interesting observation of tumor sphere like circular colony formation was observed predominantly in MUC4-transfected ovarian cancer cells and these colonies were isolated from the cells and analyzed with cancer stem cell markers. There was a slight change in the molecular weight of MUC4 protein in the isolated colonies suggesting that there may be some variation in glycosylation pattern, which will be explored in future studies (FIG. 11B). The enriched cancer stem cell population in MUC4 overexpressed cells may be due to the increased expression of HER2 expression. Furthermore, isolated circular colonies showed significant expression of cancer stem cell specific markers CD133 and ALDH1 and the self-renewal maintenance marker Shh, which concludes that MUC4 is enriching the cancer stem cell population in ovarian cancer cells. Similarly, a recent study showed that a membrane-bound mucin MUC1 maintains a small population of stem/progenitor cells in the breast cancer (MCF7) cell line (Engelmann et al. (2008) *Cancer Res.,* 68: 2419-2426). The fact that the vast majority of MCF7 stem cell enriched SP cells express MUC1 suggests that epithelial cancer stem cells would also be the targets of various immunotherapy approaches based on the MUC1 tumor antigen that has been designed with mature tumor cells in mind (Id.).

In conclusion, overexpression of MUC4 induces the HER2 level and enrichment of cancer stem cells in MUC4-transfected ovarian cancer cells. Circular colonies isolated from MUC4 overexpressed ovarian cancer cells show an increased expression of cancer stem cell specific markers (ALDH1 and CD133) and the self-renewal maker (Shh). This suggests that MUC4 stabilizes HER2 and enriches the cancer stem cell population, by either a direct or indirect mechanism which is yet to be explored. Our study proves that MUC4 is not only expressed on mature cancer cells, but also on tumor cells that have multiple characteristics of stem/progenitor cells (FIG. 12). This will help for the application of a specific therapeutic target for cancer stem cells.

Abbreviations

Abbreviations used in this example include: SP: Side Population; NSP: Non-Side Population; CSCs: Cancer stem cells; EMT: Epithelial to mesenchymal transition; EGFR: Epidermal Growth Factor Receptor.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated monoclonal antibody that binds a region of the MUC4 protein that does not comprise the central tandem repeat (TR) domain of MUC4, wherein said antibody binds to a peptide consisting of the amino acid sequence of MUC4-α-N-Ter (SEQ ID NO: 1), or to a peptide consisting of the amino acid sequence of MUC4-α-C-Ter (SEQ ID NO: 2).

2. The antibody of claim 1, wherein said antibody binds to the peptide consisting of the amino acid sequence of MUC4-α-N-Ter (SEQ ID NO: 1).

3. The antibody of claim 1, wherein said antibody binds to the peptide consisting of the amino acid sequence of MUC4-α-C-Ter (SEQ ID NO: 2).

4. The antibody of claim 1, wherein said antibody does not bind the central tandem repeat (TR) domain of MUC4.

5. The antibody of claim 1, wherein said antibody also binds to a cell that expresses a MUC4 protein.

6. The antibody of claim 5, wherein said cell is a cancer cell.

7. The antibody of claim 1, wherein said antibody is a monoclonal antibody or a fragment thereof.

8. The antibody of claim 7, wherein said antibody is an IgG or a fragment thereof, or an IgM or a fragment thereof.

9. The antibody of claim 1, wherein said antibody is produced by immunization of a non-human mammal with the MUC4-α-N-Ter and/or MUC4-α-C-Ter.

10. The antibody of claim 1, wherein said antibody is a humanized antibody.

11. The antibody of claim 1, wherein said antibody is attached to an effector.

12. The antibody of claim 11, wherein said effector is an effector selected from the group consisting of a cytokine, an epitope tag, a second antibody a detectable label, an anti-cancer drug, a delivery vehicle comprising an anti-cancer drug, a cytotoxin, a radionuclide, a prodrug, a viral particle, a radiosensitizer, and a chelate.

13. A pharmaceutical formulation said formulation comprising: a pharmaceutically acceptable excipient; and an isolated monoclonal antibody that binds a region of the MUC4 protein that does not comprise the central tandem repeat (TR) domain of MUC4, wherein said antibody binds to a peptide consisting of the amino acid sequence of MUC4-α-N-Ter (SEQ ID NO: 1), or to a peptide consisting of the amino acid sequence of MUC4-α-C-Ter (SEQ ID NO: 2).

14. The pharmaceutical formulation of claim 13, wherein said antibody binds to the peptide consisting of the amino acid sequence of MUC4-α-N-Ter (SEQ ID NO: 1).

15. The pharmaceutical formulation of claim 13, wherein said antibody binds to the peptide consisting of the amino acid sequence of MUC4-α-C-Ter (SEQ ID NO: 2).

16. A pharmaceutical formulation said formulation comprising: a pharmaceutically acceptable excipient; and an isolated monoclonal antibody that binds a region of the MUC4 protein that does not comprise the central tandem repeat (TR) domain of MUC4, wherein said antibody binds to a peptide consisting of the amino acid sequence of MUC4-α-N-Ter (SEQ ID NO: 1), or to a peptide consisting of the amino acid sequence of MUC4-α-C-Ter (SEQ ID NO: 2) wherein said antibody is attached to an effector.

17. The pharmaceutical formulation of claim 16, wherein said effector is an effector selected from the group consisting of a cytokine, an epitope tag, a second antibody a detectable label, an anti-cancer drug, a delivery vehicle comprising an anti-cancer drug, a cytotoxin, a radionuclide, a prodrug, a viral particle, a radiosensitizer, and a chelate.

\* \* \* \* \*

SEQUENCE LISTING

```
<160> NUMBER OF SEQ ID NOS: 8

<210> SEQ ID NO 1
<211> LENGTH: 924
<212> TYPE: PRT
<213> ORGANISM: Homo sapiens

<400> SEQUENCE: 1

Trp Val Asn Ala His Ala Tyr Pro Ala Gln Trp Thr Leu Gly Ser Asn
1               5                   10                  15

Thr Tyr Gln Ala Ile Leu Ser Thr Asp Gly Ser Arg Ser Tyr Ala Leu
            20                  25                  30

Phe Leu Tyr Gln Ser Gly Gly Met Gln Trp Asp Val Ala Gln Arg Ser
        35                  40                  45

Gly Asn Pro Val Leu Met Gly Phe Ser Ser Gly Asp Gly Tyr Phe Glu
    50                  55                  60

Asn Ser Pro Leu Met Ser Gln Pro Val Trp Glu Arg Tyr Arg Pro Asp
65                  70                  75                  80

Arg Phe Leu Asn Ser Asn Ser Gly Leu Gln Gly Leu Gln Phe Tyr Arg
                85                  90                  95

Leu His Arg Glu Glu Arg Pro Asn Tyr Arg Leu Glu Cys Leu Gln Trp
            100                 105                 110
```

-continued

```
Leu Lys Ser Gln Pro Arg Trp Pro Ser Trp Gly Trp Asn Gln Val Ser
        115                 120                 125

Cys Pro Cys Ser Trp Gln Gln Gly Arg Arg Asp Leu Arg Phe Gln Pro
    130                 135                 140

Val Ser Ile Gly Arg Trp Gly Leu Gly Ser Arg Gln Leu Cys Ser Phe
145                 150                 155                 160

Thr Ser Trp Arg Gly Gly Val Cys Cys Ser Tyr Gly Pro Trp Gly Glu
                165                 170                 175

Phe Arg Glu Gly Trp His Val Gln Arg Pro Trp Gln Leu Ala Gln Glu
            180                 185                 190

Leu Glu Pro Gln Ser Trp Cys Cys Arg Trp Asn Asp Lys Pro Tyr Leu
        195                 200                 205

Cys Ala Leu Tyr Gln Gln Arg Arg Pro His Val Gly Cys Ala Thr Tyr
    210                 215                 220

Arg Pro Pro Gln Pro Ala Trp Met Phe Gly Asp Pro His Ile Thr Thr
225                 230                 235                 240

Leu Asp Gly Val Ser Tyr Thr Phe Asn Gly Leu Gly Asp Phe Leu Leu
                245                 250                 255

Val Gly Ala Gln Asp Gly Asn Ser Ser Phe Leu Leu Gln Gly Arg Thr
            260                 265                 270

Ala Gln Thr Gly Ser Ala Gln Ala Thr Asn Phe Ile Ala Phe Ala Ala
        275                 280                 285

Gln Tyr Arg Ser Ser Ser Leu Gly Pro Val Thr Val Gln Trp Leu Leu
    290                 295                 300

Glu Pro His Asp Ala Ile Arg Val Leu Leu Asp Asn Gln Thr Val Thr
305                 310                 315                 320

Phe Gln Pro Asp His Glu Asp Gly Gly Gly Gln Glu Thr Phe Asn Ala
                325                 330                 335

Thr Gly Val Leu Leu Ser Arg Asn Gly Ser Glu Val Ser Ala Ser Phe
            340                 345                 350

Asp Gly Trp Ala Thr Val Ser Val Ile Ala Leu Ser Asn Ile Leu His
        355                 360                 365

Ala Ser Ala Ser Leu Pro Pro Glu Tyr Gln Asn Arg Thr Glu Gly Leu
    370                 375                 380

Leu Gly Val Trp Asn Asn Asn Pro Glu Asp Asp Phe Arg Met Pro Asn
385                 390                 395                 400

Gly Ser Thr Ile Pro Pro Gly Ser Pro Glu Glu Met Leu Phe His Phe
                405                 410                 415

Gly Met Thr Trp Gln Ile Asn Gly Thr Gly Leu Leu Gly Lys Arg Asn
            420                 425                 430

Asp Gln Leu Pro Ser Asn Phe Thr Pro Val Phe Tyr Ser Gln Leu Gln
        435                 440                 445

Lys Asn Ser Ser Trp Ala Glu His Leu Ile Ser Asn Cys Asp Gly Asp
    450                 455                 460

Ser Ser Cys Ile Tyr Asp Thr Leu Ala Leu Arg Asn Ala Ser Ile Gly
465                 470                 475                 480

Leu His Thr Arg Glu Val Ser Lys Asn Tyr Glu Gln Ala Asn Ala Thr
                485                 490                 495

Leu Asn Gln Tyr Pro Pro Ser Ile Asn Gly Gly Arg Val Ile Glu Ala
            500                 505                 510

Tyr Lys Gly Gln Thr Thr Leu Ile Gln Tyr Thr Ser Asn Ala Glu Asp
        515                 520                 525

Ala Asn Phe Thr Leu Arg Asp Ser Cys Thr Asp Leu Glu Leu Phe Glu
```

```
                530             535             540
Asn Gly Thr Leu Leu Trp Thr Pro Lys Ser Leu Glu Pro Phe Thr Leu
545                 550                 555                 560

Glu Ile Leu Ala Arg Ser Ala Lys Ile Gly Leu Ala Ser Ala Leu Gln
                565                 570                 575

Pro Arg Thr Val Val Cys His Cys Asn Ala Glu Ser Gln Cys Leu Tyr
                580                 585                 590

Asn Gln Thr Ser Arg Val Gly Asn Ser Ser Leu Glu Val Ala Gly Cys
                595                 600                 605

Lys Cys Asp Gly Gly Thr Phe Gly Arg Tyr Cys Glu Gly Ser Glu Asp
                610                 615                 620

Ala Cys Glu Glu Pro Cys Phe Pro Ser Val His Cys Val Pro Gly Lys
625                 630                 635                 640

Gly Cys Glu Ala Cys Pro Pro Asn Leu Thr Gly Asp Gly Arg His Cys
                645                 650                 655

Ala Ala Leu Gly Ser Ser Phe Leu Cys Gln Asn Gln Ser Cys Pro Val
                660                 665                 670

Asn Tyr Cys Tyr Asn Gln Gly His Cys Tyr Ile Ser Gln Thr Leu Gly
                675                 680                 685

Cys Gln Pro Met Cys Thr Cys Pro Pro Ala Phe Thr Asp Ser Arg Cys
                690                 695                 700

Phe Leu Ala Gly Asn Asn Phe Ser Pro Thr Val Asn Leu Glu Leu Pro
705                 710                 715                 720

Leu Arg Val Ile Gln Leu Leu Ser Glu Glu Asn Ala Ser Met
                725                 730                 735

Ala Glu Val Asn Ala Ser Val Ala Tyr Arg Leu Gly Thr Leu Asp Met
                740                 745                 750

Arg Ala Phe Leu Arg Asn Ser Gln Val Glu Arg Ile Asp Ser Ala Ala
                755                 760                 765

Pro Ala Ser Gly Ser Pro Ile Gln His Trp Met Val Ile Ser Glu Phe
                770                 775                 780

Gln Tyr Arg Pro Arg Gly Pro Val Ile Asp Phe Leu Asn Asn Gln Leu
785                 790                 795                 800

Leu Ala Ala Val Val Glu Ala Phe Leu Tyr His Val Pro Arg Arg Ser
                805                 810                 815

Glu Glu Pro Arg Asn Asp Val Val Phe Gln Pro Ile Ser Glu Glu Asp
                820                 825                 830

Val Arg Asp Val Thr Ala Leu Asn Val Ser Thr Leu Lys Ala Tyr Phe
                835                 840                 845

Arg Cys Asp Gly Tyr Lys Gly Tyr Asp Leu Val Tyr Ser Pro Gln Ser
                850                 855                 860

Gly Phe Thr Cys Val Ser Pro Cys Ser Arg Gly Tyr Cys Asp His Gly
865                 870                 875                 880

Gly Gln Cys Gln His Leu Pro Ser Gly Pro Arg Cys Ser Cys Val Ser
                885                 890                 895

Phe Ser Ile Tyr Thr Ala Trp Gly Glu His Cys Glu His Leu Ser Met
                900                 905                 910

Lys Leu Asp Ala Phe Phe Gly Ile Phe Gly Ala
                915                 920

<210> SEQ ID NO 2
<211> LENGTH: 431
<212> TYPE: PRT
<213> ORGANISM: Homo sapiens
```

<400> SEQUENCE: 2

```
Pro Leu Lys Met Glu Thr Ser Gly Met Thr Thr Pro Ser Leu Lys Thr
1               5                   10                  15

Asp Gly Gly Arg Arg Thr Ala Thr Ser Pro Pro Thr Thr Ser Gln
            20                  25                  30

Thr Ile Ile Ser Thr Ile Pro Ser Thr Ala Met His Thr Arg Ser Thr
                35                  40                  45

Ala Ala Pro Ile Pro Ile Leu Pro Glu Arg Gly Val Ser Leu Phe Pro
        50                  55                  60

Tyr Gly Ala Asp Ala Gly Asp Leu Glu Phe Val Arg Arg Thr Val Asp
65                  70                  75                  80

Phe Thr Ser Pro Leu Phe Lys Pro Ala Thr Gly Phe Pro Leu Gly Ser
                85                  90                  95

Ser Leu Arg Asp Ser Leu Tyr Phe Thr Asp Asn Gly Gln Ile Ile Phe
            100                 105                 110

Pro Glu Ser Asp Tyr Gln Ile Phe Ser Tyr Pro Asn Pro Leu Pro Thr
            115                 120                 125

Gly Phe Thr Gly Arg Asp Pro Val Ala Leu Val Ala Pro Phe Trp Asp
130                 135                 140

Asp Ala Asp Phe Ser Thr Gly Arg Gly Thr Thr Phe Tyr Gln Glu Tyr
145                 150                 155                 160

Glu Thr Phe Tyr Gly Glu His Ser Leu Leu Val Gln Gln Ala Glu Ser
                165                 170                 175

Trp Ile Arg Lys Ile Thr Asn Asn Gly Gly Tyr Lys Ala Arg Trp Ala
            180                 185                 190

Leu Lys Val Thr Trp Val Asn Ala His Ala Tyr Pro Ala Gln Trp Thr
            195                 200                 205

Leu Gly Ser Asn Thr Tyr Gln Ala Ile Leu Ser Thr Asp Gly Ser Arg
210                 215                 220

Ser Tyr Ala Leu Phe Leu Tyr Gln Ser Gly Gly Met Gln Trp Asp Val
225                 230                 235                 240

Ala Gln Arg Ser Gly Lys Pro Val Leu Met Gly Phe Ser Ser Gly Asp
                245                 250                 255

Gly Phe Phe Glu Asn Ser Pro Leu Met Ser Gln Pro Val Trp Glu Arg
            260                 265                 270

Tyr Arg Pro Asp Arg Phe Leu Asn Ser Asn Ser Gly Leu Gln Gly Leu
            275                 280                 285

Gln Phe Tyr Gly Leu His Arg Glu Glu Arg Pro Asn Tyr Arg Leu Glu
            290                 295                 300

Cys Leu Gln Trp Leu Lys Ser Gln Pro Arg Trp Pro Ser Trp Gly Trp
305                 310                 315                 320

Asn Gln Val Ser Cys Pro Cys Ser Trp Gln Gln Gly Arg Arg Asp Leu
                325                 330                 335

Arg Phe Gln Pro Val Ser Ile Gly Arg Trp Gly Leu Gly Ser Arg Gln
            340                 345                 350

Leu Cys Ser Phe Thr Ser Trp Arg Gly Gly Val Cys Cys Ser Tyr Gly
            355                 360                 365

Pro Trp Gly Glu Phe Arg Glu Gly Trp His Val Gln Arg Pro Trp Gln
            370                 375                 380

Leu Ala Gln Glu Leu Glu Pro Gln Ser Trp Cys Cys Arg Trp Asn Asp
385                 390                 395                 400

Lys Pro Tyr Leu Cys Ala Leu Tyr Gln Gln Arg Arg Pro His Val Gly
```

```
                    405                 410                 415
Cys Ala Thr Tyr Arg Pro Pro Gln Pro Ala Trp Met Phe Gly Asp
            420                 425                 430

<210> SEQ ID NO 3
<211> LENGTH: 15
<212> TYPE: PRT
<213> ORGANISM: Artificial
<220> FEATURE:
<223> OTHER INFORMATION: Peptide linker

<400> SEQUENCE: 3

Gly Gly Gly Gly Ser Gly Gly Gly Ser Gly Gly Gly Gly Ser
1               5                   10                  15

<210> SEQ ID NO 4
<211> LENGTH: 8
<212> TYPE: PRT
<213> ORGANISM: Artificial
<220> FEATURE:
<223> OTHER INFORMATION: Affinity tag

<400> SEQUENCE: 4

Asp Tyr Lys Asp Asp Asp Asp Lys
1               5

<210> SEQ ID NO 5
<211> LENGTH: 4
<212> TYPE: PRT
<213> ORGANISM: Artificial
<220> FEATURE:
<223> OTHER INFORMATION: Affinity tag

<400> SEQUENCE: 5

His His His His
1

<210> SEQ ID NO 6
<211> LENGTH: 5
<212> TYPE: PRT
<213> ORGANISM: Artificial
<220> FEATURE:
<223> OTHER INFORMATION: Affinity tag

<400> SEQUENCE: 6

His His His His His
1               5

<210> SEQ ID NO 7
<211> LENGTH: 6
<212> TYPE: PRT
<213> ORGANISM: Artificial
<220> FEATURE:
<223> OTHER INFORMATION: Affinity tag

<400> SEQUENCE: 7

His His His His His His
1               5

<210> SEQ ID NO 8
<211> LENGTH: 4
<212> TYPE: PRT
<213> ORGANISM: Artificial
<220> FEATURE:
<223> OTHER INFORMATION: Peptide linker
```

```
<400> SEQUENCE: 8

Gly Phe Leu Gly
1
```